US007579143B2

(12) United States Patent
Whitcomb

(10) Patent No.: US 7,579,143 B2
(45) Date of Patent: Aug. 25, 2009

(54) METHOD OF ASSESSING THE EFFECTIVENESS OF A NON-NUCLEOSIDE REVERSE TRANSCRIPTASE INHIBITOR (NNRTI) ON A HUMAN IMMUNODEFICIENCY VIRUS TYPE 1 (HIV-1)-INFECTED PATIENT

(75) Inventor: Jeannette Whitcomb, San Mateo, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 712 days.

(21) Appl. No.: 10/758,683

(22) Filed: Jan. 14, 2004

(65) Prior Publication Data

US 2005/0059033 A1    Mar. 17, 2005

Related U.S. Application Data

(62) Division of application No. 09/320,299, filed on May 26, 1999, now Pat. No. 7,037,644.

(60) Provisional application No. 60/124,090, filed on Mar. 12, 1999, provisional application No. 60/086,834, filed on May 26, 1998.

(51) Int. Cl.
    C12Q 1/70         (2006.01)
(52) U.S. Cl. .......................... 435/5; 424/208.1
(58) Field of Classification Search ....................... 435/5
    See application file for complete search history.

(56) References Cited

U.S. PATENT DOCUMENTS

| | | |
|---|---|---|
| 5,436,131 A | 7/1995 | Condra et al. |
| 5,631,128 A | 5/1997 | Kozal et al. |
| 5,650,268 A | 7/1997 | Kozal et al. |
| 5,837,464 A | 11/1998 | Capon et al. |
| 5,917,033 A | 6/1999 | Modak et al. |
| 6,033,902 A | 3/2000 | Haseltine et al. |
| 6,103,462 A | 8/2000 | Paulous et al. |
| 6,124,327 A | 9/2000 | Silverman et al. |
| 6,242,187 B1 | 6/2001 | Capon et al. |
| 6,653,081 B2 | 11/2003 | Whitcomb |
| 2004/0067487 A1 | 4/2004 | Whitcomb |

FOREIGN PATENT DOCUMENTS

| | | |
|---|---|---|
| EP | 99925874 | 9/2004 |
| EP | 99933581 | 9/2004 |
| EP | 0194452 | 10/2004 |
| WO | WO97/27319 | 7/1997 |
| WO | WO97/27332 | 7/1997 |
| WO | PCT/US99/14486 | 6/1999 |
| WO | WO99/67427 | 6/1999 |
| WO | PCT/US99/11629 | 9/1999 |
| WO | WO99/61658 | 12/1999 |
| WO | WO02/22781 | 9/2001 |
| WO | PCT/US01/18882 | 10/2001 |
| WO | PCT/US01/28736 | 5/2002 |
| WO | PCT/US03/21024 | 5/2004 |

OTHER PUBLICATIONS

Fujiwara, T., et al., 1998, S-1153 inhibits replication of known drug-resistant strains of human immunodeficiency virus type 1, Antimicrob. Agents Chemother. 42(6):1340-1345.*
Fujiwara, T., et al., 1998, "S-1153 inhibits replication of known drug-resistant strains of human immunodeficiency virus type 1", Antimicrob. Agents Chemother. 42(6): 1340-1345.*
Bacheler, L, et al., 2001, "Genotypic correlates of phenotypic resistance to efavirenz in virus isolates from patients failing non-nucleoside reverse transcriptase inhibitor therapy", J. Virol. 75(11):4999-5008.*
Ceccherini-Silberstein, F., et al., 2007, "Characterization and structural analysis of novel mutations in human immunodeficiency virus type 1 reverse transcriptase involved in the regulation of resistance to nonnucleoside inhibitors", J. Virol. 81(20):11507-11519.*
Ahluwalia, G. S., et al. (1996) "2', 3'-Didehydro-3$^1$-deoxythymidine: Regulation of its Metabolic Activation by Modulators of Thymidine-5'-triphosphate Biosynthesis" Mol. Pharm. 50: 160-165.
Appelt, et al., (1991) "Design of Enzyme Inhibitors Using Iterative Protein Crystallographic Analysis," J. Med. Chem. 34: 1925-1934.
Arnold E., et al. (1995) "Structures of DNA and RNA Polymerases and Their Interactions with Nucleic Acid Substrates", Curr Opin Struct Biol 5:27-38.
Back, KT, et al, (1996) "Reduce Replication of 3TC-Resistant HIV-1 Variants in Primary Cells Due to a Processivity Defect of the Reverse Transcriptase Enzyme", EMBO 15: 4040-4049.
Balzarini J, (1998) "A Novel Mutation (F227L) Arises in the Reverse Transcriptase of Human Immunodeficiency Virus Type 1 on Dose-Escalating Treatment of HIV Type 1-Infected Cell Cultures With the Nonnucleoside Reverse Transcriptase Inhibitor Thiocarboxanilide UC-781" AIDS Res. Human, 14(3):255-260.
Balzarini J, et al. (1997) "Zidovudine-Resistant Human Presence Immunodeficiency Virus Type 1 Strains Subcultured in the of Both Lamivudine and Quinoxaline HBY 097 Retain Marked Sensitivity to HBY 097 but not to Lamivudine" J of Infect Dis, 176:1392-1397.
Balzarini J., et al., (1992) "HIV-1-Specific Reverse Transcriptase Inhibitors Show Differential Activity Against HIV1 Mutant Strains Containing Different Amino Acid Substitutions in the Reverse Transcriptase", Virology 192:246-253.
Barnes WM, (1994) "PCR Amplification of up to 35-kb DNA with High Fidelity and High Yield from I. Bacteriophage Templates" PNAS 91:2216-2220.
Bartenschlager R, et al, (1994) "Kinetic and Structural Analyses of Hepatitis C Virus Polyprotein Processing", J. Virol. 68:5045-5055.
Boucher Cab, et al, (1993) "High-Level Resistance to (−) Enantiomeric 2'-Deoxy-3'-Thiacytidine In Vitro is Due to One Amino Acid Substitution in the Catalytic Site of Human Immunodeficiency Virus Type 1 Reverse Transcriptase", Antimicrob Agents Chemother, 37:2231-2234.

(Continued)

Primary Examiner—Jeffrey S. Parkin
(74) Attorney, Agent, or Firm—Jones Day

(57) ABSTRACT

This invention relates to methods for assessing the effectiveness of non-nucleoside reverse transcriptase inhibitor on an HIV that rely on detection of combinations of mutations in HIV reverse transcriptase associated with altered susceptibility to such compounds. In some embodiments, the combinations of mutations include various combinations of mutations at codons 190, 101, 130, and 98 of HIV reverse transcriptase.

4 Claims, 27 Drawing Sheets

OTHER PUBLICATIONS

Boucher Cab, et al, (1990) "Zidovudine sensitivity of human immunodeficiency viruses from high-risk, symptom-free individuals during therapy", Lancet 336:585-590.

Boyer, et al., "Analysis of Nonnucleoside Drug-Resistant Variants of Human Immunodeficiency Virus Type 1 Reverse Transcriptase," J. Virol., 67(4):2412-2420 (1993).

Cheeseman S.H., et al. (1995) "Phase I/II Evaluation of Defic Nevirapine Alone and in Combination with Zidvudine for Infection with Human Immunodeficiency Virus", J Acquir Immune Syndr 8:141-151.

Coffin JM, (1995) "HIV Population Dynamics in Vivo: Implications for Genetic Variation, Pathogenesis, and Therapy", Science 267:483-489.

Craig C and Moyle G, (1997) "The development of resistance of HIV-1 to zalcitabine", AIDS 11:271-279.

Croteau G. et al (1997) "Impaired Fitness of Human Immunodeficiency Virus Type 1 Variants with High-Level Resistance to Protease Inhibitors" J Virol 71:1089-1096.

D'Aquilla R.T. (1994) "Molecular Pathogenesis and Laboratory Monitoring", Clin Lab Med 14:393-423.

De Clercq E, (1997) "Development of Resistance of Human the 4); Immunodeficiency Virus (HIV) to Anti-HIV Agents: How to Prevent Problem" Intnl of Antimicro Agnts, 9:21-36.

De Clerq E, (1992) "HIV Inhibitors Targeted at the Reverse Transcriptase", AIDS Res. Hum Retrovin.8:119-134.

DeJong, M.D., et al. (1994) "Alternating Nevirapine and Infected Zidovudine Treatment of Human Immunodeficiency Virus Type 1Persons Does Not Prolong Nevirapine Activity", J Infect Dis 169:1346-1350.

DeJong MD, et al, (1996) "Host-parasite Dynamics and Outgrowth of Virus Containing a Single K7OR Amino Acid Change in Reverse Transcriptase are Responsible for the Loss of Human Immunodeficiency Virus Type 1 RNA Load Suppression by Zidovudine", PNAS 93:5501-5506.

Descamps, et al., 1997 "Susceptibility of Human Immunodeficiency Virus Type 1 Group O Isolates to Antiretroviral Agents: In Vitro Phenotype and Genotypic Analysis," J. of Virology 71(11): 8893-98.

De Antoni A., et al. Mutations in a pol gene of human immunodeficiency virus type 1 in infected patients receiving didanosine and hydroxyurea combination therapy.J. Infect Dis. Oct. 1997; 176(4): 899-903.

Doyon L, et al, (1996) "Second Locus Involved in Human Immunodeficiency Virus Type 1 Resistance to Protease Inhibitors",J Virol 70:3763-3769.

Dueweke, T.J., et al. (1993) "A Mutation in Reverse to Other Transcriptase of Bis (Heteroaryl) Piperzine Resistant Human Immunodeficiency Virus Type 1. That Confers Increased Sensitivity; Nonnucleoside Inhibitors", PNAS 90:4713-4717.

Eastman, P. Scott, et al. (1995) Monisotopic Hybridization Assay for Determination of Relative Amounts of Genotypic Human Micro, Immunodeficiency Virus Type 1 Zidovudine Resistance, J Clin 2777-2780.

Fitzgibbon et al. Human Immunodeficiency virus type 1 pol gene mutations in an AIDS pateint treated with multiple antiretroviral drugs. Journal of Virology, vol. 67, No. 12 (1993) pp. 7271-7275.

Frenkel et al. Specific, sensitive, and rapid assay for human immunodeficiency virus type 1 pol mutations associated with resistance to zidovudine and didanosine. Journal of Clinical Immunology. vol. 33, No. 2 (1995) pp. 342-347.

Frost, S.D.W., and McLean, A.R. (1994) "Quasispecies Dynamics and the Emergence of Drug Resistance During Zidovudine Therapy of Hiv Infection", AIDS 8:323-332.

Gerondelis P, et al, (1999) "The P236L Delavirdine-Resistant Human Immunodeficiency Virus Type 1 Mutant is Replication Defective and Demonstrates Alternations in both RNA 5'-End-and DNA 3',-End-Directed Rnase H Activities", J Virol. 73: 5803-5813.

Gervaix, et al., "A New Reporter Cell Line to Monitor HIV Infection and Drug Susceptibility in Vitro", Proc. Natl. Acad. Sci. USA (1997), vol. 94 pp. 4653-4658.

Goulden MG, et al, (1996) "Selection In Vitro of an HIV-1 Variant Resistant to Both Lamivudine (3TC) and Zidvudine", AIDS 10:101-102.

Gu Z, et al, (1994) "Identification of Novel Mutations that Confer Drug Resistance In the Human Immunodeficiency Virus Polymerase Gene", Leukemia 8(1):166-169.

Hammond, et al., 1998 "Mutations in Retroviral Genes Associated with Drug Resistance," 36-79.

Harrigan PR, et al, (1998) "Relative Republication Fitness of Zidovudine-Resistant Human Immunodeficiency Virus Type 1 Isolates In Vitro", J Virol. 72:3773-3778.

Ho DD, et al, (1994) "Characterization of Human Immunodeficiency Virus Type 1 Variants with Increased Resistance to a C2-Symmetric Protease Inhibitor", J Virol 68:2016-2020.

Holodniy, Mark, et al. (1995) "Determination of Human Immunodeficiency Virus RNA In Plasma and Cellular Viral DNA Genotypic Zidovudine Resistance Combination Therapy", J Virol, 3510-3516.

Hazuda, et al., 2000 "Inhibitors of Strand Transfer That Prevent Integration and Inhibit HIV-1 Replication in Cells," Science 287: 646-650.

Herrmann, et al., "A Working Hypotheses-Virus Resistance Development As An Indicator of Specific Antiviral Activity", Ann. NY Acad Sciences (1997), 284: 632-637.

Hertogs, et al., "A Rapid Method for Simultaneous Detection of Phenotypic Resistance to Inhibitors of Protease and Reverse Transcriptase in Recombinant Human Immunodeficiency Virus Type 1 Isolates From Patients Treated with Antiretroviral Drugs", Antimicrobial Agents and Chemotherapy (1998) 42(2): 269-276.

Iversen et al. "Multidrug-resistant immunodeficiency virus type 1 strains resulting from combination antiretroviral therapy," Journal of Virology. vol. 70, No. 2 (1996) pp. 1086-1090.

Kellam, P., et al. (1994) "Zidovudine Treatment Results in the Selection of Human Immunodeficiency Virus Type 1 Variants Whose Genotypes Confer Increasing Levels of Drug Resistance", J Gen Virol 75:341-351.

Kim EE, et al, (1995) "Crystal Structure of HIV-1 Protease in Complex with VX-478, a Potent and Orally Bioavailable Inhibitor of the Enzyme", J Am Chem Soc. 117: 1181-1182.

Kleim, J., et al. (1997) "In vitro Selection for Different Mutational Patterns in the HIV-1 Reverse Transcriptase Using High and Low Selective Pressure of the Nonnucleoside Reverse Transcriptase inhibitor HBY 097" Virology. 231: 112-118.

Kosalaraksa P, et al, (1999) "Comparative Fitness of Multi-Dideoxynucleoside-Resistant Human Immunodeficiency Virus Type 1 (HIV-1) in an In Vitro Competitive HIV-1 Replication Assay", J Virol 73:5356-5363.

Krebs, R., et al. 1997 "Single-Step Kinetics of HIV-1 Reverse Transcriptase Mutants Responsible for Virus Resistance to Nucleoside Inhibitors Responsible for Virus Resistance to Nucleoside Inhibitors Zidovudine and 3-TC" Biochemistry 36: 10292-10300.

Kuritzkes D.R. Clinical significance of drug resistance in HIV-1 infection. AIDS (1996) vol. 10, S27-S31.

Larder BA, (1992) "3'-Azido-3'-Deoxythymidine Resistance Suppressed by a Mutation Conferring Human Immunodeficiency Virus Type 1 Resistance to Nonnucleoside Reverse Transcriptase Inhibitors", Antimicrob Agents Chemother 36: 2664-2669.

Larder BA, et al, (1991) "Zidovudine resistance predicted by direct detection of mutations in DNA from HIV-infected lymphocytes", AIDS 5:137-144.

Larder BA, et al, (1995) "Potential Mechanism for Sustained Antiretroviral Efficacy of AZT-3TC Combination Therapy", Science 269:696-699.

Lie, et al., "Advances In Quantitative PCR Technology: 5' Nuclease Assays", Curr Opinion Biotech (1998), 9(1): 43-48.

Lieven Stuyver, et al. (1997) "Line Probe Assay For Rapid Detection Of Drug Selected Mutations In The Human Immunodeficiency Virus Type 1 Reverse Transcriptase Gene", Antimicro Aaen and Chemother, 284-291.

Lin PF, et al, (1994) "Genotypic and Phenotypic Analysis of Human Immunodeficiency Virus Type 1 Isolates from Patients on Prolonged Stavudine Therapy", J Infect Disease 170:1157-1164.

Lopez-Galindez C, et al, (1991) "Characterization of genetic variation and 3'-azido-3'-deoxythymidine-resistance mutations of human immunodeficiency virus by the RNAase A mismatch cleavage method", PNAS 88:4280-4284.

Mammamo F, et al, (1998) "Resistance-Associated Loss of Viral Fitness in Human Immunodeficiency Virus Type 1: Phenotypis Analysis of Protease and gag Coevoluation in Protease Inhibitor-Treated Patients", J Virol 72:7632-7637.

Maschera B, et al, (1996) "Mutations in the Viral Protease that Confer Resistance to Saquinavir Increase the Dissociation Rate Constant of the Protease-Saquinavir Complex", Bio Chem 271:33231-33235.

Mayers DL, et al, (1992) "Characterization of HIV Isolates Arising After Prolonged Zidovudine Therapy", J Acq Imm Def Synd 5:749-759.

Moyle GJ (1996) "Use of Viral Resistance Patterns to Antiretroviral Drugs in Optimizing Selection of Drug Combinations and Sequences", Drugs 52:168-185.

Mohri, H., et al. (1993) "Quantitation of Zidovudine Resistant Human Immunodeficiency Virus Type 1 in the Blood of Treated and Untreated Patients", *PNAS* 90:25-29.

Mulligan RC and Berg P, (1980) "Expression of a Bacterial Gene in Mammalian Cells", Science 209:1422-11427.

Nájera, I., et al. (1994) "Natural Occurrence of Drug Resistance Mutations in the Reverse Transcriptase of Human Immunodeficiency Virus Type 1 Isolates", *Aids Res Hum Retroviruses* 10:1479-1488.

Nájera, I., et al. (1995) "pol Gene Quasispecies of Human Immunodeficiency Virus: Mutations Associated with Drug Resistance in virus from Patients Undergoing No Drug Therapy", *J Virol* 69:23-31.

Nijhuis, et al., "Implications of Antiretroviral Resistance on Viral Fitness", Curr. Opin. Infect Diseases (2001), 14: 23-28.

Nunberg, J.H., et al. (1990) "Viral Resistance to Human Immunodeficiency Virus Type 1-Specific Pyridinone Reverse Transcriptase Inhibitors", *J Virol* 65:4887-4892.

Pelemans H, et al. (1997) "Characteristics of the Pro225His Mutation in Human Immunodeficiency Virus Type 1 (HIV-1) Reverse Transcriptase That Appears Under Selective Pressure of Dose Escalating Quinoxaline Treatment of HIV-1" *J. Virol.*, 71(11):8195-8203.

Petropoulos, et al., "A Novel Phenotypic Drug Susceptibility Assay For Human Immunodeficiency Virus Type 1", Antimicrobial Agents and Chemotherapy (2000), 44(4): 920-928.

Race, et al., "Analysis of HIV Cross-Resistance to Protease Inhibitors Using A Rapid Single-Cycle Recombinant Virus Assay For Patients Failing On Combination Therapies", AIDS (1999), 13(15): 2061-2068.

Richman, D.D. et al. (1994) "Nevirapine Resistance Mutations of Human Immunodeficiency Virus Type 1 Selected during Therapy", *J Virol* 68:1660-1666.

Richman, D.D. et al. (1991) "Human Immunodeficiency Virus Type 1 Mutants Resistant to Nonnucleoside Inhibitors of Reverse Transcriptase Arise in Tissue Culture", *PNAS* 88:11241-11245.

Sanger, et al. (1977) "DNA Sequencing with Chain-terminating Inhibitors", *PNAS* 88: 11241-245.

Sakar, G. and Sommer, S.S. (1990) "The Megaprimer Method of Site-Directed Mutagenesis" *Biotech*, 8(4):404-407.

Shafer RW, et al, (1994) "Combination Therapy with Zidovudine and Didanosine Selects for Drug-Resistant Human Immunodeficiency Virus Type 1 Strains wtih Unique Patterns of pol Gene Mutations", *J Infect Disease* 169:722-729.

Shi, et al., "A Recombinant Retroviral System for Rapid In Vivo Analysis of Human Immunodeficiency Virus Type 1 Susceptibility to reverse Transcriptase Inhibitors", Antimicrobial Agents and Chemotherapy (1997) 41(12): 2781-85.

Shirasaka T, et al, (1995) "Emergence of Human Immunodeficiency Virus Type 1 Variants with Resistance to Multiple Deoxynucleosides in Patients Receiving Therapy with Dideoxynucleosides", *PNAS* 92:2398-2402.

Southern, et al. (1982) "Transformation of Mammalian Cells to Antibotic Resistance with a Bacterial Gene Under Control of the SV40 Early Region Promoter", Appl. Genet 1:327-341.

Strair RK, et al. (1993) "Recombinant Retroviral Systems For the Analysis of Drug Resistant HIV" *Nucl Acds Res*, 21(20): 4836-4842.

Sugden B, et al, (1985) "A Vector that Replicates as a Plasmid and can be Efficiently Selected in B-Lymphoblasts Transformed by Epstein-Barr Virus", Mol Cell Bio 5:410-413.

Tisdale M, et al, (1993) "Rapid In Vitro Selection of Human Immunodeficiency Virus Type 1 Resistant to 3'-Thiacytidine Inhibitors due to a Mutation in the YMDD Region of Reverse Transcriptase", *PNAS* 90:5653-5656.

Vacca JP, et al, (1994) "L-735,524: An Orally Bioavailable Human Immunodeficiency Virus Type 1 Protease Inhibitor", PNAS 91:4096-4100.

Villahermosa, ML, et al. "Evaluations of mixtures of wild-type HIV-1 and HIV-1 with resistance point mutations against reverse transcriptase inhibitors" *Antiviral Ther.* (1998); 3(4):221-227.

Zennou V, (1998) "Loss of Viral Fitness Associated with Multiple Gag and Gag-Pol Processing Defects in Human Immunodeficiency Virus Type 1 Variants Selected for Resistance to Protease Inhibitors In Vivo", J. Virol., 72:3300-3306.

Zhang Y, et al, (1997) "Drug Resistance During Indinavir Therapy is Caused by Mutations in the Protease Gene and in its Gag Substrate Cleavage Sites", J Virol 71:6662-6670.

Zhang D, et al, (1994) "Resistance to 2',3'-Dideoxycytidine Conferred by a Mutation in Codon 65 of the Human Immunodeficiency Virus Type 1 Reverse Transcriptase", *Antimicrob Agents Chemother* 38:282-287.

Buckheit, et al. (1995) "Resistance to 1-[(2-hydroxyethoxy)methyl]-6-(phenylthio)thymine Derivatives is Generated by Mutations at Multiple Sites in the HIV-1 Reverse Transcriptase", Virology 210(1):186-193.

Esnouf, et al. (1997) "Unique Features in the Structure of the Complex Between HIV-1 Reverse Transcriptase and the bis(hetroaryl)piperazine (BHAP) U-90152 Explain Resistance Mutations for this Nonnucleoside Inhibitor", PNAS 94(8) 3984-3989.

Fan al. 1995 "Mechanism of Resistance to U-90152S and Sensitization to L-697, 661 by a Proline to Leucine Change at Residue 236 of Human Immunodeficiency Virus Type-1 (HIV-1) Reverse Transcriptase", FEBS Letters 359(2-3): 233-238.

Kanki, et al. (1997) "Virology of HIV-1 and HIV-2: Implications for Africa", AIDS 11(Supp. B): S33-S42.

Mellors, et al. (1995) "Mutations in HIV-1 Reverse Transcriptase and Protease Associated with Drug Resistance", International Antiviral News vol. 3: 8-13.

Romero, et al. (1996) "Targeting Delavirdine/Atevirdine Resistant HIV-1: Identification of Piperidine-Containing bis(heteroaryl) piperazines as Broad Spectrum HIV-1 Reverse Transcriptase Inhibitors", Journal of Medicinal Chemistry 33(19) 3769-3789.

Salomon, et al. (2000) "Prevalence of HIV-1 Resistant to Antiretroviral Drugs in 81 Individuals Newly Infected By Sexual Contact or Injecting Drug Use", *AIDS* (London, England) 14(2): F17-F23.

* cited by examiner

METHOD OF ASSESSING THE EFFECTIVENESS OF A NON-NUCLEOSIDE REVERSE TRANSCRIPTASE INHIBITOR (NNRTI) ON A HUMAN IMMUNODEFICIENCY VIRUS TYPE 1 (HIV-1)-INFECTED PATIENT

This is a divisional of application Ser. No. 09/320,299 filed May 26, 1999, now U.S. Pat. No. 7,037,644 which claims the benefit of U.S. Provisional Application No. 60/086,834, filed May 26, 1998, and U.S. Provisional Application No. 60/124,090, filed Mar. 12, 1999, the contents of which are each hereby incorporated by reference into this application.

Throughout this application, various references are referred to within parenthesis. Disclosures of these publications in their entireties are hereby incorporated by reference into this application to more fully describe the state of the art to which this invention pertains.

TECHNICAL FIELD

This invention relates to antiretroviral drug susceptibility and resistance tests to be used in identifying effective drug regimens for the treatment of human immunodeficiency virus (HIV) infection and acquired immunodeficiency syndrome (AIDS). The invention further relates to the means and methods of monitoring the clinical progression of HIV infection and its response to antiretroviral therapy using phenotypic or genotypic susceptibility assays. The invention also relates to novel vectors, host cells and compositions for carrying out phenotypic susceptibility tests. The invention further relates to the use of various genotypic methodologies to identify patients whose infection has become resistant to a particular antiretroviral drug regimen. This invention also relates to the screening of candidate antiretroviral drugs for their capacity to inhibit viruses, selected viral sequences and/or viral proteins. More particularly, this invention relates to the determination of non-nucleoside reverse transcriptase inhibitor resistance using phenotypic susceptibility tests and/or genotypic tests.

BACKGROUND OF THE INVENTION

HIV infection is characterized by high rates of viral turnover throughout the disease process, eventually leading to CD4 depletion and disease progression. Wei X, Ghosh S K, Taylor M E, et al. (1995) *Nature* 343, 117-122 and Ho D D, Naumann A U, Perelson A S, et al. (1995) *Nature* 373, 123-126. The aim of antiretroviral therapy is to achieve substantial and prolonged suppression of viral replication. Achieving sustained viral control is likely to involve the use of sequential therapies, generally each therapy comprising combinations of three or more antiretroviral drugs. Choice of initial and subsequent therapy should, therefore, be made on a rational basis, with knowledge of resistance and cross-resistance patterns being vital to guiding those decisions. The primary rationale of combination therapy relates to synergistic or additive activity to achieve greater inhibition of viral replication. The tolerability of drug regimens will remain critical, however, as therapy will need to be maintained over many years.

In an untreated patient, some $10^{10}$ new viral particles are produced per day. Coupled with the failure of HIV reverse transcriptase (RT) to correct transcription errors by exonucleolytic proofreading, this high level of viral turnover results in $10^4$ to $10^{10}$ mutations per day at each position in the HIV genome. The result is the rapid establishment of extensive genotypic variation. While some template positions or base pair substitutions may be more error prone (Mansky L M, Temin H M (1995) *J Virol* 69, 5087-5094) (Schinazi R F, Lloyd R M, Ramanathan C S, et al. (1994) *Antimicrob Agents Chemother* 38, 268-274), mathematical modeling suggests that, at every possible single point, mutation may occur up to 10,000 times per day in infected individuals.

For antiretroviral drug resistance to occur, the target enzyme must be modified while preserving its function in the presence of the inhibitor. Point mutations leading to an amino acid substitution may result in change in shape, size or charge of the active site, substrate binding site or surrounding regions of the enzyme. Mutants resistant to antiretroviral agents have been detected at low levels before the initiation of therapy. (Mohri H, Singh M K, Ching W T W, et al. (1993) *Proc Natl Acad Sci USA* 90, 25-29) (Nájera I, Richman D D, Olivares I, et al. (1994) *AIDS Res Hum Retroviruses* 10, 1479-1488) (Nájera I, Holguin A, Quiñones-Mateu E, et al. (1995) *J Virol* 69, 23-31). However, these mutant strains represent only a small proportion of the total viral load and may have a replication or competitive disadvantage compared with wild-type virus. (Coffin J M (1995) *Science* 267, 483-489). The selective pressure of antiretroviral therapy provides these drug-resistant mutants with a competitive advantage and thus they come to represent the dominant quasispecies (Frost S D W, McLean A R (1994) *AIDS* 8, 323-332) (Kellam P, Boucher C A B, Tijnagal J M G H (1994) *J Gen Virol* 75, 341-351) ultimately leading to drug resistance and virologic failure in the patient.

Non-Nucleoside Reverse Transcriptase Inhibitors

Non-nucleoside reverse transcriptase inhibitors (NNRTIs) are a chemically diverse group of compounds which are potent inhibitors of HIV-1 RT in vitro. These compounds include pyridinone derivatives, bis(heteroaryl)piperazines (BHAPs) such as delavirdine and atevirdine, the dipyridodiazepinone nevirapine, the thymine derivative groups TSAO and HEPT, an α-anilino phenylacetamides (α-APA) compound loviride, and the quinoxaline-class inhibitors such as (HBY-097), the benzodiazepin-one and thione (TIBO) compounds and the pyridinone derivatives (L-697,661). For overviews see (DeClercq E. (1996) *Rev Med Virol* 6, 97-117) (Emini E A (1996) *Antiviral Drug Resistance*, ed. D D Richman, John Wiley & Sons, Ltd. High-level resistance to individual compounds appears to develop rapidly, often within a few weeks of initiating monotherapy, frequently involving only single-point mutations and in many cases leading to considerable cross-resistance to other NNRTIs. Most mutations reported occur in the codon groups 100-108 and 181-190 which encode for the two β-sheets adjacent to the catalytic site of the RT enzyme (Kohlstaedt L A, Wang J, Friedman J M, et al. (1992) *Science* 256, 1783-90). The NNRTI binding pocket, as it has been described, is a hydrophobic non-substrate binding region of RT where these agents directly interact with RT. They inhibit activity by interfering with mobility of the 'thumb' subdomain, or disrupting the orientation of conserved aspartic acid side chains essential for catalytic activity (D'Aquilla R T. (1994) *Clin Lab Med* 14, 393-423) (Arnold E., Ding J., Hughes S H, et al. (1995) *Curr Opin Struct Biol* 5, 27-38).

Mutations conferring reduced susceptibility to nevirapine have been described at codons 98, 100, 103, 106, 108, 181, 188 and 190 (Richman D D, Havlir D, Corbeil J. (1994) *J Virol* 68, 1660-1666). The most frequently selected variant during nevirapine monotherapy is a Tyr181_Cys (Y181C) mutation which results in a 100-fold reduction in sensitivity to this agent, with reduced susceptibility to the pyridinone derivatives L-696,229 and L-697,661 (Arnold, Ibid). TSAO also has limited activity in the presence of the 181 mutation, but maintains activity in the presence of mutations at codons 100 and 103 and in vitro selects for a unique mutation, GLU138_Lys (E138K), in the region where it most closely interacts with RT (Richman D D, Ibid) (Richman D D, Shih C-K, Lowy I, et al. (1991) *Proc Natl Acad Sci USA* 88, 11241-11245).

Resistance to loviride when used as monotherapy develops in most patients by week 24. It has been mapped to a range of codons 100-110; 181-190), most commonly codon 103 (Staszewski S, Miller V, Kober A, et al. (1996) *Antiviral Ther* 1, 42-50). During combination therapy using loviride with zidovudine or zidovudine plus lamivudine, variants at codons 98 and 103 were the most frequent mutations detected at 24 weeks (Staszewski S, Miller V, Rehmet S, et al. (1996) *AIDS* 10, F1-7).

Although the 101, 103 and 181 mutations also confer cross-resistance to BHAPs. (Balzarini J, Karlsson A, Pérez-Pérez M-J, et al. (1992) *Virology* 192, 246-253) the characteristic P236L substitution selected for by these agents in vitro appears to sensitize RT to some other NNRTIs, reducing the IC50 for nevirapine, for example, 7- to 10-fold, without influencing sensitivity to nucleoside analogues (Staszewski S, Ibid). This mutation at codon 236 has not been observed in clinical isolates during atevirdine therapy, although other resistance-conferring mutations at codons 103 and 181 have been reported during monotherapy as well as at codons 101, 188, 233 and 238 during combination therapy with zidovudine.

While HBY-097 may initially select for a mutation at codons 190 in vitro, further passage consistently selects for mutations at RT codon 74 and 75, with some mutant viruses showing decreased sensitivity to didanosine and stavudine, but not zidovudine (Kleim J-P, Rösner M, Winkler I, et al. (1995) *J Acquir Immune Defic Syndr* Suppl 3, 2).

Mutation at codon 181 has been reported to antagonize zidovudine resistance due to the typical 41 and 215 codon mutations, Zhang D, Caliendo A M, Eron J J, et al. (1994) *Antimicrob Agents Chemother* 38, 282-287) suggesting that combination therapy with some NNRTIs and zidovudine may be feasible. Although an HIV mutant with triple resistance to zidovudine, didanosine and nevirapine has been described in vitro, (Larder B A, Kellam P, Kemp S D (1993) *Nature* 365, 451-453) treatment with this triple combination does provide superior immunological and virological responses to treatment with zidovudine plus didanosine alone over a 48-week period in patients with CD4 cell counts <350/mm.

Combination therapy with zidovudine and the pyridinone derivative L-697,661 prevents the appearance of the codon 181 mutation typically selected during monotherapy with this NNRTI, delaying the appearance of high-level resistance to this compound. Changes in susceptibility to zidovudine were not examined in this study. (Staszewski S, Massari F E, Kober A, et al. (1995) *J Infect Dis* 171, 1159-1165). Concomitant or alternating zidovudine therapy does not delay the appearance of resistance during nevirapine therapy; (Richman D D, Ibid) (Nunberg J H, Schleif W A, Boots E J, et al. (1990) *J Virol* 65, 4887-4892) (DeJong M D, Loewenthl M, Boucher C A B, et al. (1994) *J Infect Dis* 169, 1346-1350) (Cheeseman S H, Havlir D, McLaughlin M M, et al. (1995) *J Acquir Immune Defic Syndr* 8, 141-151) however, the 181 mutant is not being observed during combination, the most common change being at codon 190 (Richman D D, Ibid). This suggests that the codon 181 mutation which is antagonistic to zidovudine resistance in vitro is not compatible, or not preferred in vivo, selection favoring other mutations which allow for reduced susceptibility to this NNRTI concomitant with zidovudine resistance.

The rapid development of reduced susceptibility to the NNRTIs suggests limited utility of these agents, particularly as monotherapies, and has led to the modification of these molecules in an attempt to delay the appearance of drug-resistant virus. A 'second generation' NNRTI, the pyridinone derivative L-702,019, demonstrated only a 3-fold change in IC between wild-type and codon 181 mutant HIV-1, and required multiple mutations to engender high-level resistance (Goldman M E, O'Brien J A, Ruffing T L, et al. (1993) *Antimicrob Agents Chemother* 37, 947-949).

It is an object of this invention to provide a drug susceptibility and resistance test capable of showing whether a viral population in a patient is resistant to a given prescribed drug. Another object of this invention is to provide a test that will enable the physician to substitute one or more drugs in a therapeutic regimen for a patient that has become resistant to a given drug or drugs after a course of therapy. Yet another object of this invention is to provide a test that will enable selection of an effective drug regimen for the treatment of HIV infections and/or AIDS. Yet another object of this invention is to provide the means for identifying the drugs to which a patient has become resistant, in particular identifying resistance to non-nucleoside reverse transcriptase inhibitors. Still another object of this invention is to provide a test and methods for evaluating the biological effectiveness of candidate drug compounds which act on specific viruses, viral genes and/or viral proteins particularly with respect to viral drug resistance associated with non-nucleoside reverse transcriptase inhibitors. It is also an object of this invention to provide the means and compositions for evaluating HIV antiretroviral drug resistance and susceptibility. This and other objects of this invention will be apparent from the specification as a whole.

SUMMARY OF THE INVENTION

The present invention relates to methods of monitoring, using phenotypic and genotypic methods, the clinical progression of human immunodeficiency virus infection and its response to antiviral therapy. The invention is also based, in part, on the discovery that genetic changes in HIV reverse transcriptase (RT) which confer resistance to antiretroviral therapy may be rapidly determined directly from patient plasma HIV RNA using phenotypic or genotypic methods. The methods utilize polymerase chain reaction (PCR) based assays. Alternatively, methods evaluating viral nucleic acid of viral protein in the absence of an amplification step could utilize the teaching of this invention to monitor and/or modify antiretroviral therapy. This invention is based in part on the discovery of a mutation at codon 225 either alone or in combination with a mutation at codon 103 of HIV reverse transcriptase in non-nucleoside reverse transcriptase inhibitor (efavirenz) treated patient(s) in which the presence of the mutations correlates with an increase in delavirdine susceptibility and little or no change in nevirapine susceptibility. The mutations were found in plasma HIV RNA after a period of time following initiation of therapy. The development of the mutant at codon 225 in addition to the mutation at codon 103 in HIV RT was found to be an indicator of the development of resistance and ultimately of immunological decline. This invention is based in part on the discovery of a mutation at codon 236 of RT was discovered to occur in non-nucleoside reverse transcriptase inhibitor (NNRTI) treated patients in which the presence of the mutation correlates with decreased susceptibility to delavirdine and no reduction in nevirapine susceptibility. The development of the codon 190 and 103 and/or 101 mutations in HIV RT was found to be an indicator of the development of alterations in phenotypic susceptibility/resistance which has been associated with virologic failure and subsequent immunological decline. This invention is based in part on the discovery of a mutation at codon 190 either alone or in combination with a mutation at codon 103 and/or 101 of HIV reverse transcriptase in non-nucleoside reverse transcriptase inhibitor (efavirenz) treated patient(s) in which the presence of the mutations correlates with an increase in delavirdine susceptibility and a decrease in nevirapine susceptibility. The mutations were found in plasma HIV RNA after a period of time following initiation of NNRTI therapy. The development of the codon 236 and 103 and/or 181 mutations in HIV RT was found to be an indicator of the development of alterations in phenotypic susceptibility/resistance which has been associated with virologic failure and subsequent immunological decline.

This invention is based in part on the discovery of a mutation at codon 230 either alone or in combination with a mutation at codon 181 of HIV reverse transcriptase in non-nucleoside reverse transcriptase inhibitor (nevirapine) treated patient(s) in which the presence of the mutations correlates with a significant decrease in both delavirdine and nevirapine susceptibility. The mutations were found in plasma HIV RNA after a period of time following initiation of NNRTI therapy. The development of the codon 230 and 181 mutations in HIV RT was found to be an indicator of the development of alterations in phenotypic susceptibility/resistance which has been associated with virologic failure and subsequent immunological decline. This invention is based in part on the discovery of a mutation at codon 181 of HIV reverse transcriptase in non-nucleoside reverse transcriptase inhibitor (nevirapine) treated patient(s) in which the presence of the mutation correlates with a moderate decrease in delavirdine susceptibility and a significant decrease in nevirapine susceptibility and no change in efavirenz susceptibility. The mutation was found in plasma HIV RNA after a period of time following initiation of NNRTI therapy. The development of the codon 181 mutation in HIV RT was found to be an indicator of the development of alterations in phenotypic susceptibility/resistance which has been associated with virologic failure and subsequent immunological decline. This invention is based in part on the discovery of a mutation at codon 188 of HIV reverse transcriptase in non-nucleoside reverse transcriptase inhibitor (efavirenz) treated patient(s) in which the presence of the mutation correlates with a slight decrease in delavirdine susceptibility and a substantial decrease in nevirapine susceptibility. The mutation was found in plasma HIV RNA after a period of time following initiation of NNRTI therapy. The development of the codon 188 mutation in HIV RT was found to be an indicator of the development of alterations in phenotypic susceptibility/resistance which has been associated with virologic failure and subsequent immunological decline. This invention is based in part on the discovery of a mutation at codon 188 of HIV reverse transcriptase in patient(s) with no previously reported exposure to non-nucleoside reverse transcriptase inhibitors in which the presence of the mutations correlates with a moderate decrease in delavirdine susceptibility and a substantial decrease in nevirapine susceptibility and a moderate decrease in efavirenz susceptibility. The mutation was found in plasma HIV RNA after a period of time following initiation of anti-retroviral therapy. The development of the codon 138 and 188 mutations in HIV RT was found to be an indicator of the development of alterations in phenotypic susceptibility/resistance which has been associated with virologic failure and subsequent immunological decline. This invention is based in part on the discovery of a mutation at codon 98 of HIV reverse transcriptase in patient(s) with no previously reported exposure to non-nucleoside reverse transcriptase inhibitors in which the presence of the mutation correlates with slight decrease in delavirdine, nevirapine and efavirenz susceptibility. The mutation was found in plasma HIV RNA after a period of time following initiation of anti-retroviral therapy. The development of the codon 98 mutation in HIV RT was found to be an indicator of the development of alterations in phenotypic susceptibility/resistance which has been associated with virologic failure and subsequent immunological decline.

This invention is based in part on the discovery of a mutation at codon 98 either alone or in combination with a mutation at codon 190 of HIV reverse transcriptase in patient(s) whose anti-retroviral treatment was unknown in which the presence of the mutations correlates with an increase in delavirdine susceptibility and substantial decrease in both nevirapine and efavirenz susceptibility. The mutations were found in plasma HIV RNA. The development of the mutant at codon 98 in addition to the mutation at codon 190 in HIV RT was found to be an indicator of the development of resistance and ultimately of immunological decline. This invention is based in part on the discovery of a mutation at codon 181 either alone or in combination with a mutation at codon 98 of HIV reverse transcriptase in non-nucleoside reverse transcriptase inhibitor (delavirdine) treated patient(s) in which the presence of the mutations correlates with a significant decrease in delavirdine susceptibility and a substantial decrease in efavirenz susceptibility. The mutations were found in plasma HIV RNA after a period of time following initiation of therapy. The development of the mutant at codon 98 in addition to the mutation at codon 181 in HIV RT was found to be an indicator of the development of resistance and ultimately of immunological decline. This invention is based in part on the discovery of a mutation at codon 101 either alone or in combination with a mutation at codon 190, for example 190s of HIV reverse transcriptase in non-nucleoside reverse transcriptase inhibitor (efavirenz) treated patient(s) in which the presence of the mutations correlates with no change in delavirdine susceptibility and a substantial decrease in both nevirapine and efavirenz susceptibility. The mutations were found in plasma HIV RNA after a period of time following initiation of therapy. The development of the mutant at codon 101 in addition to the mutation at codon 190, for example 190s in HIV RT was found to be an indicator of the development of resistance and ultimately of immunological decline. This invention is based in part on the discovery of a mutation at codon 108 of HIV reverse transcriptase in patient(s) with no previously reported exposure to non-nucleoside reverse transcriptase inhibitor in which the presence of the mutation correlates with no change in delavirdine susceptibility and a slight decrease in nevirapine susceptibility and no change in efavirenz susceptibility. The mutation was found in plasma HIV RNA after a period of time following initiation of anti-retroviral therapy. The development of the codon 108 mutation in HIV RT was found to be an indicator of the development of alterations in phenotypic susceptibility/resistance which has been associated with virologic failure and subsequent immunological decline.

This invention is based in part on the discovery of a mutation at codon 101 either alone or in combination with a mutation at codon 103 and/or 190 of HIV reverse transcriptase in patients with no previously reported exposure to non-nucleoside reverse transcriptase inhibitors in which the presence of the mutations correlates with changes in delavirdine, nevirapine and efavirenz susceptibility. Specifically, the presence of mutations at 101 and 190, for example 190A, correlates with no change in delavirdine susceptibility and a substantial decrease in nevirapine susceptibility and a significant decrease in efavirenz susceptibility. The presence of mutations at 103 and 190 correlates with a moderate decrease in delavirdine susceptibility, a substantial decrease in nevirapine susceptibility and a significant decrease in efavirenz susceptibility. The mutations were found in plasma HIV RNA after a period of time following initiation of anti-retroviral therapy. The development of the codon 101 and 103 and/or 190 mutations in HIV RT was found to be an indicator of the development of alterations in phenotypic susceptibility/resistance which has been associated with virologic failure and subsequent immunological decline. This invention is based in part on the discovery of a mutation at codon 106 either alone or in combination with a mutation at codon 189 and/or 181 and 227 of HIV reverse transcriptase in non-nucleoside reverse transcriptase inhibitor (nevirapine) treated patient(s) in which the presence of the mutations correlates with changes in delavirdine, nevirapine and efavirenz susceptibility. Specifically, the presence of mutations at 106 and 181 correlates with a significant decrease in delavirdine susceptibility, a substantial decrease in neviradine susceptibility and a slight decrease in efavirenz susceptibility. The presence of mutations at 106 and 189 correlates with a slight decrease in delavirdine susceptibility, a moderate decrease in nevirapine susceptibility and no change in efavirenz susceptibility. The presence of mutations at 106 and 227 correlates with a slight decrease in delavirdine susceptibility, a substantial decrease in nevirapine susceptibility and a slight decrease in efavirenz susceptibility. The presence of mutations at 181 and 227 correlates with an increase in delavirdine susceptibility, a significant decrease in nevirapine susceptibility and an increase in efavirenz susceptibility. The presence of mutations at 106 and 181 and 227 correlates with a moderate decrease in delavirdine susceptibility, a substantial decrease in nevirapine susceptibility and a slight decrease in efavirenz susceptibility. The mutations were found in plasma HIV RNA after a period of time following initiation of NNRTI therapy. The development of the codon 106 and 189 and/or 181 and 227 mutations in HIV RT was found to be an indicator of the development of alterations in phenotypic susceptibility/resistance which has been associated with virologic failure and subsequent immunological decline. This invention is based in part on the discovery of a mutation at codon 103 either alone or in combination with a mutation at codon 100 and/or 188 of HIV reverse transcriptase in non-nucleoside reverse transcriptase inhibitor (nevirapine) created patient(s) in which the presence of the mutations correlates with changes in delavirdine, nevirapine and efavirenz susceptibility. Specifically, the presence of mutations at 103 and 188 correlates with a substantial decrease in delavirdine susceptibility, a substantial decrease in nevirapine susceptibility and a substantial decrease in efavirenz susceptibility. The presence of mutations at 100 and 103 correlates with a substantial decrease in delavirdine susceptibility, a moderate decrease in nevirapine susceptibility and a substantial decrease in efavirenz susceptibility. The presence of mutations at 103 and 100 and 188 correlates with a substantial decrease in delavirdine susceptibility, a substantial decrease in nevirapine susceptibility and a substantial decrease in efavirenz susceptibility. The mutations were found in plasma HIV RNA after a period of time following initiation of NNRTI therapy. The development of the codon 103 and 100 and/or 188 mutations in HIV RT was found to be an indicator of the development of alterations in phenotypic susceptibility/resistance which has been associated with virologic failure and subsequent immunological decline.

In a further embodiment of the invention, PCR based assays, including phenotypic and genotypic assays, may be used to detect mutations at codon 225 in combination with mutations at other codons including 103 of HIV RT which correlate with a specific pattern of resistance to antiretroviral therapies and subsequent immunologic decline. In yet another embodiment of the invention, PCR based assays, including phenotypic and genotypic assays, may be used to detect mutations at codon 236 either alone or in combination with mutations at other codons including 103 and/or 181 of HIV RT which correlate with resistance to antiretroviral therapy and immunologic decline. In yet another embodiment of the invention, PCR based assays, including phenotypic and genotypic assays, may be used to detect mutations at codon 190 (G190S) either alone or in combination with mutation at codon 101 (K101E) of HIV RT which correlates with resistance to antiretroviral therapy and immunologic decline. In still another embodiment of the invention, PCR based assays, including phenotypic and genotypic assays, may be used to detect mutations at codon 190 (G190A) either alone or in combination with mutation at codon 103 (K103N) of HIV RT which correlates with resistance to antiretroviral therapy and immunologic decline. In yet another embodiment of the invention, PCR based assays, including phanotypic and genotypic assays, may be used to detect mutations at codon 230 either alone or in combination with mutation at codon 181 of HIV RT which correlates with resistance to antiretroviral therapy and immunologic decline. In yet another embodiment of the invention, PCR based assays, including phenotypic and genotypic assays, may be used to detect a mutation at codon 181 of HIV RT which correlates with resistance to antiretroviral therapy and immunologic decline. In yet another embodiment of the invention, PCR based assays, including phenotypic and genotypic assays, may be used to detect a mutation at codon 188 of HIV RT which correlates with resistance to antiretroviral therapy and immunologic decline. In yet another embodiment of the invention, PCR based assays, including phenotypic and genotypic assays, may be used to detect mutations at codon 138 either alone or in combination with mutation at codon 188 of HIV RT which correlates with resistance to antiretroviral therapy and immunologic decline. In yet another embodiment of the invention, PCR based assays, including phenotypic and genotypic assays, may be used to detect a mutation at codon 98 of HIV RT which correlates with resistance to antiretroviral therapy and immunologic decline. In yet another embodiment of the invention, PCR based assays, including phenotypic and genotypic assays, may be used to detect mutations at codon 98 either alone or in combination with mutation at codon 190 of HIV RT which correlates with resistance to antiretroviral therapy and immunologic decline. In yet another embodiment of the invention, PCR based assays, including phenotypic and genotypic assays, may be used to detect mutations at codon 181 either alone or in combination with mutation at codon 98 of HIV RT which correlates with resistance to antiretroviral therapy and immunologic decline. In yet another embodiment of the invention, PCR based assays, including phenotypic and genotypic assays, may be used to detect mutations at codon 101 either alone or in combination with mutation at codon 190, for example 190s of HIV RT which correlates with resistance to antiretroviral therapy and immunologic decline. In yet another embodiment of the invention, PCR based assays, including phenotypic and genotypic assays, may be used to detect a mutation at codon 108 of HIV RT which correlates with resistance to antiretroviral therapy and immunologic decline. In yet another embodiment of the invention, PCR based assays, including phenotypic and genotypic assays, may be used to detect mutations at codon 101 either alone or in combination with mutations at codon 103 and/or 190 of HIV RT which correlates with resistance to antiretroviral therapy and immunologic decline. In yet another embodiment of the invention, PCR based assays, including phenotypic and genotypic assays, may be used to detect mutations at codon 106 either alone or in combination with mutations at codon 189 and/or 181 and 227 of HIV RT which correlates with resistance to antiretroviral therapy and immunologic decline. In yet another embodiment of the invention, PCR based assays, including phenotypic and genotypic assays, may be used to detect mutations at codon 188 either alone or in combination with mutation at codon 100 and/or 103 of HIV RT which correlates with resistance to antiretroviral therapy and immunologic decline. Once mutations at codon 225 and 103 have been detected in a patient undergoing NNRTI antiretroviral therapy, an alteration in the therapeutic regimen must be considered. Similarly, once mutations at codon 236 and/or 103 and/or 181 have been detected in a patient undergoing certain NNRTI antiretroviral therapy, an alteration in the therapeutic regimen must be considered. Similarly, once mutations at codon 190 and/or 103 and/or 101 have been detected in a patient undergoing certain NNRTI antiretroviral therapy, an alteration in the therapeutic regimen must be considered. Similarly, once mutations at codon 230 and/or 181 have been detected in a patient undergoing certain NNRTI antiretroviral therapy, an alteration in the therapeutic regimen must be considered. Similarly, once a mutation at codon 181 has been detected in a patient undergoing certain NNRTI antiretroviral therapy, an alteration in the therapeutic regimen must be considered. Similarly, once a mutation at codon 188 has been detected in a patient undergoing certain NNRTI antiretroviral therapy, an alteration in the therapeutic regimen must be considered. Similarly, once mutations at codon 13 8 and/or 188 have been detected in a patient undergoing certain NNRTI antiretroviral therapy, an alteration in the therapeutic regimen must be considered. Similarly, once a mutation at codon 98 has been detected in a patient undergoing certain NNRTI antiretroviral therapy, an alteration in the therapeutic regimen must be considered. Similarly, once mutations at codon 98 and/or 190 have been detected in a patient undergoing certain NNRTI antiretroviral therapy, an alteration in the therapeutic regimen must be considered. Similarly, once mutations at codon 181 and/or 98 have been detected in a patient undergoing certain NNRTI antiretroviral therapy, an alteration in the therapeutic regimen must be considered. Similarly, once mutations at codon 101 and/or 190, for example 190S, have been detected in a patient undergoing certain NNRTI antiretroviral therapy, an alteration in the therapeutic regimen must be considered. Similarly, once a mutation at codon 108 has been detected m a patient undergoing certain NNRTI antiretroviral therapy, an alteration in the therapeutic regimen must be considered. Similarly, once mutations at codon 101 and/or 103 and/or 190, for example 190A, have been detected in a patient undergoing certain NNRTI antiretroviral therapy, an alteration in the therapeutic regimen must be considered. Similarly, once mutations at codon 106 and/or 189 and/or 181 and/or 227 have been detected in a patient undergoing certain NNRTI antiretroviral therapy, an alteration in the therapeutic regimen must be considered. Similarly, once mutations at codon 188 and/or 100 and/or 103 have been detected in a patient undergoing certain NNRTI antiretroviral therapy, an alteration in the therapeutic regimen must be considered. The timing at which a modification of the therapeutic regimen should be made, following the assessment of the antiretroviral therapy using PCR based assays, may depend on several factors including the patient's viral load, CD4 count, and prior treatment history.

In another aspect of the invention there is provided a method for assessing the effectiveness of a non-nucleoside reverse transcriptase antiretroviral drug comprising: (a) introducing a resistance test vector comprising a patient-derived segment and an indicator gene into a host cell; (b) culturing the host cell from step (a); (c) measuring expression of the indicator gene in a target host cell wherein expression of the indicator gene is dependent upon the patient-derived segment; and (d) comparing the expression of the indicator gene from step (c) with the expression of the indicator gene measured when steps (a) (c) are carried out in the absence of the NNRTI anti-HIV drug, wherein a test concentration of the NNRTI, anti-HIV drug is presented at steps (a) (c); at steps (b) (c); or at step (c).

This invention also provides a method for assessing the effectiveness of non-nucleoside reverse transcriptase antiretroviral therapy in a patient comprising: (a) developing a standard curve of drug susceptibility for an NNRTI anti-HIV drug; (b) determining NNRTI anti-HIV drug susceptibility in the patient using the susceptibility test described above; and (c) comparing the NNRTI anti-HIV drug susceptibility in step (b) with the standard curve determined in step (a), wherein a decrease in NNRTI anti-HIV susceptibility indicates development of anti-HIV drug resistance in the patient.

This invention also provides a method for evaluating the biological effectiveness of a candidate HIV antiretroviral drug compound comprising: (a) introducing a resistance test vector comprising a patient-derived segment and an indicator gene into a host cell; (b) culturing the host cell from step (a); (c) measuring expression of the indicator gene in a target host cell wherein expression of the indicator gene is dependent upon the patient-derived segment; and (d) comparing the expression of the indicator gene from step (c) with the expression of the indicator gene measured when steps (a) (c) are carried out in the absence of the candidate anti-viral drug compound, wherein a test concentration of the candidate antiviral drug compound is present at steps (a) (c); at steps (b) (c); or at step (c).

The expression of the indicator gene in the resistance test vector in the target cell is ultimately dependent upon the action of the patient-derived segment sequences. The indicator gene may be functional or non-functional.

In another aspect this invention is directed to antiretroviral drug susceptibility and resistance tests for HIV/AIDS. Particular resistance test vectors of the invention for use in the HIV/AIDS antiretroviral drug susceptibility and resistance test are identified.

In yet another aspect this invention provides for the identification and assessment of the biological effectiveness of potential therapeutic antiretroviral compounds for the treatment of HIV and/or AIDS. In another aspect, the invention is directed to a novel resistance test vector comprising a patient-derived segment further comprising one or more mutations on the RT gene and an indicator gene.

Figure 1:
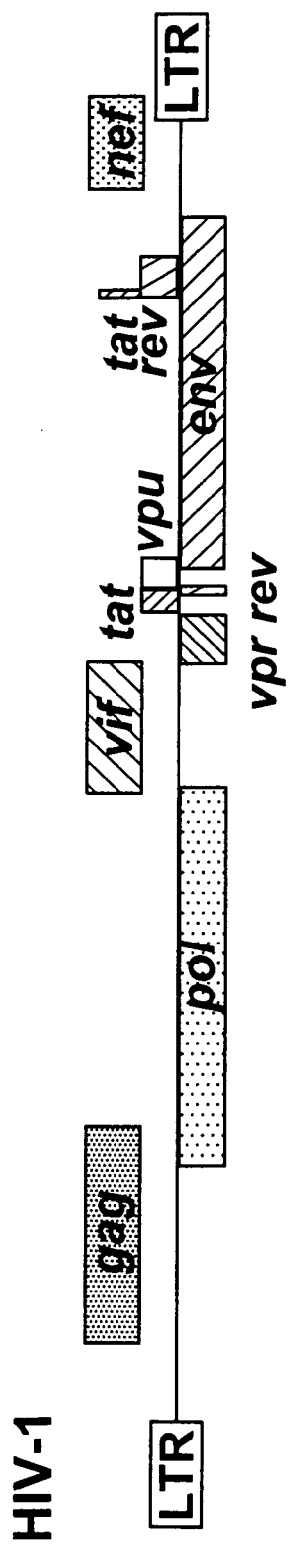
FIG. 1
Figure 1:
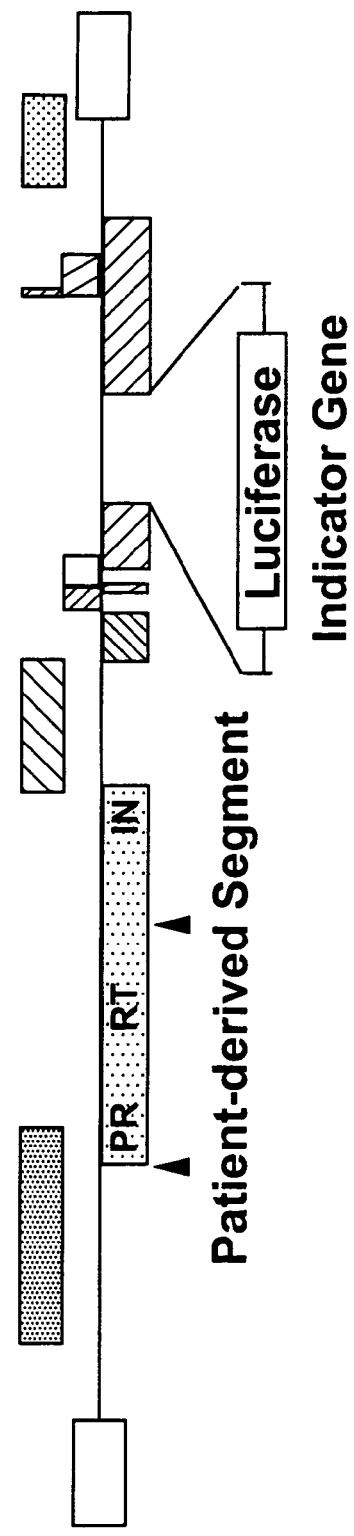
Figure 2:
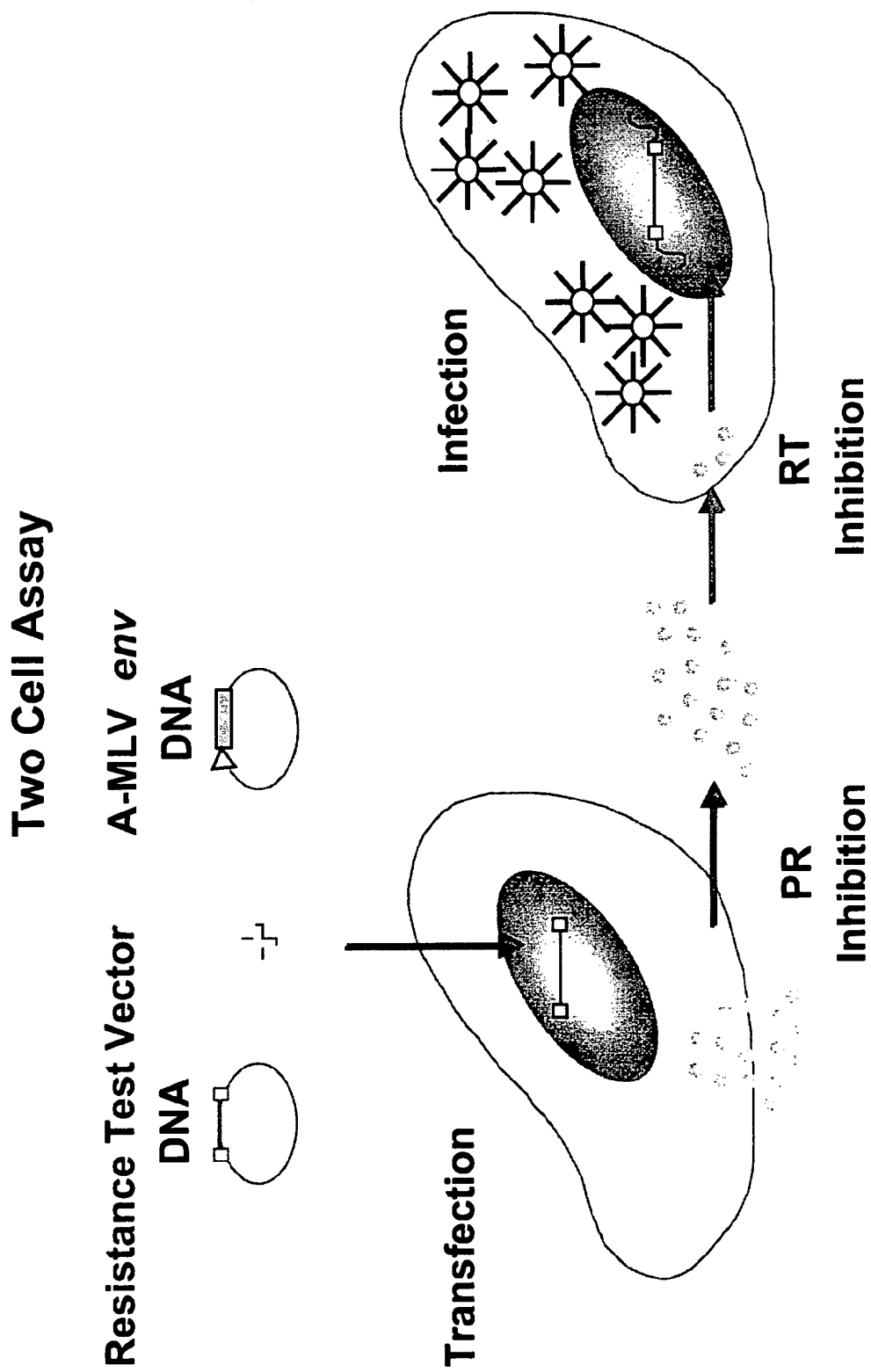

Resistance Test Vector. A diagrammatic representation of the resistance test vector comprising a patient derived segment and an indicator gene.

FIG. 2

Two Cell Assay. Schematic Representation of the Assay. A resistance test vector is generated by cloning the patient-derived segment into an indicator gene viral vector. The resistance test vector is then co-transfected with an expression vector that produces amphotropic murine leukemia virus (MLV) envelope protein or other viral or cellular proteins which enable infection. Pseudotyped viral particles are produced containing the protease (PR) and the reverse transcriptase (RT) gene products encoded by the patient-derived sequences. The particles are then harvested and used to infect fresh cells. Using defective PR and RT sequences it was shown that luciferase activity is dependent on functional PR and RT. PR inhibitors are added to the cells following transfection and are thus present during particle maturation. RT inhibitors, on the other hand, are added to the cells at the time of or prior to viral particle infection. The assay is performed in the absence of drug and in the presence of drug over a wide range of concentrations. The amount of luciferase is determined and the percentage (%) inhibition is calculated at the different drug concentrations tested.

FIG. 3

Examples of phenotypic drug susceptibility profiles. Data are analyzed by plotting the percent inhibition of luciferase activity vs. log concentration. This plot is used to calculate the drug concentration that is required to inhibit virus replication by 50% ($IC_{50}$) or by 95% ($IC_{95}$). Shifts in the inhibition curves towards higher drug concentrations are interpreted as evidence of drug resistance. Three typical curves for a nucleoside reverse transcriptase inhibitor (AZT), a non-nucleoside reverse transcriptase inhibitor (delavirdine), and a protease inhibitor (ritonavir) are shown. A reduction in drug susceptibility (resistance) is reflected in a shift in the drug susceptibility curve toward higher drug concentrations (to the right) as compared to a baseline (pre-treatment) sample or a drug susceptible virus control, such as PNL4-3 or HXB-2, when a baseline sample is not available.

FIG. 4

Phenotypic drug susceptibility and resistance profile: patient 487. A PCR-based phenotypic susceptibility assay was carried out giving the phenotypic drug susceptibility and resistance profile showing increased resistance to both delavirdine and nevirapine. This is an example of the first pattern of NNRTI susceptibility/resistance. Evaluation of this virus from plasma showed HIV reverse transcriptase having mutations at codons 184 (M184V) associated with 3TC resistance and at 103 (K103N) associated with both delavirdine and nevirapine resistance.

FIG. 5

Phenotypic drug susceptibility and resistance profile of site directed reverse transcriptase mutants. A PCR-based phenotypic susceptibility assay was carried out giving the phenotypic drug susceptibility and resistance profile for site directed mutants having mutations at codons 103 and 181 (K103N; Y181C) demonstrating resistance to both delavirdine and nevirapine. The double mutant demonstrates the additive effect of both mutations resulting in a further increase in resistance.

FIG. 6

Phenotypic drug susceptibility and resistance profile: Patient 268. A PCR-based phenotypic susceptibility assay was carried out giving the phenotypic drug susceptibility and resistance profile showing the evaluation of virus from plasma with HIV reverse transcriptase having phenotypic resistance to delavirdine but not nevirapine. This is an example of the second pattern of NNRTI susceptibility/resistance. This patient virus is resistant to all of the protease inhibitors tested and also has significant resistance to AZT and 3TC and shows slight shifts in susceptibility to ddC, ddI, and d4T. Evaluation of this virus from plasma using a PCR and sequencing based genotypic assay showed HIV reverse transcriptase having mutations an codons 103 and 236 (K103N; P236L). The P236L mutation was previously reported to cause delavirdine resistance and nevirapine hypersensitivity (Dueweke T J et al. (1993) *Proc Natl Acad Sci* 90, 4713-4717). However, in this patient sample, while there was delavirdine resistance nevirapine susceptibility was the same as wild type.

FIG. 7

Figure 6A:
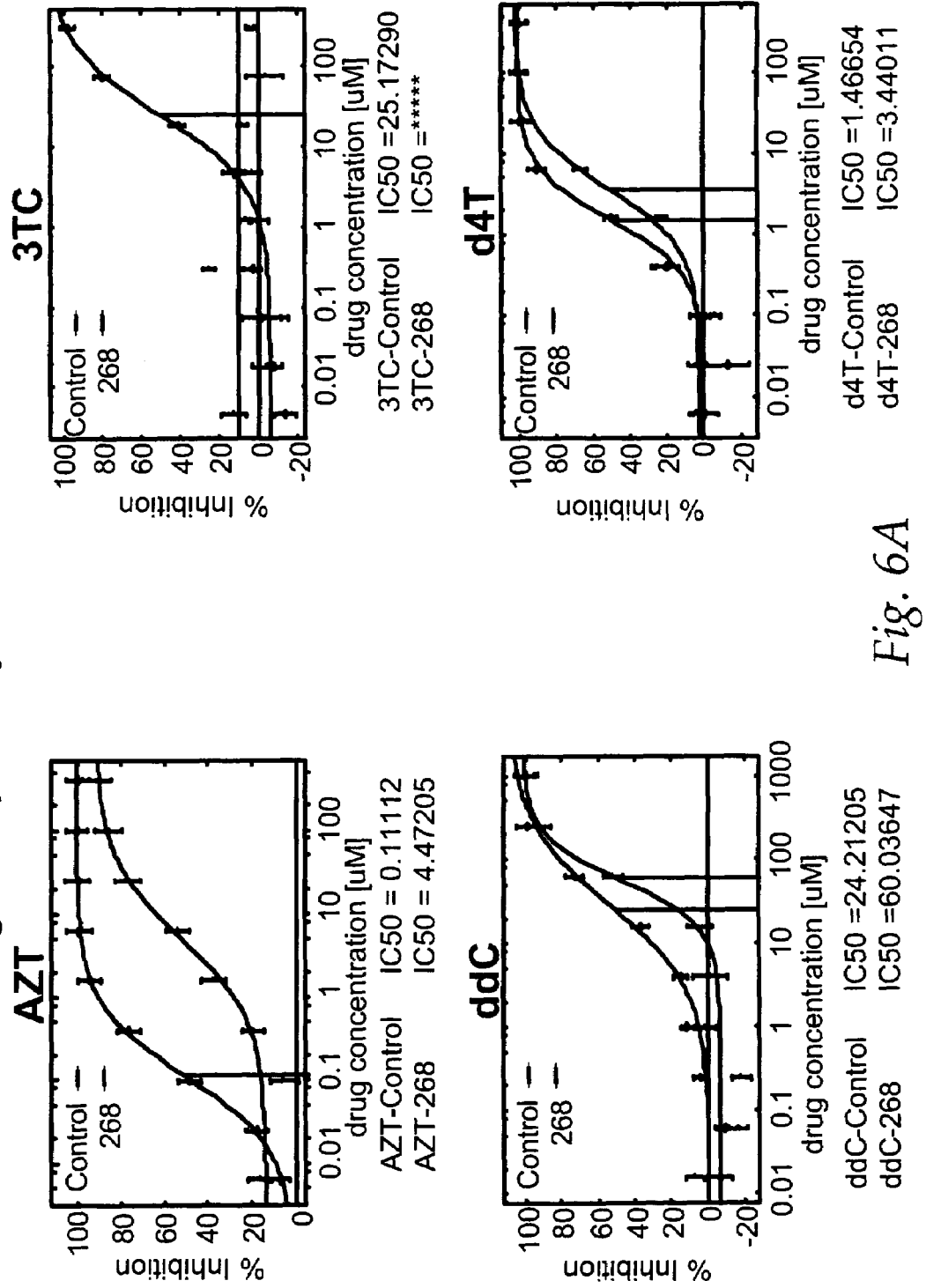
Figure 6B:
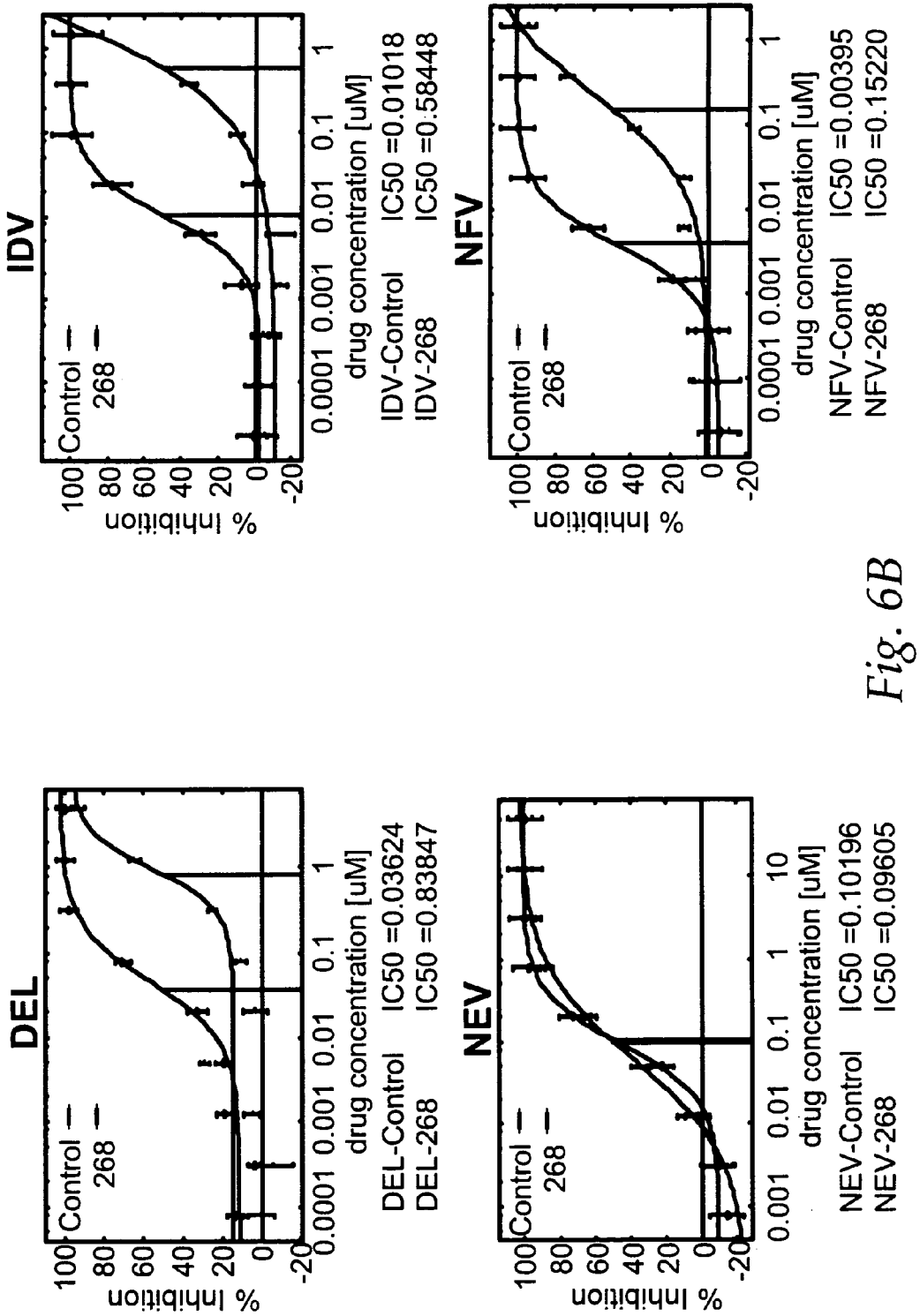
Figure 6C:
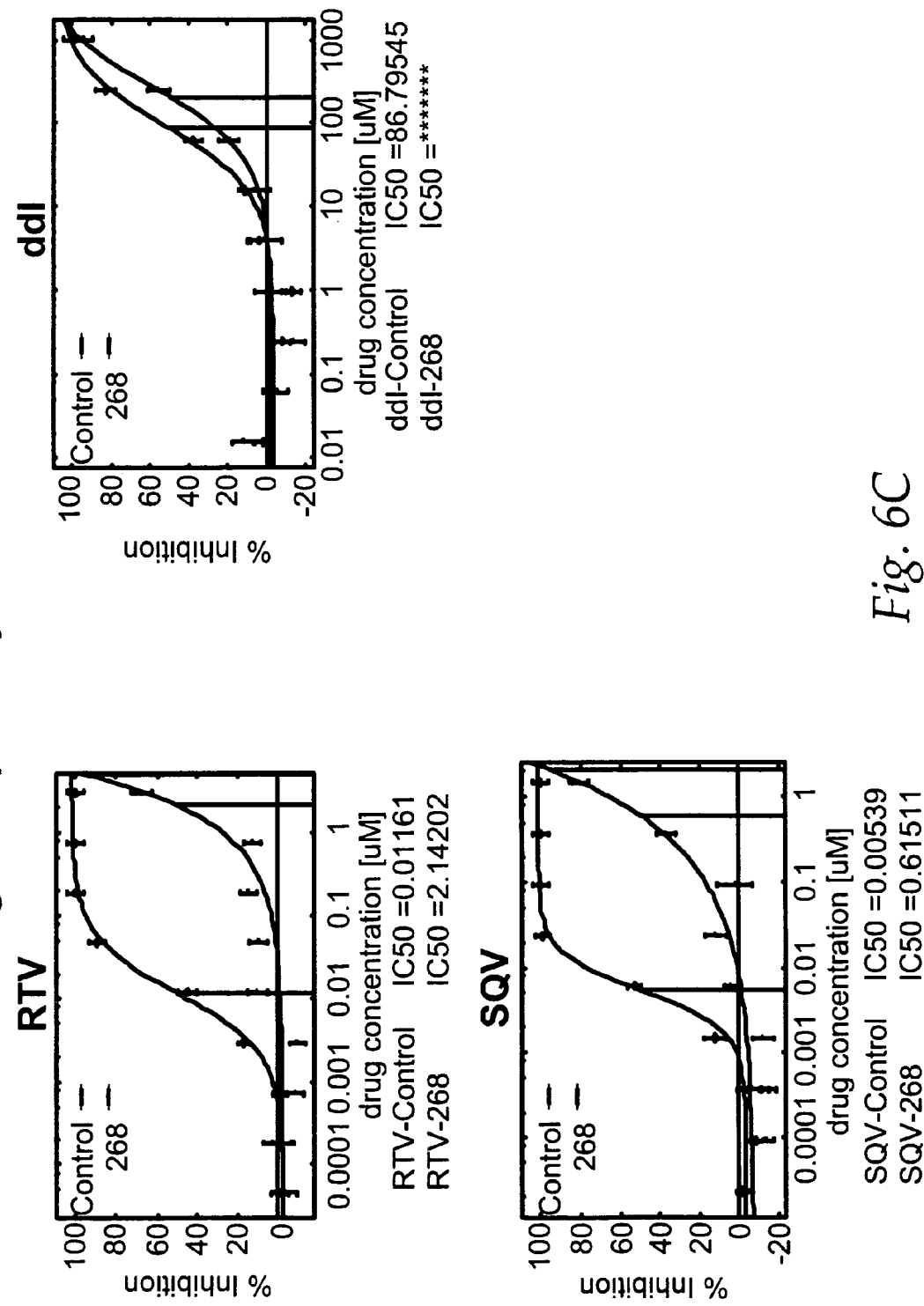
Figure 7A:
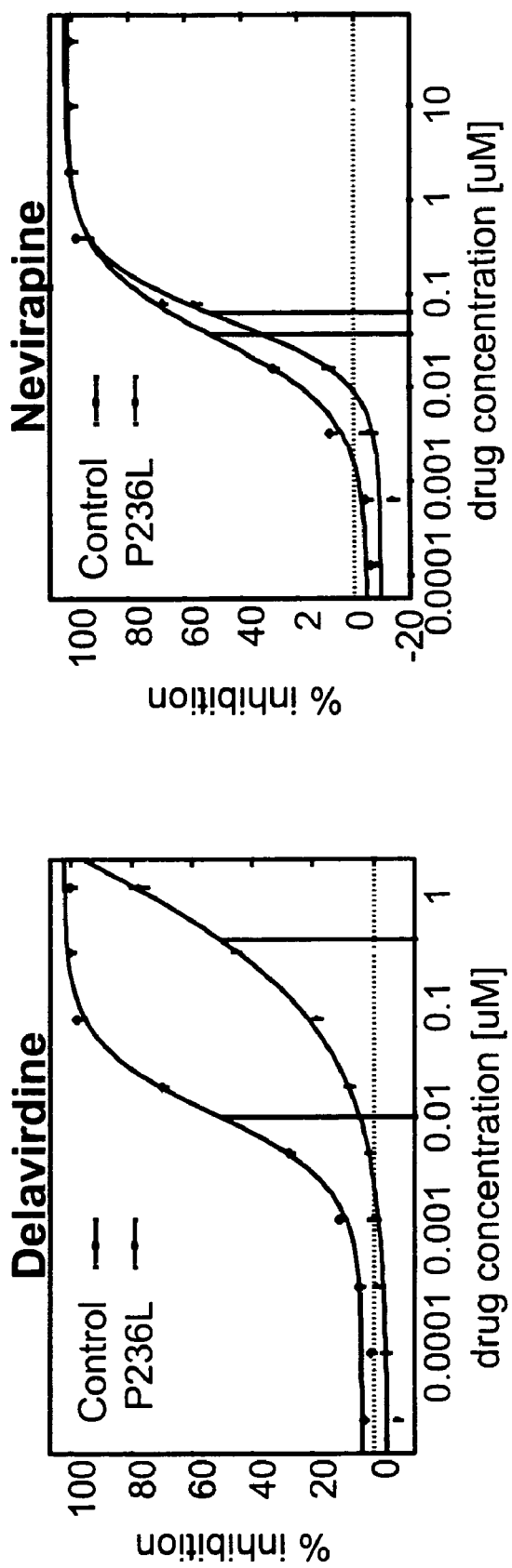
Figure 7B:
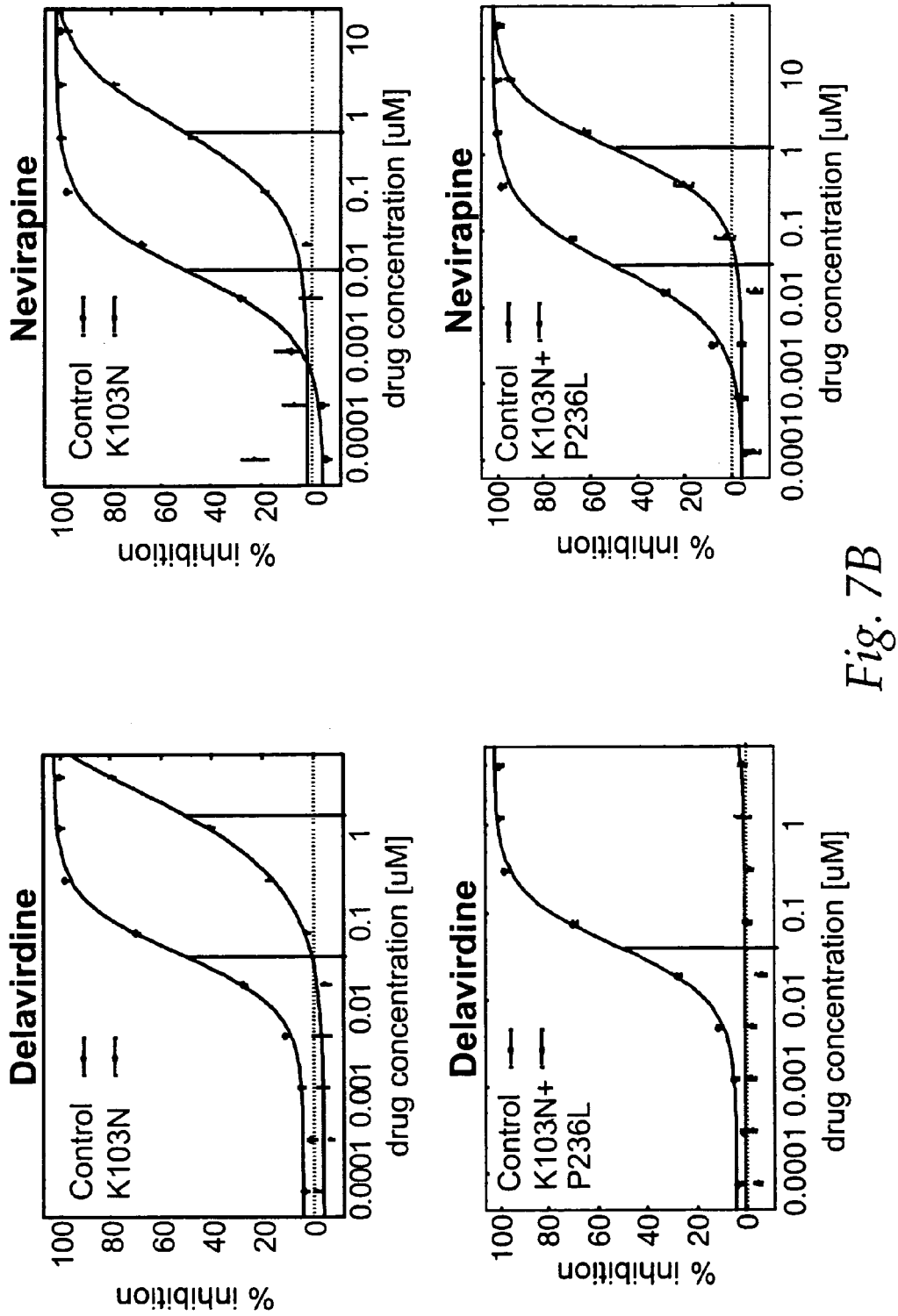
Figure 7C:
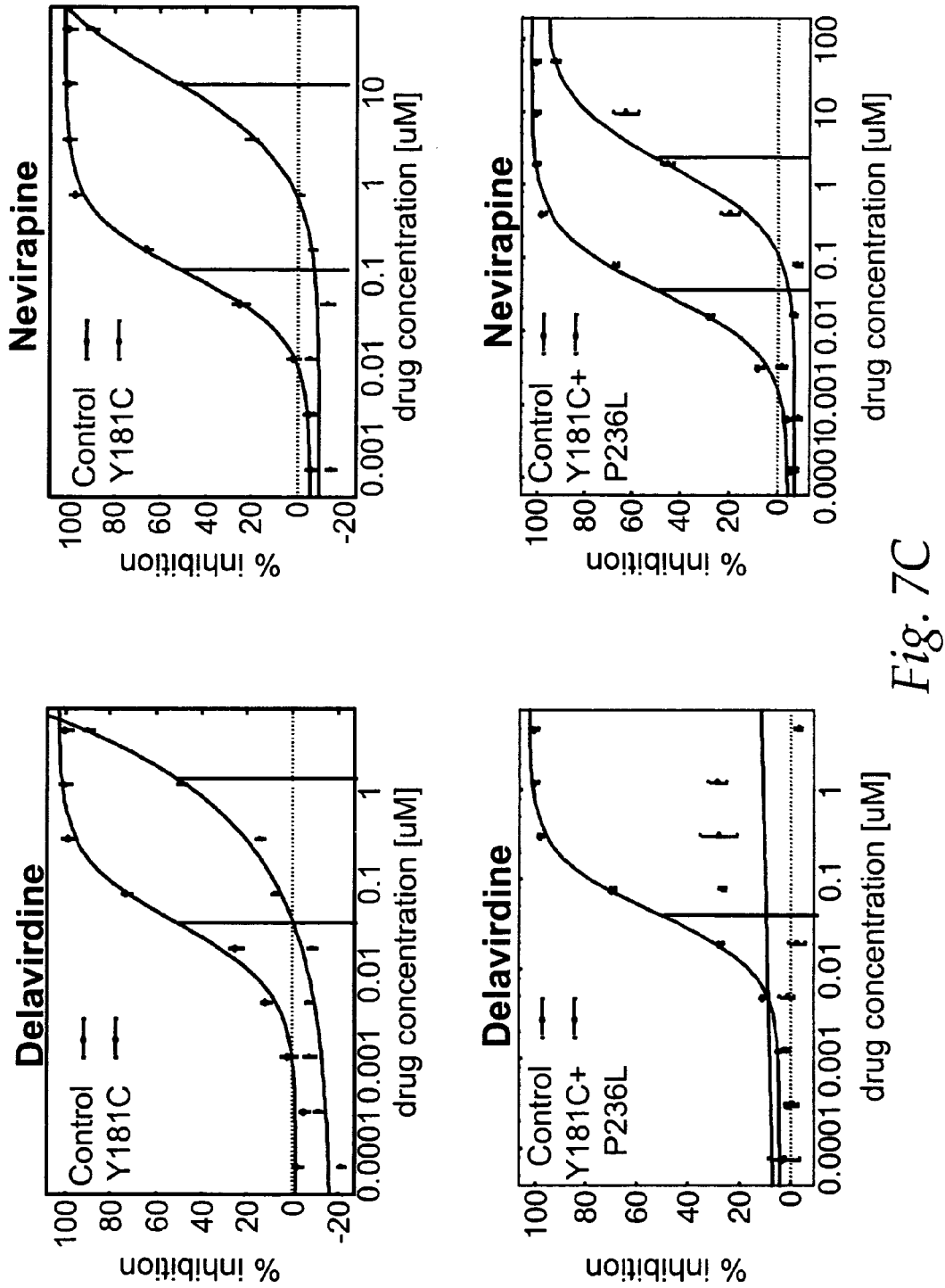

Phenotypic drug susceptibility and resistance profile of site-directed reverse transcriptase mutant (P236L). A PCR-based phenotypic susceptibility assay was carried out giving the phenotypic drug susceptibility and resistance profile showing the susceptibility to delavirdine and nevirapine of the P236L site-directed mutagenesis mutant. This result is identical to that observed in the patient virus sample shown in FIG. 6. The next two panels show the K103N site-directed mutagenesis mutant and the two panels below show the double mutant K103N+P236L. The P236L mutation is additive to the K103N causing severe resistance to delavirdine while having no effect on nevirapine resistance due to K1C3N. The right side of the figure shows a similar result when the P236L mutation is added to the Y181→C mutation.

FIG. 8A

Phenotypic Drug Susceptibility and Resistance Profile: Patients 302. This is one example of the third pattern of NNRTI susceptibility/resistance. Phenotypic analysis of the patient virus demonstrated reduced susceptibility to both delavirdine and nevirapine. This pattern is characterized by a larger reduction of nevirapine susceptibility compared to the reduction of delavirdine susceptibility. Genotypic analysis of the patient virus demonstrated the presence of the RT mutations K103N associated with nevirapine and delavirdine resistance and P225H.

FIG. 8B

Phenotypic Drug Susceptibility and Resistance Profile: Patients 780. This is a second example of the third pattern of NNRTI susceptibility/resistance. Phenotypic analysis of the patient virus demonstrated reduced susceptibility to both delavirdine and nevirapine. This pattern is characterized by a larger reduction of nevirapine susceptibility compared to the reduction of delavirdine susceptibility. Genotypic analysis of the patient virus demonstrated the presence of the RT mutations K103N associated with nevirapine and delavirdine resistance and P225H.

FIG. 8C

Phenotypic Drug Susceptibility and Resistance Profile: Individual Virus Clones of Patient 302. Genotypic analysis of individual virus clones from patient 302 revealed viruses containing the K103N mutation without the P225H mutation (K103N, I135M, R211K) and viruses containing the K103N mutation with the P225H mutation (K103N, P225H). Phenotypic characterization of these virus clones indicates that the P225H mutation reduces the amount delavirdine resistance associated with the K103N mutation (compare bottom panels), but does not alter the amount of nevirapine resistance associated with the K103N mutation (compare top panels).

FIG. 8D

Phenotypic Drug Susceptibility and Resistance Profile: Site Directed Reverse Transcriptase Mutants. Phenotypic characterization of a virus containing the site directed RT mutation P225H indicates that this mutation increases susceptibility to delavirdine, but not nevirapine (compare top panels). Phenotypic characterization of a virus containing the site directed RT mutations P225H plus K103N or P225H plus Y181C indicate that the P225H mutation decreases the amount of delavirdine resistance associated with either K103N or Y181C, but does not decrease the amount of nevirapine resistance associated with K103N or Y181C (compare corresponding middle and bottom panels).

FIG. 9A

Phenotypic Drug Susceptibility and Resistance Profile: Patients 644. This is one example of the fourth pattern of NNRTI susceptibility and resistance. Phenotypic analysis of the patient virus demonstrated by a large reduction in susceptibility to nevirapine, but not delavirdine. Genotypic analysis of the patient virus demonstrated the presence of the RT mutations G190S, as well as the K101E mutation associated with reductions in susceptibility to atevirdine, DMP266, L-697,661 and UC-10,38,57 (Schinazi, Mellors, Larder resistance table).

FIG. 9B

Phenotypic Drug Susceptibility and Resistance Profile: Site Directed Reverse Transcriptase Mutants. Phenotypic characterizations of viruses containing either site directed RT mutations G190A, or G190S indicate that these mutations greatly reduce susceptibility to nevirapine, and slightly increase susceptibility to delavirdine (compare top panels).

DETAILED DESCRIPTION OF THE INVENTION

The present invention relates to methods of monitoring the clinical progression of HIV infection in patients receiving antiretroviral therapy, particularly non-nucleoside reverse transcriptase inhibitor antiretroviral therapy.

In one embodiment, the present invention provides for a method of assessing the effectiveness of antiretroviral therapy of a patient comprising (i) collecting a biological sample from an HIV-infected patient; and (ii) determining whether the biological sample comprises nucleic acid encoding HIV RT having a mutation at one or more positions in the RT. The mutation(s) correlate positively with alterations in phenotypic susceptibility/resistance. In a specific embodiment, the invention provides for a method of assessing the effectiveness of NNRTI antiretroviral therapy of a patient comprising (i) collecting a biological sample from an HIV-infected patient; and (ii) determining whether the biological sample comprises nucleic acid encoding HIV RT having a mutation at codon 225 and 103. This invention established, using a phenotypic susceptibility assay, that mutations at codon 225 either alone or in combination with a mutation at codon 103 of HIV reverse transcriptase are correlated with an increase in delavirdine susceptibility, little or no change in nevirapine susceptibility and little or no change in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 236 and 103 and/or 181. This invention established, using a phenotypic susceptibility assay, that mutations at codon 236 either alone or in combination with a mutation at codon 103 and/or 181 of HIV reverse transcriptase are correlated with a decrease in delavirdine susceptibility (increased resistance) and no change in nevirapine susceptibility. The 236 mutation alone or on a Y181C background has no effect on efavirenz susceptibility but restores a significant portion of the loss of susceptibility caused by a 103N mutation. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 230 and/or 181. This invention established, using a phenotypic susceptibility assay, that mutations at codon 230 either alone or in combination with a mutation at codon 181 of HIV reverse transcriptase are correlated with a significant decrease in delavirdine susceptibility (increased resistance), significant decrease in nevirapine susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon 181. This invention established, using a phenotypic susceptibility assay, that a mutation at codon 181 of HIV reverse transcriptase is correlated with a moderate decrease in delavirdine susceptibility (increased resistance), significant decrease in nevirapine susceptibility and no change in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon 188. This invention established, using a phenotypic susceptibility assay, that a mutation at codon 188 of HIV reverse transcriptase are correlated with a slight decrease in delavirdine susceptibility (increased resistance), a substantial decrease in nevirapine susceptibility and a significant decrease in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 138 and/or 188. This invention established, using a phenotypic susceptibility assay, that mutations at codon 138 either alone or in combination with a mutation at codon 188 of HIV reverse transcriptase are correlated with a moderate decrease in delavirdine susceptibility (increased resistance), a substantial decrease in nevirapine susceptibility and a moderate decrease in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 98. This invention established, using a phenotypic susceptibility assay, that mutations at codon 98 of HIV reverse transcriptase are correlated with a slight decrease in delavirdine susceptibility (increased resistance), a slight decrease in nevirapine susceptibility and a slight decrease in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 98 and/or 190. This invention established, using a phenotypic susceptibility assay, that mutations at codon 98 either alone or in combination with a mutation at codon 190 of HIV reverse transcriptase are correlated with an increase in delavirdine susceptibility (decreased resistance), a substantial decrease in nevirapine susceptibility and a substantial decrease in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 181 and/or 98. This invention established, using a phenotypic susceptibility assay, that mutations at codon 181 either alone or in combination with a mutation at codon 98 of HIV reverse transcriptase are correlated with a significant decrease in delavirdine susceptibility (increased resistance), a substantial decrease in nevirapine susceptibility and a slight decrease in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 101 and/or 190, for example L90S. This invention established, using a phenotypic susceptibility assay, that mutations at codon 101 either alone or in combination with a mutation at codon 190 of HIV reverse transcriptase are correlated with no change in delavirdine susceptibility (wild-type), a substantial decrease in nevirapine susceptibility and a substantial decrease in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 108. This invention established, using a phenotypic susceptibility assay, that a mutation at codon 108 of HIV reverse transcriptase are correlated with no change in delavirdine susceptibility (wild-type), a slight decrease in nevirapine susceptibility and no change in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 101 and 103 and/or 190. This invention established, using a phenotypic susceptibility assay, that mutations at codon 101 either alone or in combination with a mutation at codon 103 and/or 190 of HIV reverse transcriptase are correlated with a either no change (101 and 190) or a moderate decrease (103 and 190, for example 190A) in delavirdine susceptibility (increased resistance), a substantial decrease in nevirapine susceptibility and a significant decrease in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 106 and/or 189 and/or 181 and/or 227. This invention established, using a phenotypic susceptibility assay, that mutations at codon 106 either alone oar in combination with a mutation at codon 189 and/or 181 and/or 227 of HIV reverse transcriptase are correlated with changes in delavirdine, nevirapine and efavirenz susceptibility. Specifically, the presence of mutations at 106 and 181 correlates with a significant decrease in delavirdine susceptibility, a substantial decrease in nevirapine susceptibility and a slight decrease in efavirenz susceptibility. The presence of mutations at 106 and 189 correlates with a slight decrease in delavirdine susceptibility, a moderate decrease in nevirapine susceptibility and no change in efavirenz susceptibility. The presence of mutations at 106 and 227 correlates with a slight decrease in delavirdine susceptibility, a substantial decrease in nevirapine susceptibility and a slight decrease in efavirenz susceptibility. The presence of mutations at 181 and 227 correlates with an increase in delavirdine susceptibility, a significant decrease in nevirapine susceptibility and an increase in efavirenz susceptibility. The presence of mutations at 106 and 181 and 227 correlates with a moderate decrease in delavirdine susceptibility, a substantial decrease in nevirapine susceptibility and a slight decrease in efavirenz susceptibility. In another specific embodiment, the invention provides for a method of evaluating the effectiveness of NNRTI antiretroviral therapy of a patient comprising (i) collecting a biological sample from an HIV-infected patient; and (ii) determining whether the biological sample comprises nucleic acid encoding HIV RT having a mutation at codon(s) 188 and 100 and/or 103. This invention established, using a phenotypic susceptibility assay, that mutations at codon 188 either alone or in combination with a mutation at codon 100 and/or 103 of HIV reverse transcriptase are correlated changes in delavirdine, nevirapine and efavirenz susceptibility. Specifically, the presence of mutations at 103 and 188 correlates with a substantial decrease in delavirdine susceptibility, a substantial decrease in nevirapine susceptibility and a substantial decrease in efavirenz susceptibility. The presence of mutations at 100 and 103 correlates with a substantial decrease in delavirdine susceptibility, a moderate decrease in nevirapine susceptibility and a substantial decrease in efavirenz susceptibility. The presence of mutations at 103 and 100 and 188 correlates with a substantial decrease in delavirdine susceptibility, a substantial decrease in nevirapine susceptibility and a substantial decrease in efavirenz susceptibility. Under the foregoing circumstances, the phenotypic susceptibility/resistance profile and genotypic profile of the HIV virus infecting the patient has been altered reflecting some change in the response to the antiretroviral agent. In the case of NNRTI antiretroviral therapy, the HIV virus infecting the patient may be resistant to one or more but not another of the NNRTIs as described herein. It therefore may be desirable after detecting the mutation, to either increase the dosage of the antiretroviral agent, change to another antiretroviral agent, or add one or more additional antiretroviral agents to the patient's therapeutic regimen. For example, if the patient was being treated with efavirenz (DMP-266) when the 225 mutation arose, the patient's therapeutic regimen may desirably be altered by either (i) changing to a different NNRTI antiretroviral agent, such as delavirdine or nevirapine and stopping efavirenz treatment; or (ii) increasing the dosage of efavirenz; or (iii) adding another antiretroviral agent to the patient's therapeutic regimen. The effectiveness of the modification in therapy may be evaluated by monitoring viral burden such as by HIV RNA copy number. A decrease in HIV RNA copy number correlates positively with the effectiveness of a treatment regimen.

The phrase "correlates positively," as used herein, indicates that a particular result renders a particular conclusion more likely than other conclusions.

Another preferred, non-limiting, specific embodiment of the invention is as follows: A method of assessing the effectiveness of NNRTI therapy of a patient comprising (i) collecting a biological sample from an HIV-infected patient; (ii) amplifying the HIV-encoding RNA in the biological sample by converting the RNA to cDNA and amplifying HIV sequences using HIV primers that result in a PCR product that comprises the RT gene; (iii) performing PCR using primers that result in PCR products comprising wild type or mutant 225 and 103 codons; and (iv) determining, via the products of PCR, the presence or absence of a mutation at codon 225 or 103 or both. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codons 103 and/or 181 and 236; and (iv) determining, via the products of PCR, the presence or absence of a mutation at codon 236 and 103 and/or 181. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 101 and 190 (G190S); and (iv) determining, via the products of PCR, the presence or absence of a mutation at codon 190 (G190S) and 103. Yet another preferred, non-limiting specific embodiment, of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 103 and 190 (G190A); and (iv) determining, via the products of PCR, the presence or absence of a mutation at codon 190 (G190A) and 103. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 230 and 181; and (iv) determining, via the products of PCR, the presence or absence of a mutation at codon 230 and 181. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutation at 181; and (iv) determining, via the products of PCR, the presence or absence of a mutation at codon 181. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutation at codon 188; and (iv) determining, via the products of PCR, the presence or absence of a mutation at codon 188. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 138 and 188; and (iv) determining, via the products of PCR, the presence or absence of a mutation at codon 138 and 188. Yet another preferred, non-limiting specific embodiment, of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutation at codon 98 and (iv) determining, via the products of PCR, the presence or absence of a mutation at codon 98. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sampled by converting the RNA to cDNA and amplifying HIV sequences using HIV primers that result in a PCR product that comprises the RT gene; (iii) performing PCR using primers that result in PCR products comprising the wild type or mutations at codon 98 and 190; and (iv) determining, via the products of PCR, the presence or absence of a mutation at codon 190 and 98. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the XHA to cDNA and amplifying HIV sequences using HIV primers that result in a PCR product that comprises the RT gene; (iii) performing PCR using primers that result in PCR products comprising the wild type or mutations at codon 98 and 181; and (iv) determining, via the products of PCR, the presence or absence of a mutation at codon 98 and 181.

Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the SKA. to cDNA and amplifying HIV sequences using HIV primers that result in a PCR product that comprises the RT gene; (iii) performing PCR using primers that result in PCR products comprising the wild type or mutations at codon 101 and 190; and (iv) determining, via the products of PCR, the presence or absence of a mutation at codon 190, for example 190S and 101.

Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or a mutation at codon 108; and (iv) determining, via the products of PCR, the presence or absence of a mutation at codon 108. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 101 and 103 and 190 and (iv) determining, via the products of PCR, the presence or absence of a mutation at codon 101 and 103 and 190, for example 190A. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 106 and 189 and 181 and 227 and (iv) determining, via the products of PCR, the presence or absence of a mutation at codon 106 and 189 and 181 and 227. Yet another preferred, non-limiting specific embodiment of the invention is as follows: A method of assessing the effectiveness of NNRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 188 and 100 and 103 and (iv) determining, via the products of PCR, the presence or absence of a mutation at codon 188 and 100 and 103.

The presence of the mutation at codon 225 and 103 of HIV RT indicates that the effectiveness of the current or prospective NNRTI therapy may require alteration, since as shown by this invention mutation at codon 103 reduces susceptibility which susceptibility can in part be restored by mutation at codon 225. Using the methods of this invention change in the NNRTI therapy would be indicated. Similarly, using the means and methods of this invention the presence of the mutation at codon 236 and 103 and/or 181 of the HIV RT indicates that the effectiveness of the current or prospective NNRTI therapy has been diminished. Similarly, using the means and methods of this invention the presence of the mutation at codon 190 (G190A) and 103 (K103N) of the HIV RT indicates that the effectiveness of the current or prospective NNRTI therapy has been diminished. Similarly, using the means and methods of this invention the presence of the mutation at codon 190 (G190S) and 101 (K101E) of the HIV RT indicates that the effectiveness of the current or prospective NNRTI therapy baa been diminished. Similarly, using the means and methods of this invention the presence of the mutation at codon 230 and 181 of the HIV RT indicates that the effectiveness of the current or prospective NNRTI therapy has been diminished. Similarly, using the means and methods of this invention the presence of the a mutation at codon 181 of the HIV RT indicates that the effectiveness of the current or prospective NNRTI therapy has been diminished. Similarly, using the means and methods of this invention the presence of the mutation at codon 188 of the HIV RT indicates that the effectiveness of the current or prospective NNRTI therapy has been diminished. Similarly, using the means and methods of this invention the presence of the mutation at codon 138 and 188 of the HIV RT indicates that the effectiveness of the current or prospective NNRTI therapy has been diminished. Similarly, using the means and methods of this invention the presence of the mutation at codon 98 of the HIV RT indicates that the effectiveness of the current or prospective NNRTI therapy has been diminished. Similarly, using the means and methods of this invention the presence of the mutation at codon 98 and 190 of the HIV RT indicates that the effectiveness of the current or prospective NNRTI therapy has been diminished. Similarly, using the means and methods of this invention the presence of the mutation at codon 181 and 98 of the HIV RT indicates that the effectiveness of the current or prospective NNRTI therapy has been diminished. Similarly, using the means and methods of this invention the presence of the mutation at codon 101 and 190, for example 190S, of the HIV RT indicates that the effectiveness of the current or prospective NNRTI therapy has been diminished. Similarly, using the means and methods of this invention the presence of a mutation at codon 108 of the HIV RT indicates that the effectiveness of the current or prospective NNRTI therapy has been diminished. Similarly, using the means and methods of this invention the presence of the mutations at 101 and 103 and 190, for example 190A, of the HIV RT indicates that the effectiveness of the current or prospective NNRTI therapy has been diminished. Similarly, using the means and methods of this invention the presence of the mutation at codon 106 and 189 and 181 and 227 of the HIV RT indicates that the effectiveness of the current or prospective NNRTI therapy has been diminished. Similarly, using the means and methods of this invention the presence of the mutation at codon 188 and 100 and 103 of the HIV RT indicates that the effectiveness of the current or prospective NNRTI therapy has been diminished.

Another preferred, non-limiting, specific embodiment of the invention is as follows: a method of evaluating the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 236 and 103 and/or 181. Using the phenotypic susceptibility assay, it was observed that the presence of the three mutations correlates positively with delavirdine resistance. Using the phenotypic susceptibility assay, it was observed that the presence of the three mutations correlates positively with nevirapine resistance. In another embodiment, the mutated codon 236 of HIV RT encodes leucine (L). In a further embodiment, the reverse transcriptase has a mutation at codon 103, a mutation at codon 181 or a combination thereof in addition to the mutation at codon 236 of HIV RT. In a still further embodiment, the mutated codon 103 encodes an asparagine (N) and the mutated codon at 181 encodes a cysteine (C).

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 225 and 103. Using the phenotypic susceptibility assay, it was observed that the presence of the mutations at codons 225 alone or in combination with a mutation at codon 103 of HIV RT cause an increase in delavirdine susceptibility, while having no effect on nevirapine susceptibility. In yet another embodiment, the mutated codon 225 codes for a histidine.

This invention provides a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 181. Using the phenotypic susceptibility assay it was observed that the presence of mutations at codon 181 correlates positively with a moderate decrease in delavirdine susceptibility and a significant decrease in nevirapine susceptibility and no change in efavirenz susceptibility. In an embodiment, the mutated colon 181 codes for a isoleuecine.

This invention provides a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 188. Using the phenotypic susceptibility assay it was observed that the presence of mutations at colon 188 correlates positively with a slight decrease in delavirdine susceptibility and a substantial decrease in nevirapine susceptibility and significant decrease in efavirenz susceptibility. In an embodiment, the mutated codon 188 codes for a cysteine, histidine, or leucine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 138 and 188. Using the phenotypic susceptibility assay, it was observed that the presence of the mutations at codons 138 alone or in combination with a mutation at codon 188 of HIV RT causes a moderate decrease in delavirdine susceptibility and a substantial decrease in nevirapine susceptibility and a moderate decrease in efavirenz susceptibility. In yet another embodiment, the mutated codon 138 codes for a alanine and codon 188 codes for a leucine.

This invention provides a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 98. Using the phenotypic susceptibility assay it was observed that the presence of mutations at codon 98 correlates positively with a slight decrease in delavirdine susceptibility and a slight decrease in nevirapine susceptibility and a slight decrease in efavirenz susceptibility. In an embodiment, the mutated codon 98 codes for a glycine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 98 and 190. Using the phenotypic susceptibility assay, it was observed that the presence of the mutations at codons 98 alone or in combination with a mutation at codon 190 of HIV RT causes an increase in delavirdine susceptibility and a substantial decrease in nevirapine susceptibility and a substantial decrease in efavirenz susceptibility. In yet another embodiment, the mutated codon 190 codes for a serine and codon 98 codes for a glycine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 181 and 98. Using the phenotypic susceptibility assay, it was observed that the presence of the mutations at codons 181 alone or in combination with a mutation at codon 98 of HIV RT causes a significant decrease in delavirdine susceptibility and a substantial decrease in nevirapine susceptibility and a slight decrease in efavirenz susceptibility. In yet another embodiment, the mutated codon 98 codes for a glycine and codon 181 codes for a cysteine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 101 and 190, for example 190S. Using the phenotypic susceptibility assay, it was observed that the presence of the mutations at codons 101 alone or in combination with a mutation at codon 190 of HIV RT causes no change in delavirdine susceptibility and a substantial decrease in nevirapine susceptibility and a substantial decrease in efavirenz susceptibility. In yet another embodiment, the mutated codon 190 codes for a serine and codon 101 codes for a glutamine acid.

This invention provides a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 108. Using the phenotypic susceptibility assay It was observed that the presence of mutations at codon 108 correlates positively with no change in delavirdine susceptibility and a slight decrease in nevirapine susceptibility and no change in efavirenz susceptibility. in an embodiment, the mutated codon 108 codes for a isoleucine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 101 and 190, for example 190A. Using the phenotypic susceptibility assay, it was observed that the presence of the mutations at codons 101 alone or in combination with a mutation at codon 190 of HIV RT causes no change in delavirdine susceptibility and a substantial decrease in nevirapine susceptibility and a significant decrease in efavirenz susceptibility. In yet another embodiment, the mutated codon 190 codes for a glycine and codon 101 codes for a glutamine acid.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 103 and 190. Using the phenotypic susceptibility assay, it was observed that the presence of the mutations at codons 103 alone or in combination with a mutation at codon 190 of HIV RT causes a moderate decrease in delavirdine susceptibility and a substantial decrease in nevirapine susceptibility and a significant decrease in efavirenz susceptibility. In yet another embodiment, the mutated codon 190 codes for a alanine and codon 103 codes for a asparagine. Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 106 and 181. Using the phonotypic susceptibility assay, it was observed that the presence of the mutations at codons 106 alone or in combination with a mutation at codon 181 of HIV RT causes a significant decrease in delavirdine susceptibility and a substantial decrease in nevirapine susceptibility and a slight decrease in efavirenz susceptibility. In yet another embodiment, the mutated codon 106 codes for a alanine and codon 181 codes for a cysteine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 106 and 189. Using the phenotypic susceptibility assay, it was observed that the presence of the mutations at codons 106 alone or in combination with a mutation at codon 189 of HIV RT causes a slight decrease in delavirdine susceptibility and a moderate decrease in nevirapine susceptibility and no change in efavirenz susceptibility. In yet another embodiment, the mutated codon 189 codes for a leucine and a codon 106 codes for a alanine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 106 and 227. Using the phenotypic susceptibility assay, it was observed that the presence of the mutations at codons 106 alone or in combination with a mutation at codon 227 of HIV RT causes a slight decrease in delavirdine susceptibility and a substantial decrease in nevirapine susceptibility and a slight decrease in efavirenz susceptibility. In yet another embodiment, the mutated codon 227 codes for a leucine and codon 106 codes for a alanine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 181 and 227. Using the phenotypic susceptibility assay, it was observed that the presence of the mutations at codon 181 alone or in combination with a mutation at codon 227 of HIV RT causes an increase in delavirdine susceptibility and a significant decrease in nevirapine susceptibility and an increase in efavirenz susceptibility. In yet another embodiment, the mutated codon 227 codes for a leucine and codon 181 codes for a cysteine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 106 and 181 and 227. Using the phenotypic susceptibility assay, it was observed that the presence of the mutations at codons 106 alone or in combination with a mutation at codon 181 and 227 of HIV RT causes a moderate decrease in delavirdine susceptibility and a substantial decrease in nevirapine susceptibility and a slight decrease in efavirenz susceptibility. In yet another embodiment, the mutated codon 106 codes for a alanine, codon 181 codes for a cysteine and codon 227 codes for a leucine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 103 and 188. Using the phenotypic susceptibility assay, it was observed that the presence of the mutations at codons 103 alone or in combination with a mutation at codon 188 of HIV RT causes a substantial decrease in delavirdine susceptibility and a substantial decrease in nevirapine susceptibility and a substantial decrease in efavirenz susceptibility. In yet another embodiment, the mutated codon 188 codes for a leucine and codon 103 codes for a asparagine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 100 and 103. Using the phenotypic susceptibility assay, it was observed that the presence of the mutations at codons 100 alone or in combination with a mutation at codon 103 of HIV RT causes a substantial decrease in delavirdine susceptibility and a moderate decrease in nevirapine susceptibility and a substantial decrease in efavirenz susceptibility. In yet another embodiment, the mutated codon 100 codes for a isoleucine and codon 103 codes for a asparagine.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at codon 100 and 103 and 188. Using the phenotypic susceptibility assay, it was observed that the presence of the mutations at codons 100 alone or in combination with a mutation at codon 103 and 188 of HIV RT causes a substantial decrease in delavirdine susceptibility and a substantial decrease in nevirapine susceptibility and a substantial decrease in efavirenz susceptibility. In yet another embodiment, the mutated codon 100 codes for a isoleucine, codon 103 codes for a asparagine and codon 188 codes for a leucine.

This invention also provides the means and methods to use the resistance test vector comprising an HIV gene further comprising an NNRTI mutation for drug screening. More particularly, the invention describes the resistance test vector comprising the HIV reverse transcriptase having mutations at codons 225 and 103 for drug screening. The invention also describes the resistance test vector comprising the HIV reverse transcriptase having mutations at codons 236 and 103 and/or 181. The invention also describes the resistance test vector comprising the HIV reverse transcriptase having mutations at codons 190 (G190A) and 103 (K103N). The invention also describes the resistance test vector comprising the HIV reverse transcriptase having mutations at codons 190 (G190S) and 101 (K101E). The invention also describes the resistance test vector comprising the HIV reverse transcriptase having mutations at codons 230 and 181. The invention also describes the resistance test vector comprising the HIV reverse transcriptase having a mutation at codon 181. The invention also describes the resistance test vector comprising the HIV reverse transcriptase having a mutation at codon 188. The invention also describes the resistance test vector comprising the HIV reverse transcriptase having mutations at codons 138 and 188. The invention also describes the resistance test vector comprising the HIV reverse transcriptase having a mutation at 98. The invention also describes the resistance test vector comprising the HIV reverse transcriptase having mutations at codons 98 and 190. The invention also describes the resistance test vector comprising the HIV reverse transcriptase having mutations at codons 181 and 98. The invention also describes the resistance test vector comprising the HIV reverse transcriptase having mutations at codons 101 and 190, for example 190S. The invention also described the resistance test vector comprising the HIV reverse transcriptase having a mutation at codon 108. The invention also describes the resistance teat vector comprising the HIV reverse transcriptase having mutations at codons 101 and 103 and/or 190, for example 190A. The invention also describes the resistance test vector comprising the HIV reverse transcriptase having mutations at codons 106 and 189 and/or 181 and/or 227. The invention also describes the resistance test vector comprising the HIV reverse transcriptase having mutations at codons 188 and 100 and/or 103. The invention further relates to novel vectors, host cells and compositions for isolation and identification of the non-nucleoside HIV-1 reverse transcriptase inhibitor resistance mutant and using such vectors, host cells and compositions to carry out anti-viral drug screening. This invention also relates to the screening of candidate drugs for their capacity to inhibit said mutant.

EXAMPLE 1

Phenotypic Drug Susceptibility and Resistance Test Using Resistance Test Vectors Phenotypic drug susceptibility and resistance tests are carried out using the means and methods described in PCT International Application No. PCT/US97/01609, filed Jan. 29, 1997 which is hereby incorporated by reference.

In these experiments patient-derived segment(s) corresponding to the HIV protease and reverse transcriptase coding regions were either patient-derived segments amplified by the reverse transcription-polymerase chain reaction method (RT-PCR) using viral RNA isolated from viral particles present in the serum of HIV-infected individuals or were mutants of wild type HIV-1 made by site directed mutagenesis of a parental clone of resistance test vector DNA. Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into cDNA. The cDNA was then amplified using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from *Thermus brockianus*, Biometra, Gottingen, Germany)] or a combination of thermostable polymerases as described for the performance of "long PCR" (Barnes, W. M., (1994) Proc. Natl. Acad. Sci, USA 91, 2216-2220) [e.g. Expand High Fidelity PCR System (Taq+Pwo), (Boehringer Mannheim, Indianapolis, Ind.) OR GeneAmp XL PCR kit (Tth+Vent), (Roche Molecular Systems, Inc., Branchburg, N.J.)].

The primers, ApaI primer (PDSApa) and AgeI primer (PDSAge) used to amplify the "test" patient-derived segments contained sequences resulting in ApaI and AgeI recognition sites being introduced into the 5' and 3' termini of the PCR product, respectively as described in PCT International Application No. FCT/US97/01609, filed Jan. 29, 1997.

Resistance test vectors incorporating the "test" patient-derived segments were constructed as described in PCT International Application No. PCT/US97/01609, filed Jan. 29, 1997 using an amplified DNA product of 1.5 kB prepared by RT-PCR using viral RNA as a template and oligonucleotides PDSApa (1) and PDSAge (2) as primers, followed by digestion with ApaI and AgeI or the isoschizimer PINAI. To ensure that the plasmid DNA corresponding to the resultant resistance test vector comprises a representative sample of the HIV viral quasi-species present in the serum of a given patient, many (>100) independent *E. coli* transformants obtained in the construction of a given resistance test vector were pooled and used for the preparation of plasmid DNA.

A packaging expression vector encoding an amphotrophic MuLV 4070A env gene product enables production in a resistance test vector host cell of resistance test vector viral particles which can efficiently infect human target cells. Resistance test vectors encoding all HIV genes with the exception of env were used to transfect a packaging host cell (once transfected the host cell is referred to as a resistance test vector host cell). The packaging expression vector which encodes the amphotrophic MuLV 4070A env gene product is used with the resistance test vector to enable production in the resistance test vector host cell of infectious pseudotyped resistance test vector viral particles.

Resistance tests performed with resistance test vectors were carried out using packaging host and target host cells consisting of the human embryonic kidney cell line 293 (Cell Culture Facility, UC San Francisco, SF, Calif.) or the Jurkat leukemic T-cell line (Arthur Weiss, UC San Francisco, SF, Calif.).

Resistance tests were carried out with resistance test vectors using two host cell types. Resistance test vector viral particles were produced by a first host cell (the resistance test vector host cell) that was prepared by transfecting a packaging host cell with the resistance test vector and the packaging expression vector. The resistance test vector viral particles were then used to infect a second host cell (the target host cell) in which the expression of the indicator gene is measured.

The resistance test vectors containing a functional luciferase gene cassette were constructed and host cells were transfected with the resistance test vector DNA. The resistant test vectors contained patient-derived reverse transcriptase and protease sequences that were either susceptible or resistant to the antiretroviral agents, such as nucleoside reverse transcriptase inhibitors, non-nucleoside reverse transcriptase inhibitors and protease inhibitors. The resistance test vector viral particles produced by transfecting the resistance test vector DNA into host cells, either in the presence or absence of protease inhibitors, were used to infect target host cells grown either in the absence of NRTI or NNRTI or in the presence of increasing concentrations of the drug. The amount of luciferase activity produced in infected target host cells in the presence of drug was compared to the amount of luciferase produced in infected target host cells in the absence of drug. Drug resistance was measured as the amount of drug required to inhibit by 50% the luciferase activity detected in the absence of drug (inhibitory concentration 50%, IC50). The IC50 values were determined by plotting percent drug inhibition vs. log drug concentration.

Figure 3:
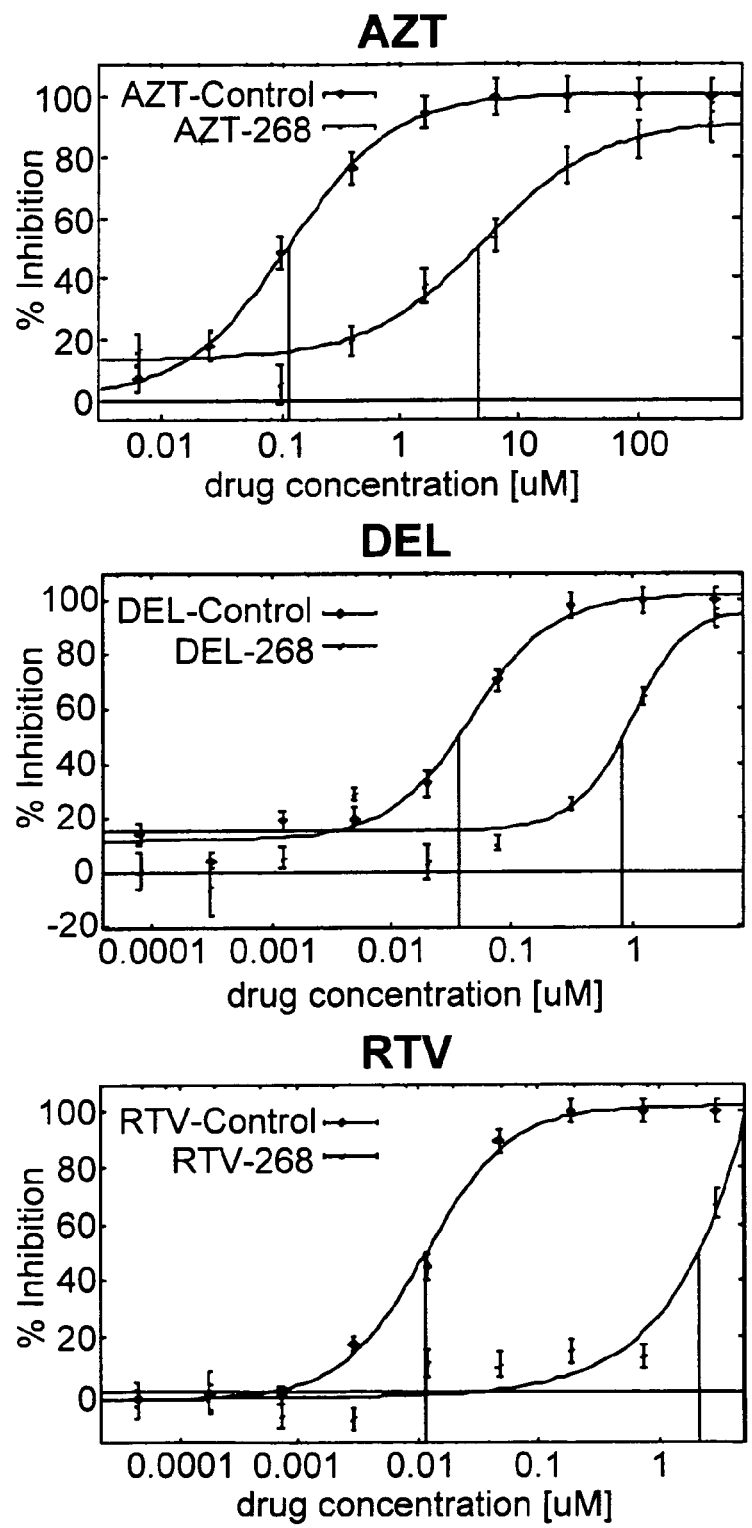
Figure 4A:
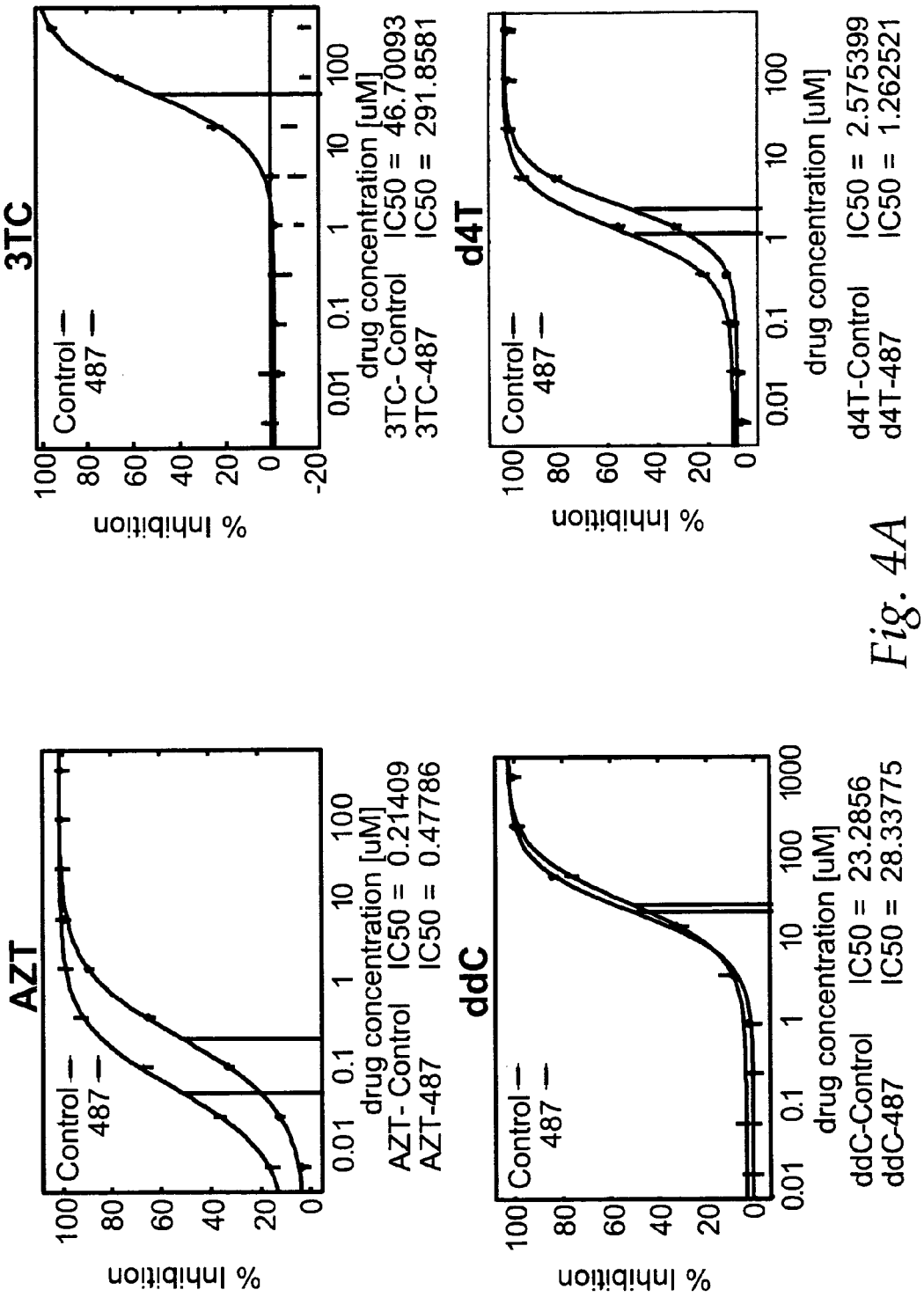
Figure 4B:
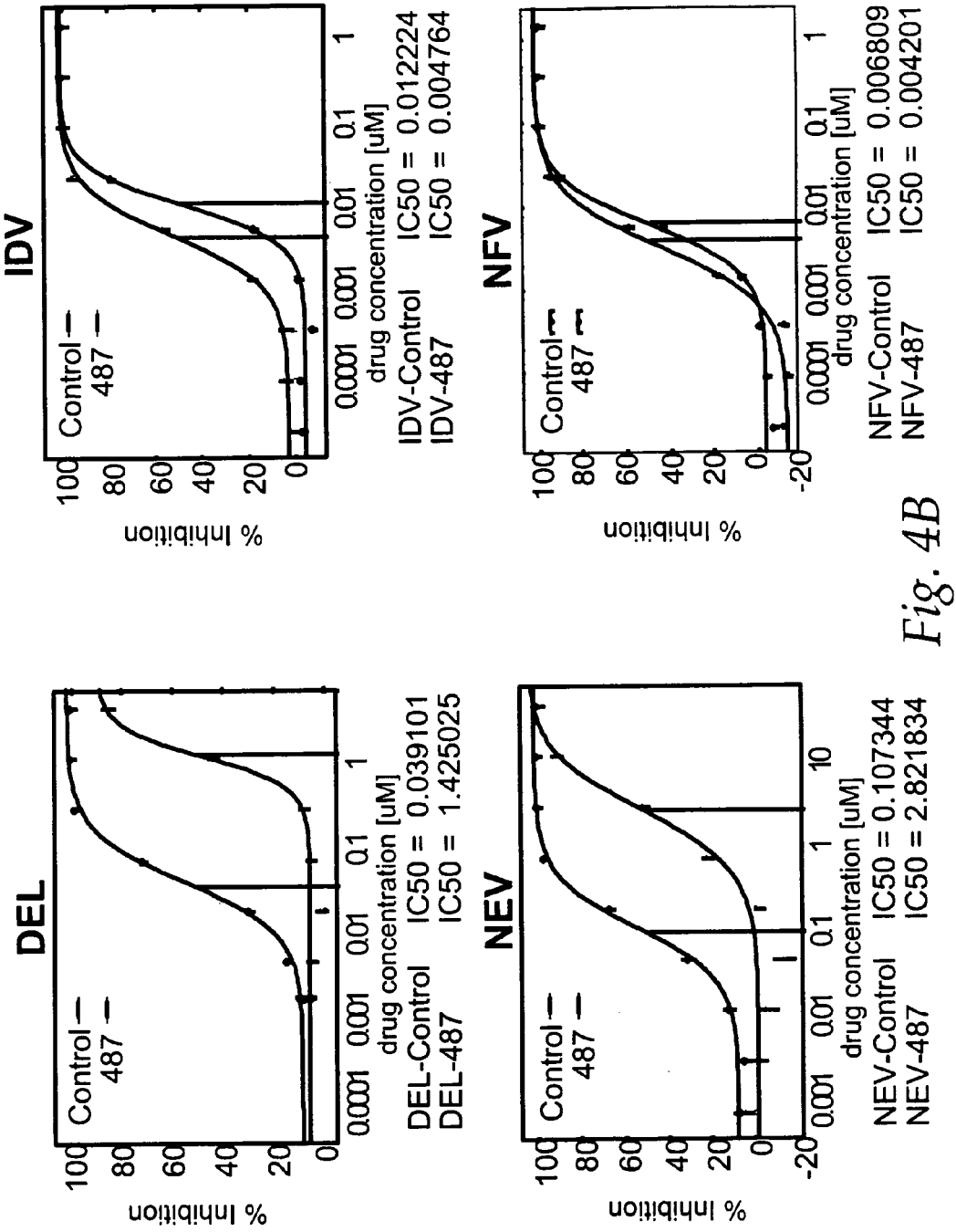
Figure 4C:
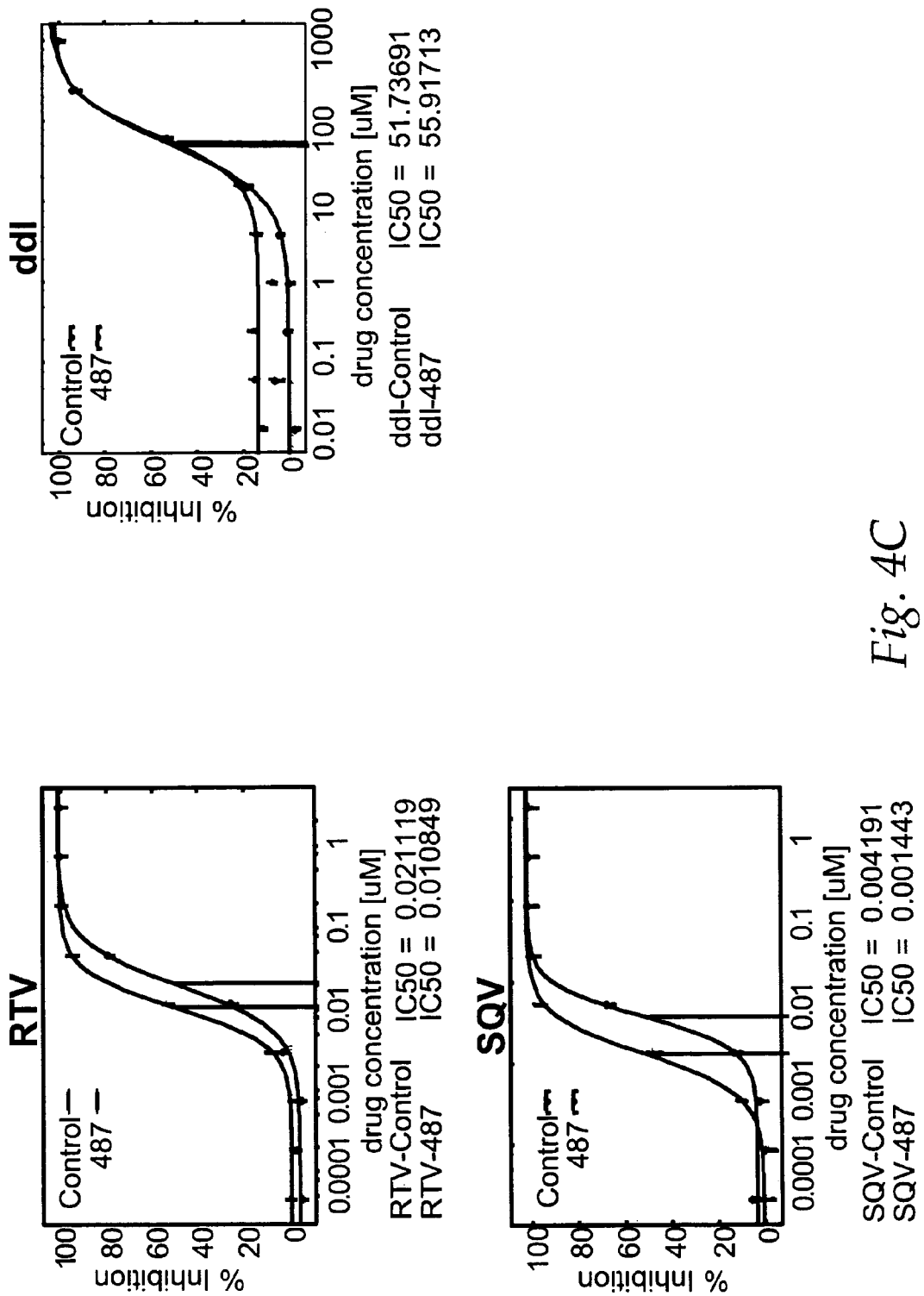
Figure 5:
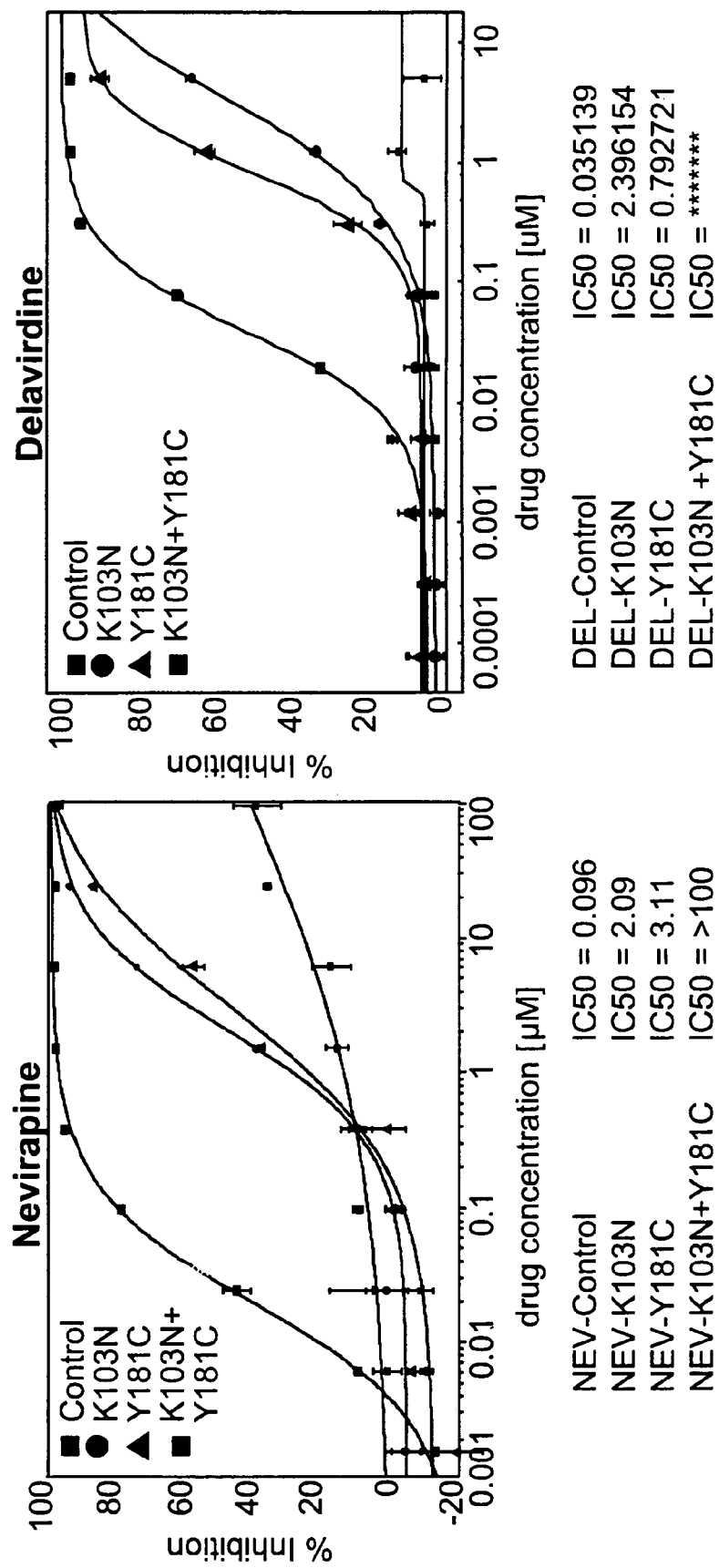

Host cells were seeded in 10-cm-diameter dishes and were transfected several days after plating with resistance test vector plasmid DNA and the envelope expression vector. Transfections were performed using a calcium-phosphate precipitation procedure. The cell culture media containing the DNA precipitate was replaced with fresh medium, from one to 24 hours, after transfection. Cell culture media containing resistance test vector viral particles was harvested one to four days after transfection and was passed through a 0.45-mm filter before being stored at 80° C. HIV capsid protein (p24) levels in the harvested cell culture media were determined by an EIA method as described by the manufacturer (SIAC; Frederick, Md.). Before infection, target cells (293 and 293/T) were plated in cell culture media. Control infections were performed using cell culture media from mock transfections (no DNA) or transfections containing the resistance test vector plasmid DNA without the envelope expression plasmid. One to three or more days after infection the media was removed and cell lysis buffer (Promega) was added to each well. Cell lysates were assayed for luciferase activity (FIG. 3). The inhibitory effect of the drug was determined using the following equation:

$$\text{luciferase inhibition} = 1 - (\text{RLU}luc[\text{drug}] \div \text{RLU}luc) \times 100$$

where RLUluc [drug] is the relative light unit of 25 luciferase activity in infected cells in the presence of drug and RLUluc is the Relative Light Unit of luciferase activity in infected cells in the absence of drug. IC50 values were obtained from the sigmoidal curves that were generated from the data by plotting the percent inhibition of luciferase activity vs. the log drug concentration. The drug inhibition curves are shown in (FIG. 3).

EXAMPLE 2

Correlating Phenotypic Susceptibility and Genotypic Analysis

Phenotypic Susceptibility Analysis of Patient HIV Samples

Resistance test vectors are constructed as described in example 1. Resistance test vectors, or clones derived from the resistance test vector pools, are tested in a phenotypic assay to determine accurately and quantitatively the level of susceptibility to a panel of anti-retroviral drugs. This panel of anti-retroviral drugs may comprise members of the classes known as nucleoside-analog reverse transcriptase inhibitors (NRTIs), non-nucleoside reverse transcriptase inhibitors (NNRTIs), and protease inhibitors (PRIs). The panel of drugs can be expanded as new drugs or new drug targets become available. An IC50 is determined for each resistance test vector pool for each drug tested. The pattern of susceptibility to all of the drugs tested is examined and compared to known patterns of susceptibility. A patient sample can oe further examined for genotypic changes correlated with the pattern of susceptibility observed.

Genotypic Analysis of Patient HIV Samples

Resistance test vector DNAs, either pools or clones, are analyzed by any of the genotyping methods described in Example 2. In one embodiment of the invention, patient HIV sample sequences are determined using viral RNA purification, RT/PCR and ABI chain terminator automated sequencing. The sequence that is determined is compared to control sequences present in the database or is compared to a sample from the patient prior to initiation of therapy, if available. The genotype is examined for sequences that are different from the control or pre-treatment sequence and correlated to the observed phenotype.

Phenotypic Susceptibility Analysis of Site Directed Mutants

Genotypic changes that are observed to correlate with changes in phenotypic patterns of drug susceptibility are evaluated by construction of resistance test vectors containing the specific mutation on a defined, wild-type 35 (drug susceptible) genetic background. Mutations may be incorporated alone and/or in combination with other known drug resistance mutations that are thought to modulate the susceptibility of HIV to a certain drug or class of drugs. Mutations are introduced into the resistance test vector through any of the widely known methods for site-directed mutagenesis. In one embodiment of this invention the mega-primer PCR method for site-directed mutagenesis is used. A resistance test vector containing the specific mutation or group of mutations is then tested using the phenotypic susceptibility assay described above and the susceptibility profile is compared to that of a genetically defined wild-type (drug susceptible) resistance test vector which lacks the specific mutations. Observed changes in the pattern of phenotypic susceptibility to the antiretroviral drugs tested is attributed to the specific mutations introduced into the resistance test vector.

EXAMPLE 3

Correlating Phenotypic Susceptibility and Genotypic Analysis: P225H

Phenotypic Analysis of Patient 97-302

Figure 8A:
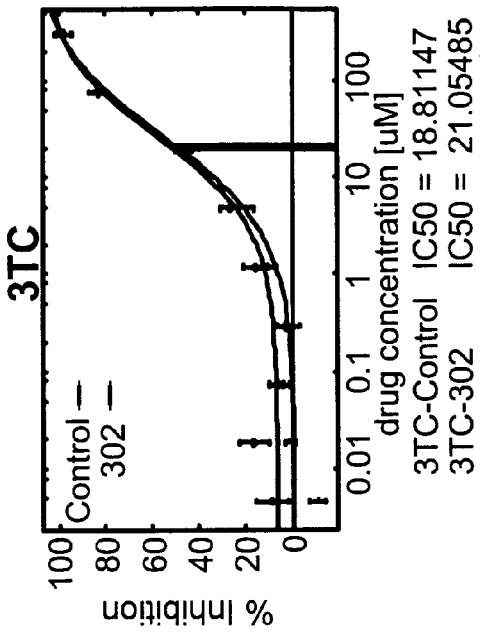
Figure 8A:
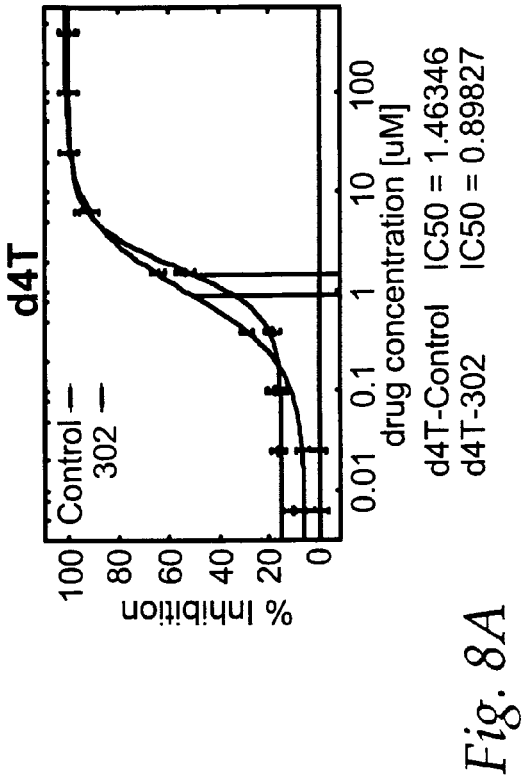
Figure 8A:
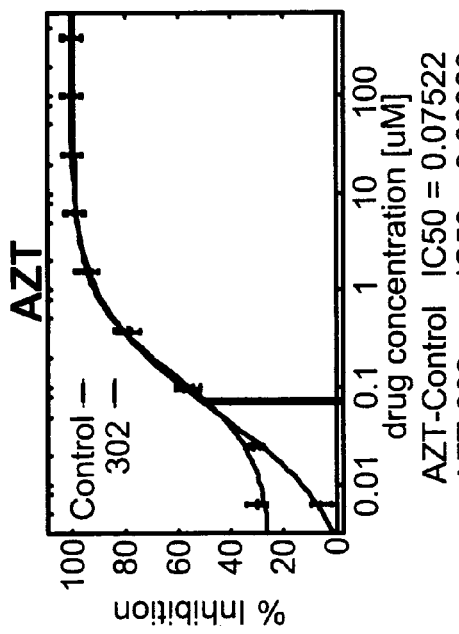
Figure 8A:
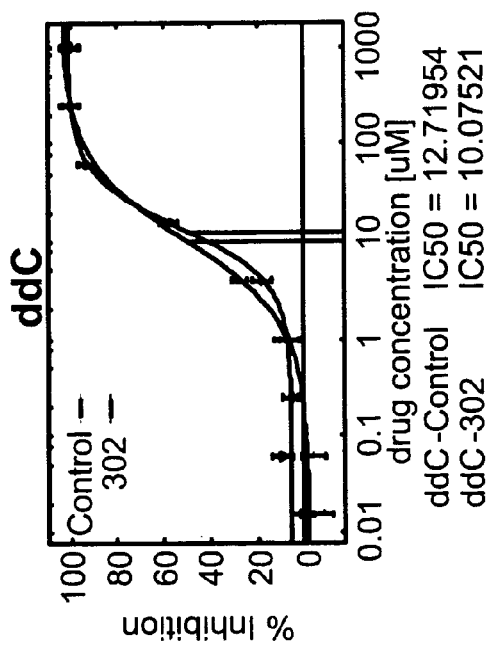
Figure 8B:
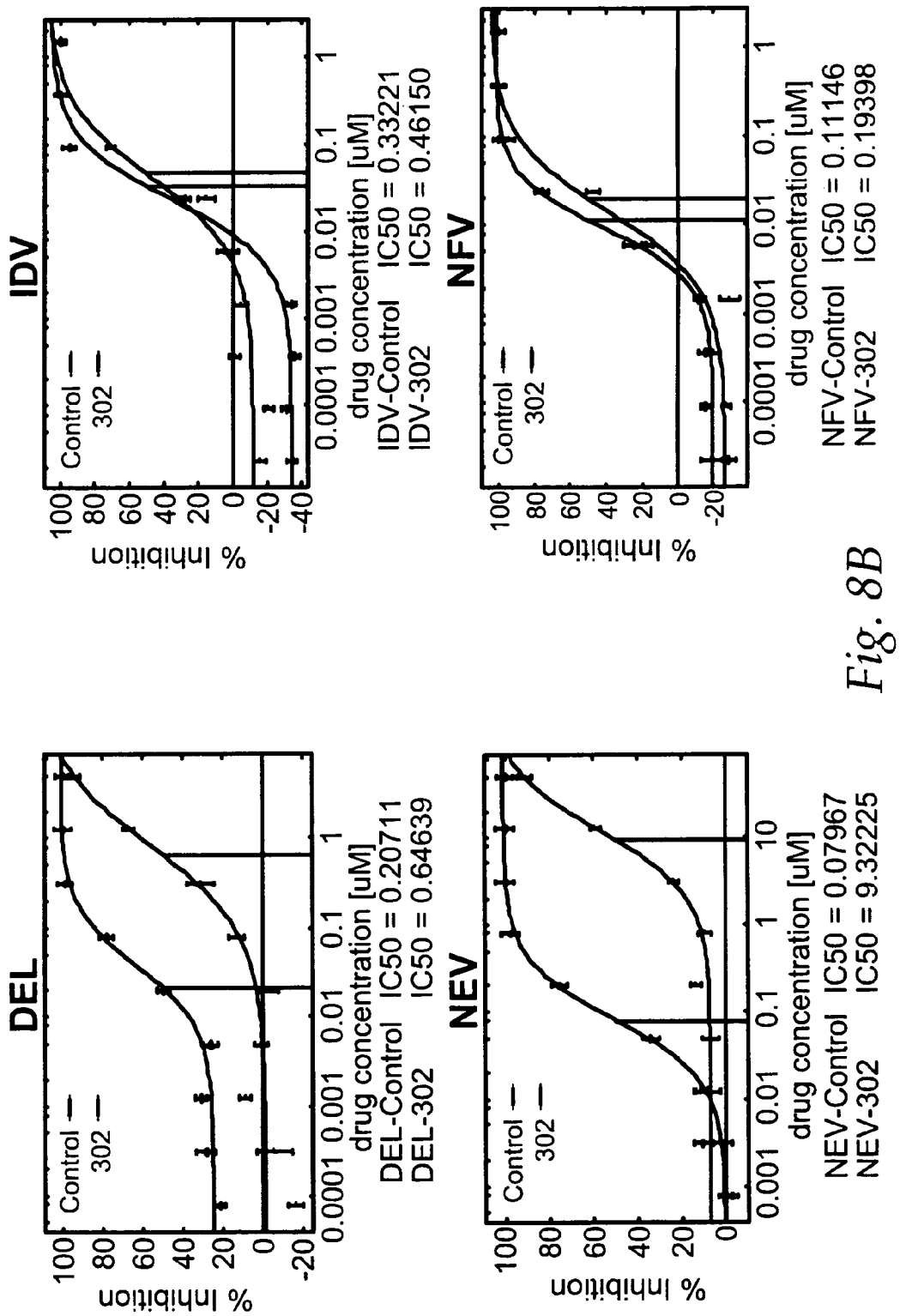
Figure 8C:
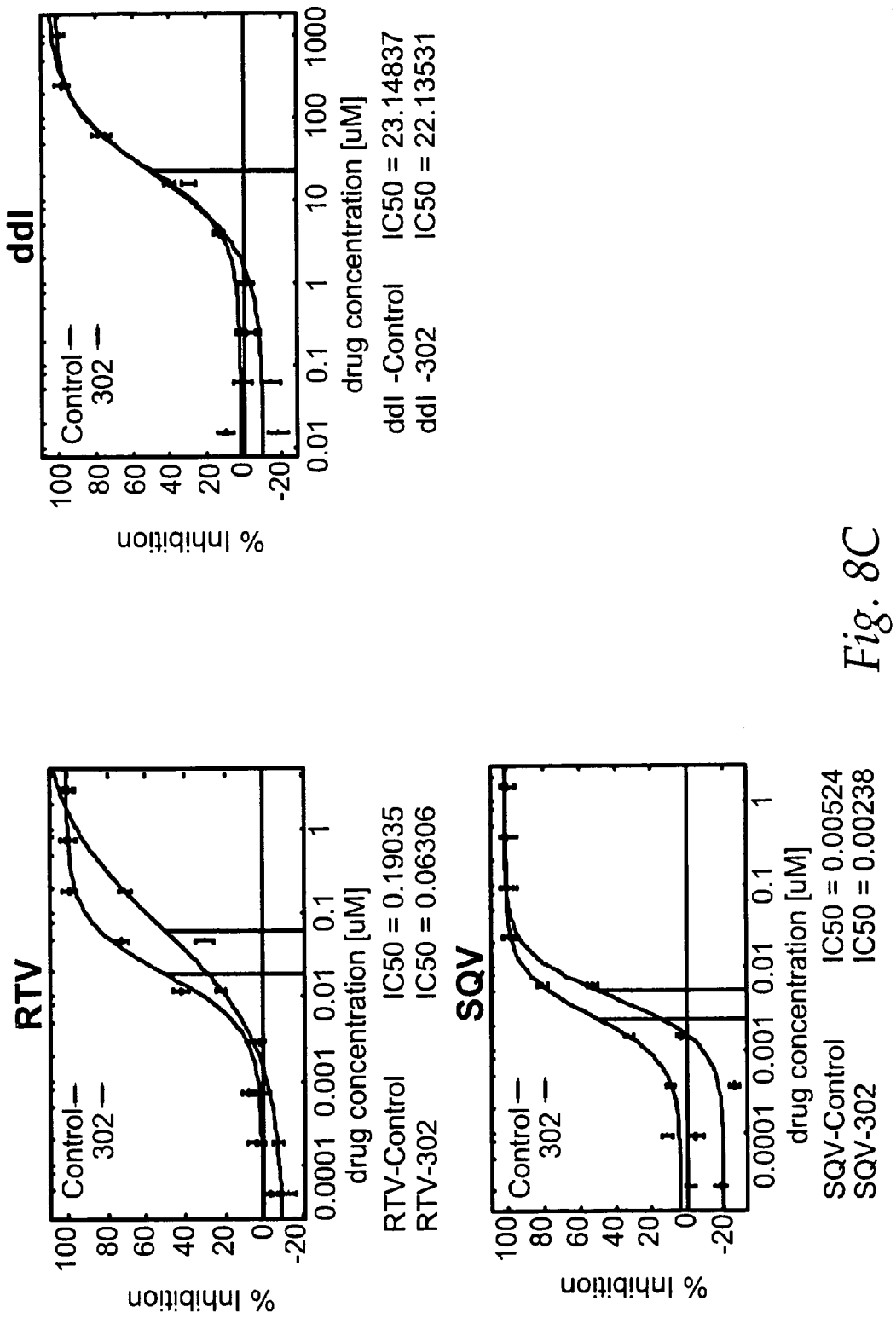

A resistance test vector was constructed as described in example 1 from a patient sample designated as 97-302. This patient had been treated with d4T, indinavir and DMP-266 for a period of approximately 10 months. Isolation of viral RNA and RT/PCR was used to generate a patient derived segment that comprised viral sequences coding for all of PR and aa 1-313 of RT. The patient derived segment was inserted into a indicator gene viral vector to generate a resistance test vector designated RTV-302. RTV-302 was tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine and nevirapine), and PRIs (indinavir, nelfinavir, ritonavir, and saquinavir). An IC50 was determined for each drug tested. Susceptibility of the patient virus to each drug was examined and compared to known patterns of susceptibility. A pattern of susceptibility to the NNRTIs was observed for patient sample RTV-302 in which there was significant decrease in nevirapine susceptibility (increased resistance) and modest decrease in delavirdine susceptibility (See FIG. 8A). Patient sample 97-302 was examined further for genotypic changes associated with the observed pattern of susceptibility.

Determination of Genotype of Patient 97-302

RTV-302 DNA was analyzed by ABI chain terminator automated sequencing. The nucleotide sequence was compared to the consensus sequence of a wild type clade B HIV-1 (HIV Sequence Database, Los Alamos, N. Mex.). The nucleotide sequence was examined for sequences that are different from the control sequence. RT mutations were noted at positions K103N, I135M, T200A, am P225H. K103N is associated with resistance to the NNRTIs and has been shown using the phenotypic susceptibility assay to be associated with reduced susceptibility to both delavirdine and nevirapine to an equal extent. The mutations at I135M and T200A are known polymorphisms of the wild-type (drug-sensitive) variants of HIV. The mutation, P225H was characterized using site directed mutagenesis and phenotypic susceptibility testing to correlate the changes at amino acid 225 with changes In NNRTI phenotypic susceptibility.

Site Directed Mutagenesis

Figure 8D:
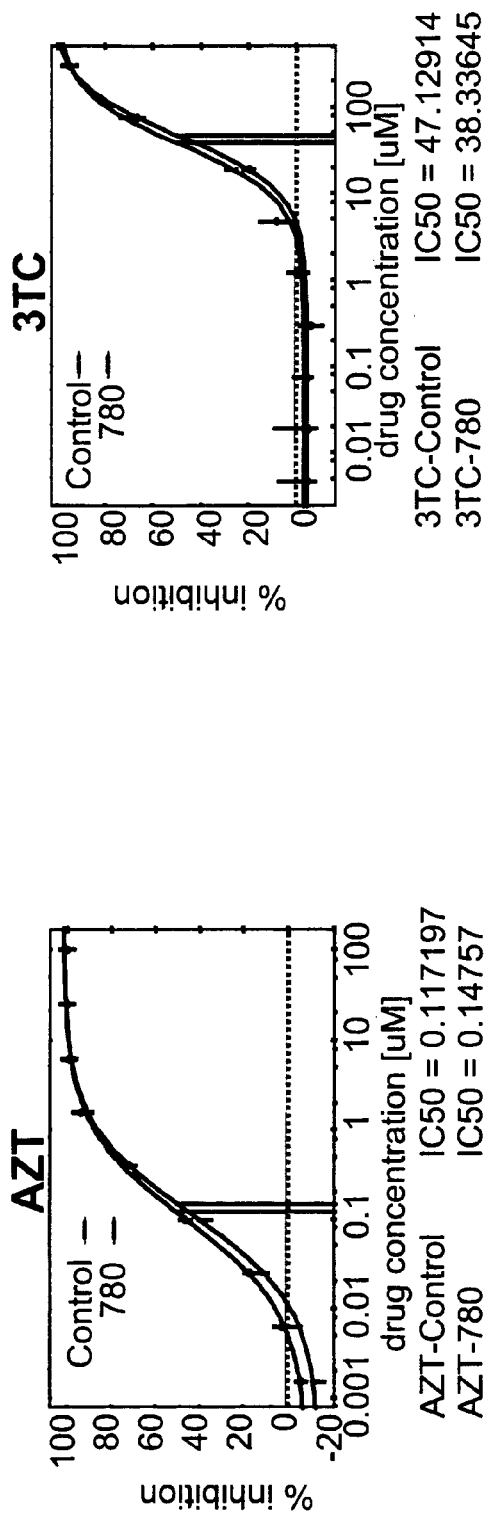
Figure 8D:
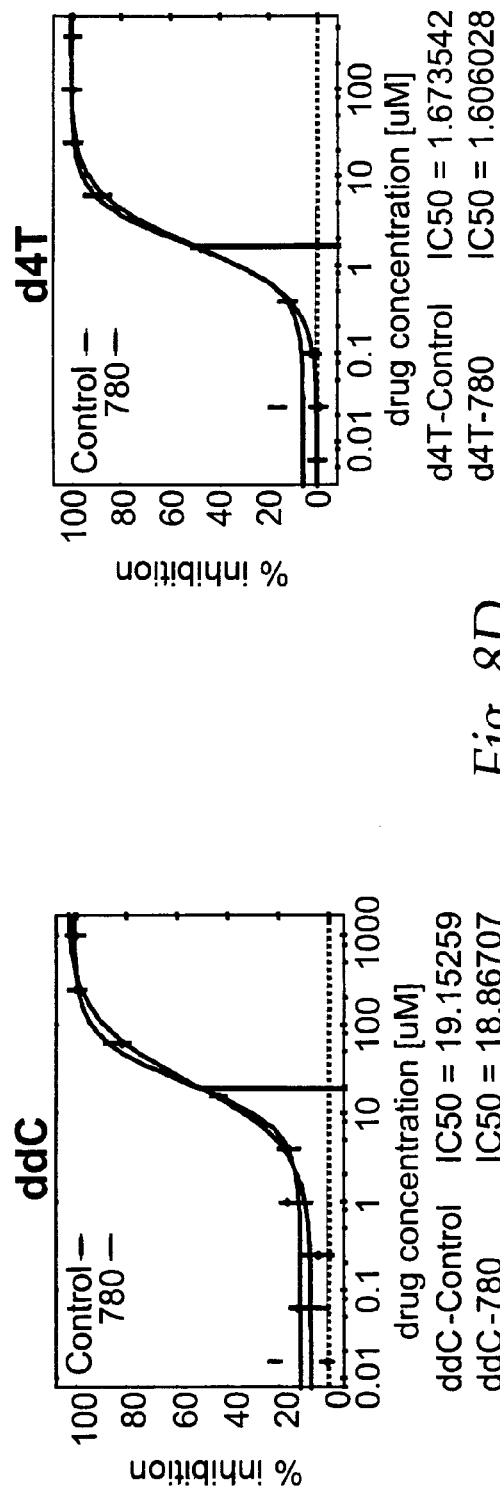
Figure 8E:
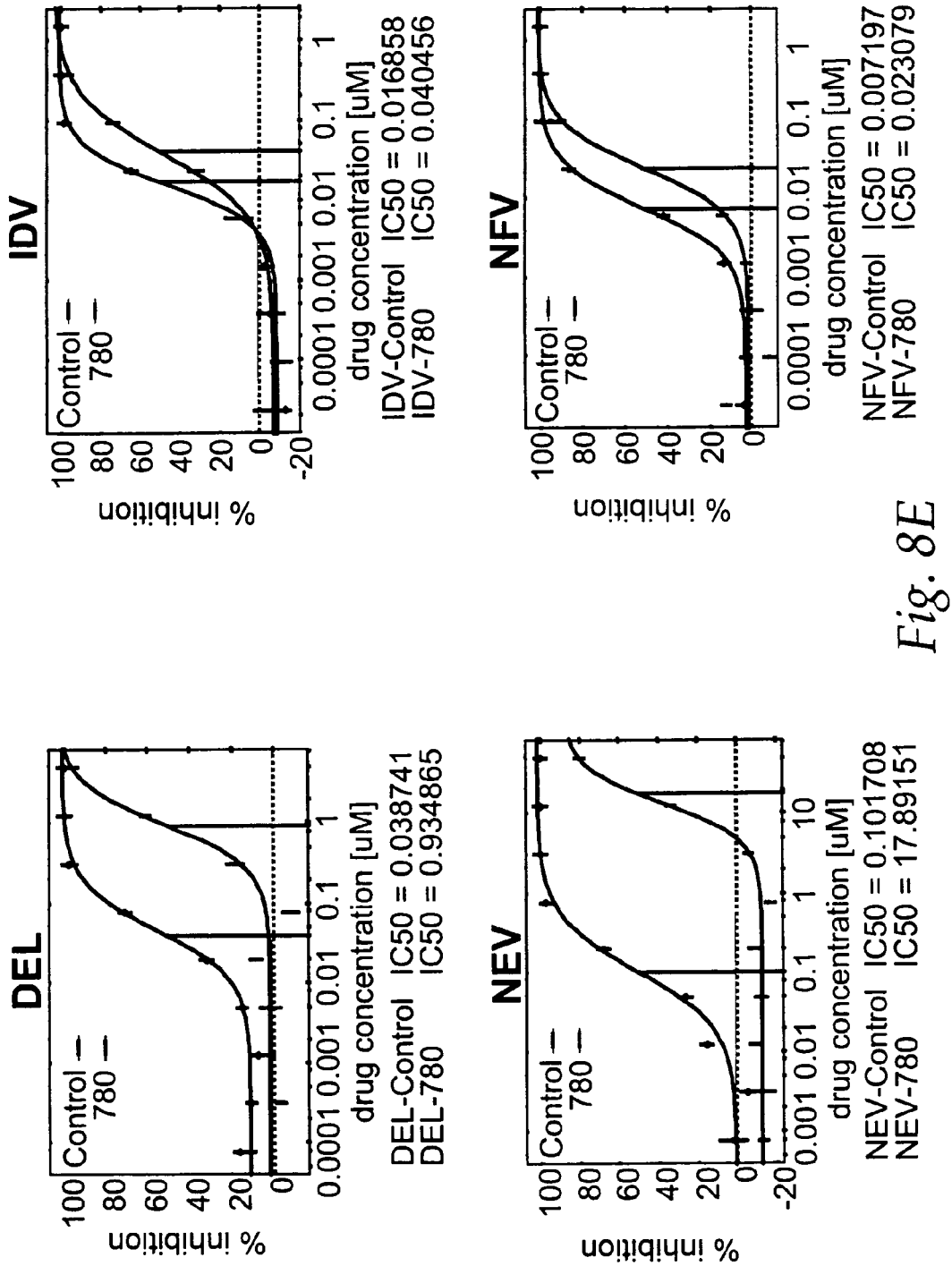
Figure 8F:
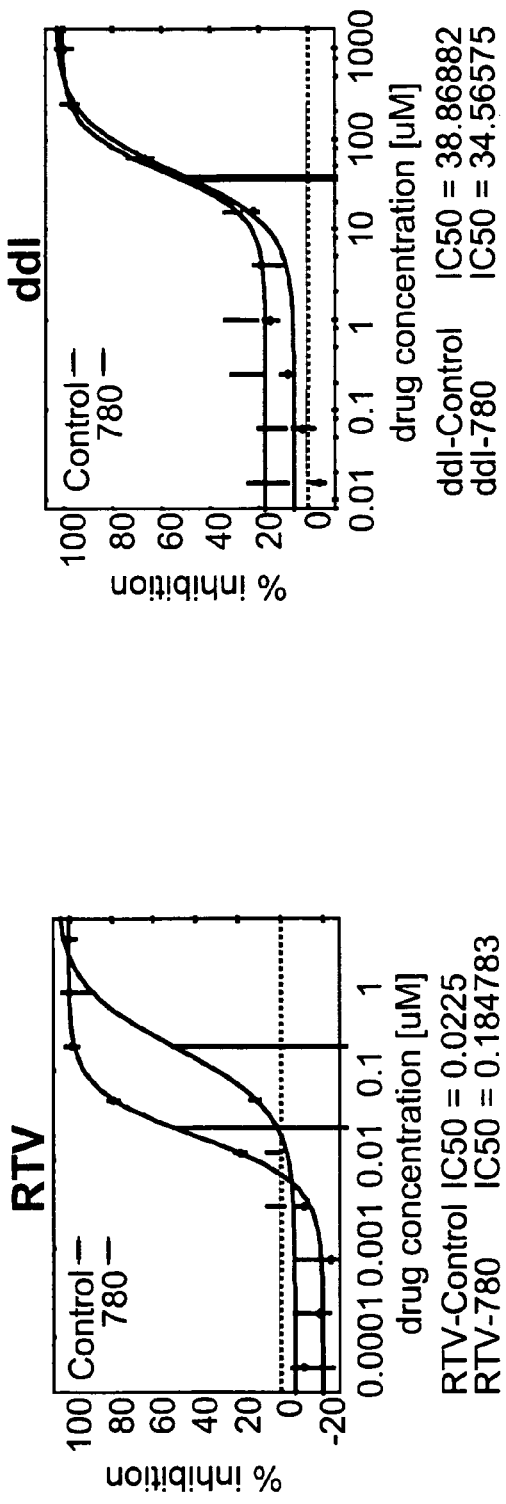
Figure 8G:
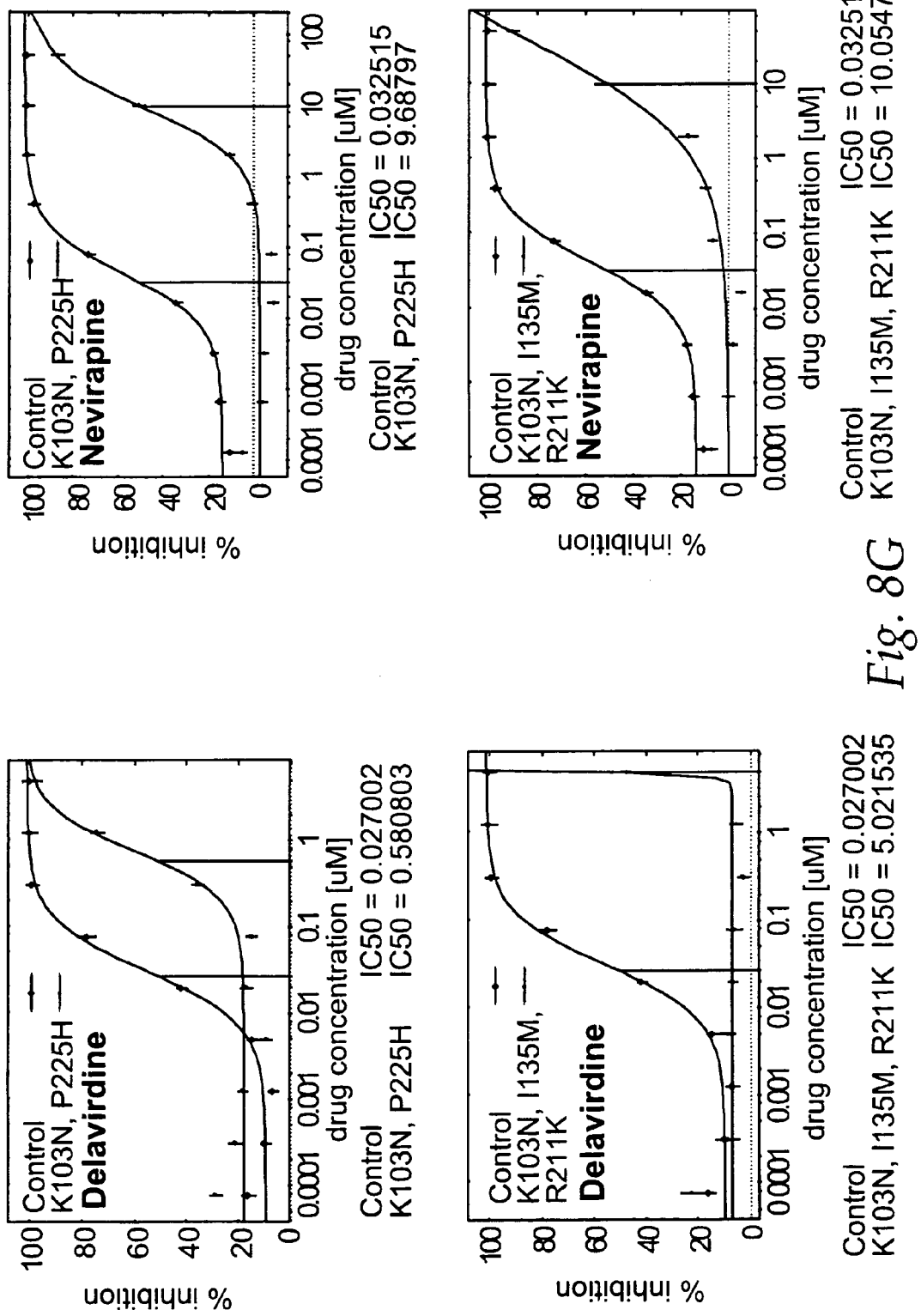
Figure 8H:
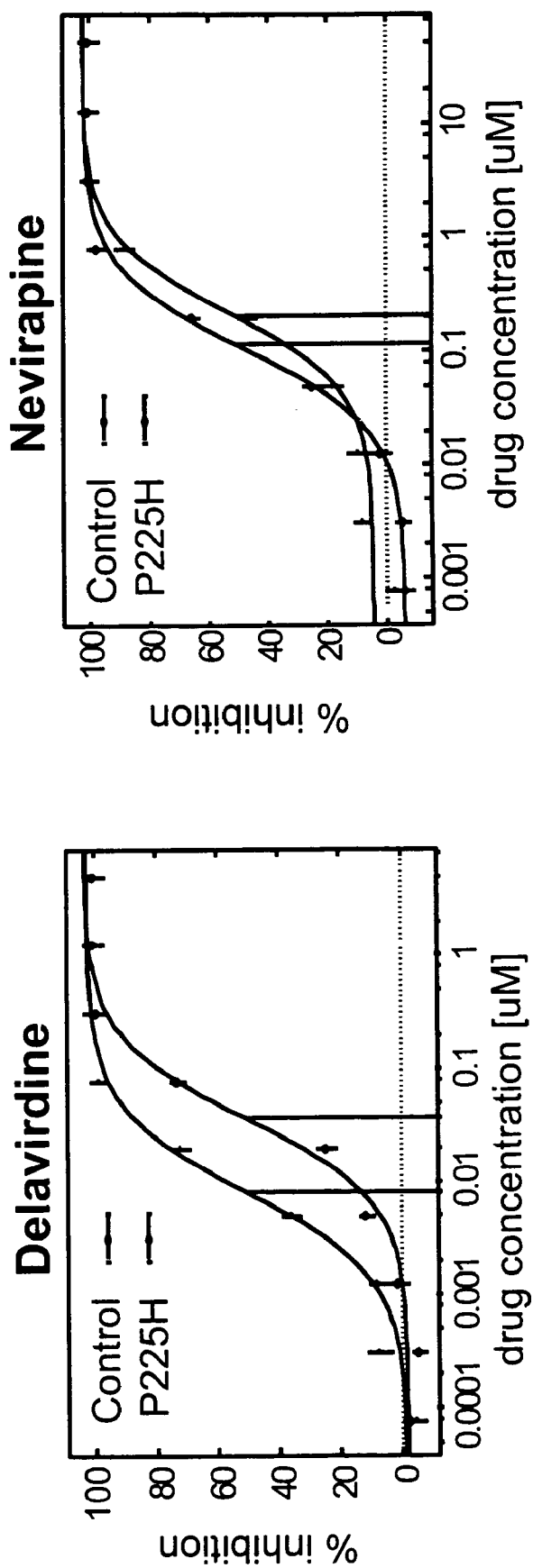
Figure 8I:
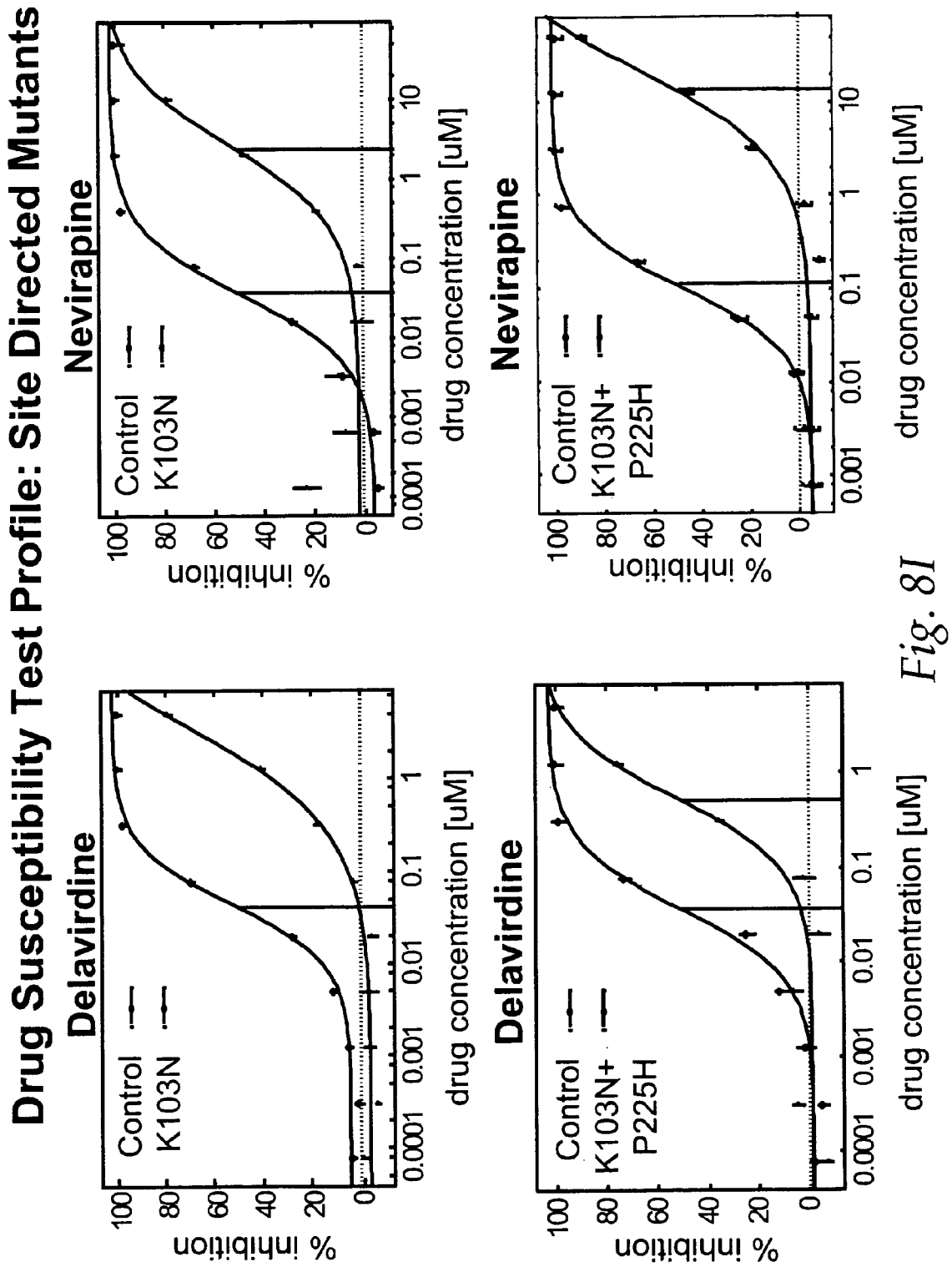
Figure 8J:
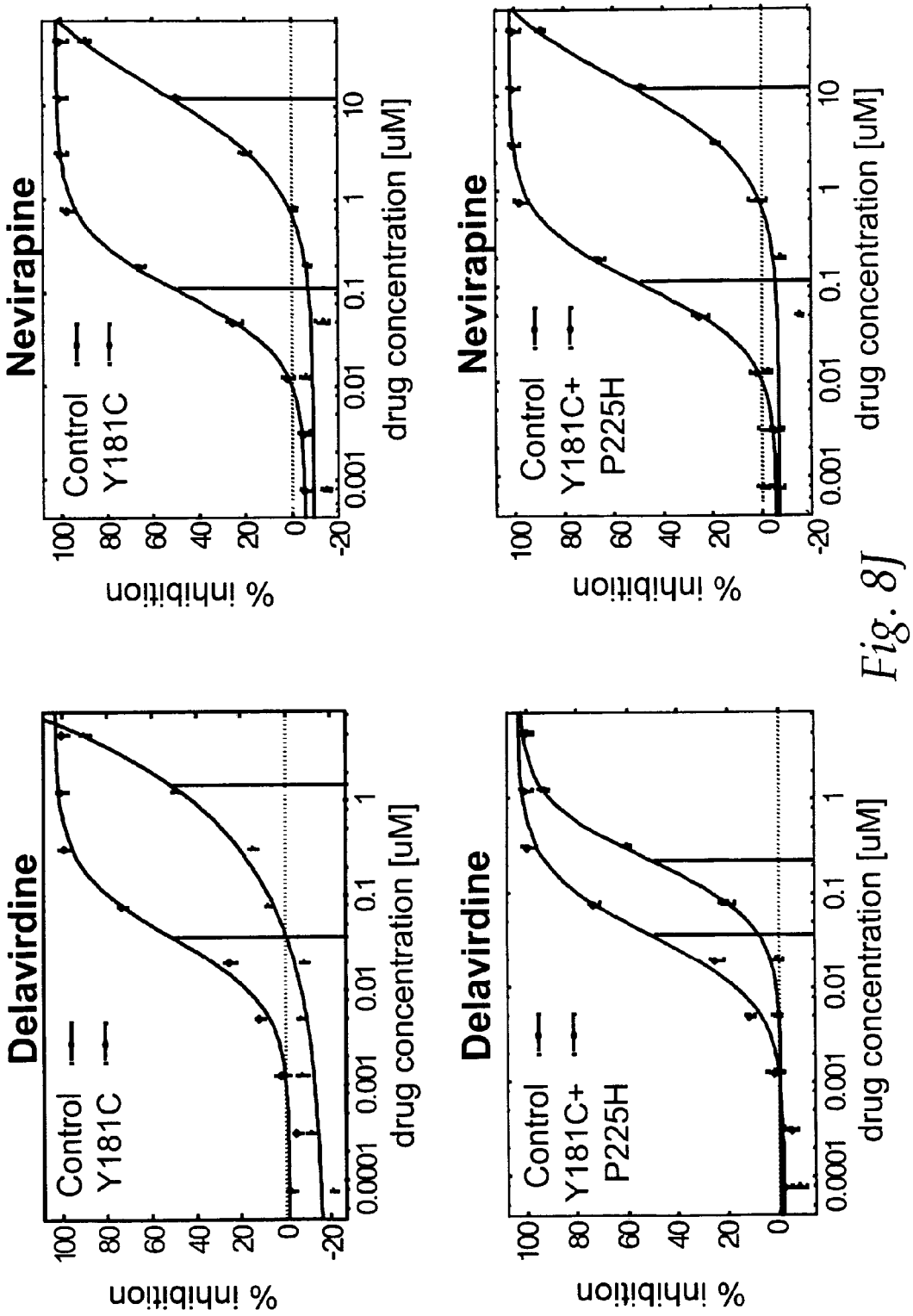
Figure 9A:
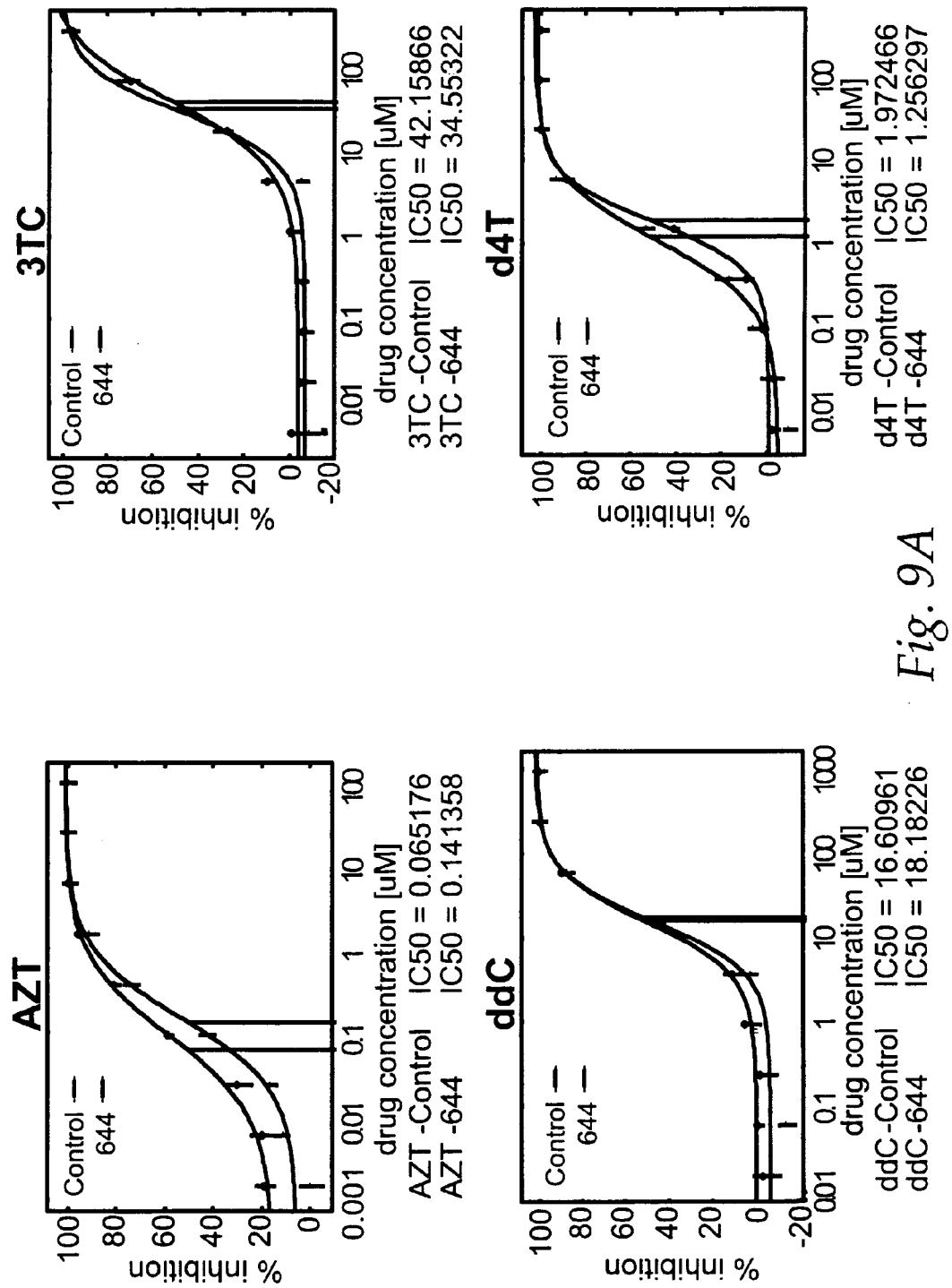
Figure 9B:
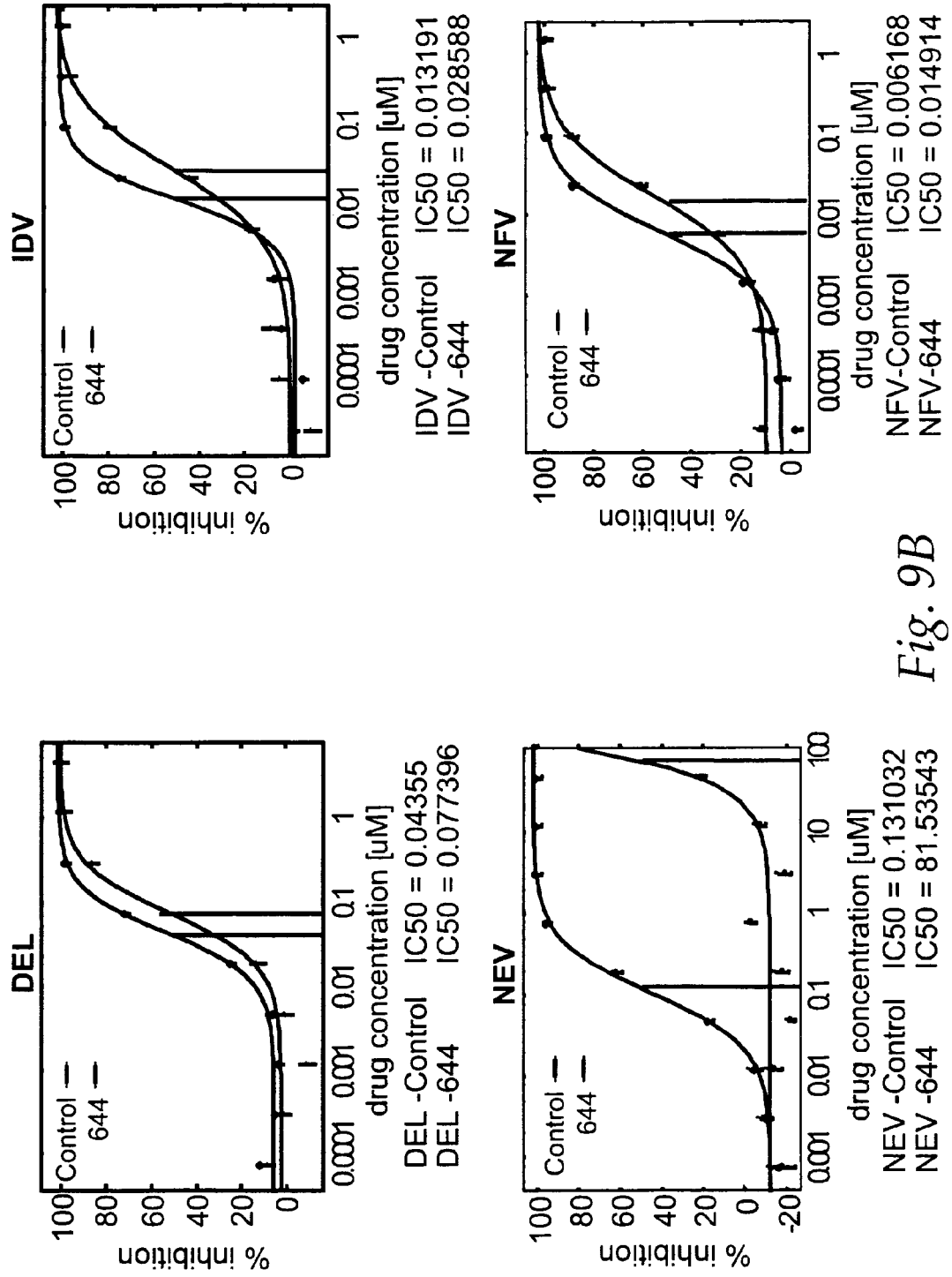
Figure 9C:
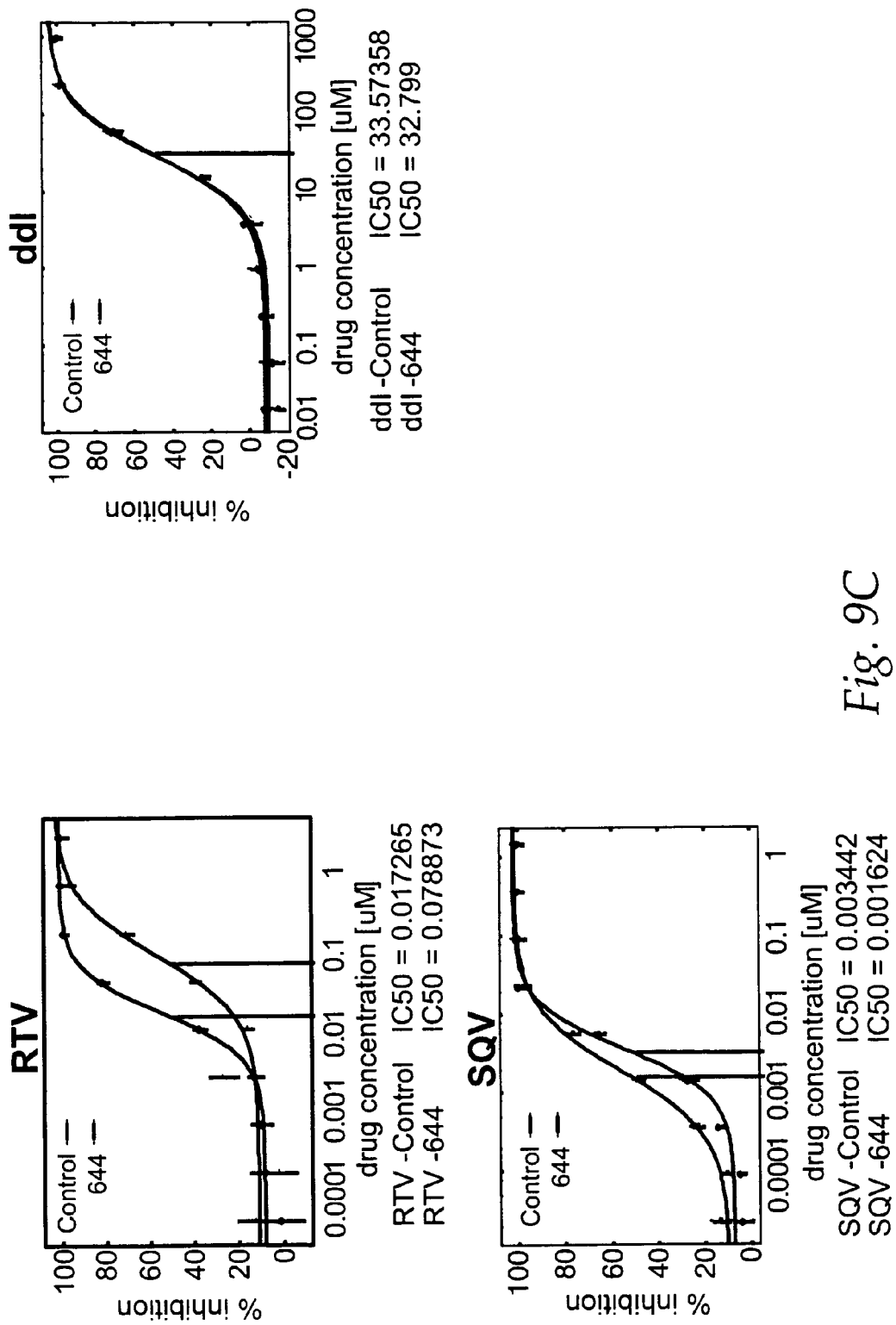
Figure 9D:
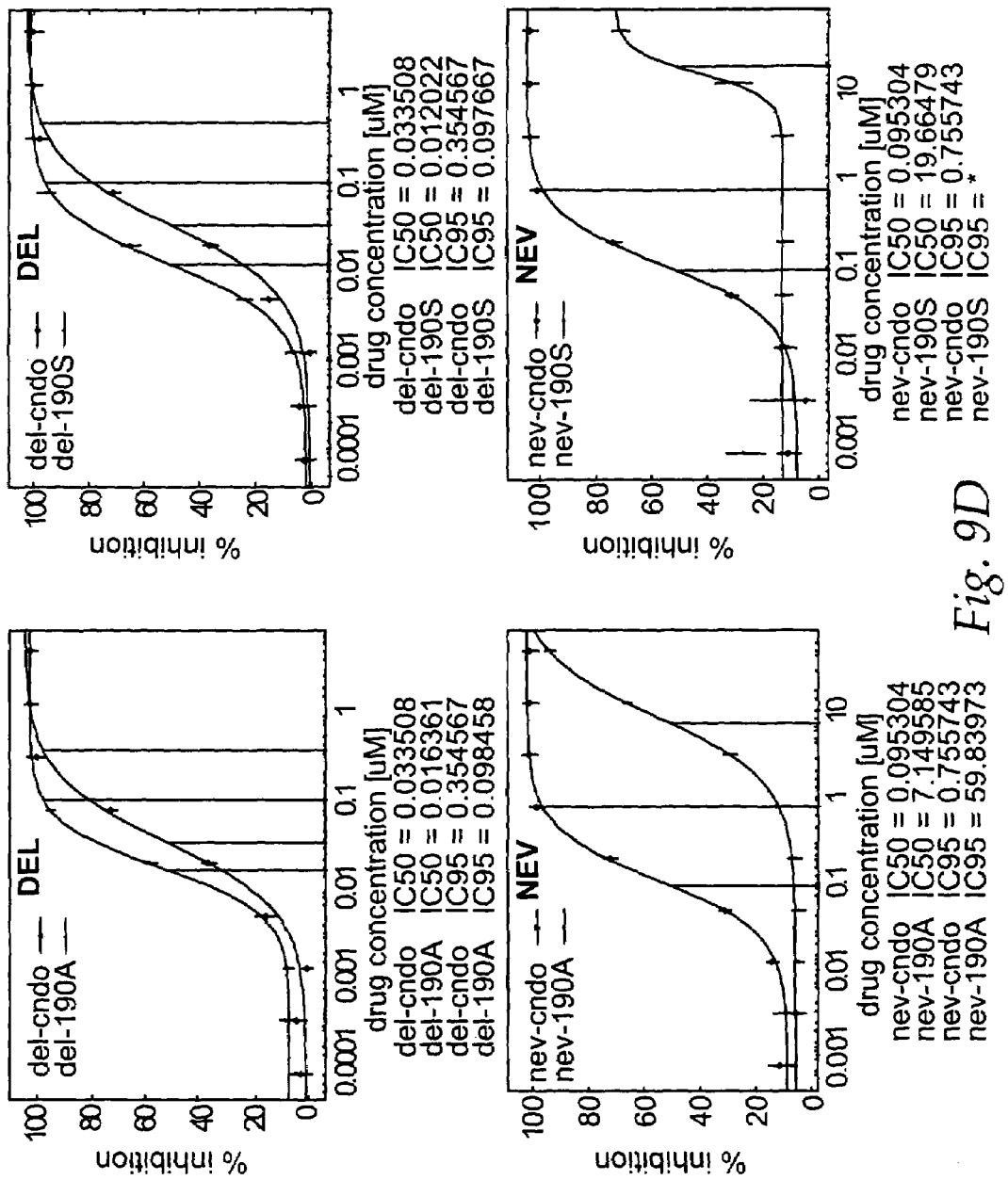

Resistance test vectors were constructed containing the P225H mutation alone and in combination with other known drug resistance mutations (K103N, Y181C) known to modulate the HIV susceptibility to NNRTIs. Mutations were introduced into the resistance test vector using the mega-primer PCR method for site-directed mutagenesis. (Sakar G and Sommar S S (1994) *Biotechniques* 8(4), 404-407). A resistance test vector containing the P225H mutation (P225H-RTV) was tested using the phenotypic susceptibility assay described above and the results were compared to that of a genetically defined resistance test vector that was wild type at position 225. The pattern of phenotypic susceptibility to the NNRTI, delavirdine in the P225H-RTV was altered as compared to wild type. In the context of an otherwise wild type background (i.e. P225H mutation alone) the P225H-RTV was more susceptible to delavirdine than the wild type control RTV. No significant change in nevirapine susceptibility was observed in the P225H-RTV. The P225H mutation was also introduced into a RTV containing additional mutations at K103N, Y181C or both (K103N+Y181C). In all cases, RTVs were more susceptible to inhibition by delavirdine if the P225H mutation was present as compared to the corresponding RTV lacking the P225H mutation (FIG. 8D). In all cases the P225H mutation did not significantly change nevirapine susceptibility (FIG. 8D).

EXAMPLE 4

Correlating Phenotypic Susceptibility and Genotypic Analysis: P236L

Phenotypic Analysis of HIV Patient 97-268

A resistance test vector was constructed as described in Example 11 from a patient sample designated 97-268. This patient had been treated with AZT and 3TC (NRTIs), indinavir and saquinavir (PRIs) and delavirdine (an NNRTI) for periods varying from 1 month to 2 years. Isolation of viral RNA and RT/PCR was used to generate a patient derived segment that comprised viral sequences coding for all of PR and amino acids 1-313 of RT. The patient derived segment was inserted into a indicator gene viral vector to generate a resistance test vector designated RTV-268. RTV-268 was then tested using the phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine and nevirapine), and PRIs (indinavir, nelfinavir, ritonavir, and saquinavir). An IC50 was determined for each drug tested. Susceptibility of the patient virus to each drug was examined and compared to the susceptibility of a reference virus. A pattern of susceptibility to the NNRTIs was observed for the patient sample RTV-268 in which the virus sample was observed to be resistant to delavirdine with no resistance to delavirdine. The sample was examined further for genotypic changes associated with the pattern of susceptibility.

Genotype of HIV Patient 97-268

RTV-268 DNA was analyzed by ABI chain terminator automated sequencing. The nucleotide sequence was compared to the consensus sequence of wild type clade B HIV-1. The nucleotide sequence was evaluated for sequences different from the control sequence. RT mutations were noted at positions M41L, D67N, M184V, T200A, E203D, L210W, T215Y, K219Q, and P236L compared to the control sequence. The mutations at T200A and E203D are known polymorphisms in wild-type (drug-sensitive) variants of HIV. Mutations at positions M41L, D67N, L210W, T215Y, and K219Q are associated with AZT resistance. The mutation at M184V is associated with 3TC resistance. The mutation at P236L is associated with resistance to delavirdine and increased susceptibility to nevirapine (Dueweke et al., Ibid.). In contrast to previous reports, the RTV-268 sample showed no change in nevirapine susceptibility. The mutation, P236L, was characterized using site directed mutagenesis and in vitro phenotypic susceptibility testing to correlate changes at amino acid 236 with changes in phenotypic susceptibility.

Site Directed Mutagenesis

Resistance test vectors were constructed containing the P236L mutation alone and in combination with other known drug resistance mutations (K103N, Y181C) that are known to modulate the susceptibility of HIV-1 to NNRTIs. Mutations were introduced into the resistance test vector using the mega-primer PCR. method for site-directed mutagenesis (Sakar and Sommar, Ibid.). A resistance test vector containing the P236L mutation (P236L-RTV) was tested using the phenotypic susceptibility assay and the results were compared to that of a genetically defined resistance test vector that was wild type at position 236. P236L-RTV exhibited changes in NNRTI phenotypic susceptibility. In the context of an otherwise wild type background (i.e. P236L mutation alone) the P236L-RTV is less susceptible to delavirdine than a wild type reference RTV. In contrast to Dueweke et al. no significant change in nevirapine susceptibility was observed for P236L-RTV. The P236L mutation was also introduced into a RTV containing mutations at K103N, Y181C or both (K103N+Y181C). In all cases, the RTVs were less susceptible (more resistant) to delavirdine if the P236L mutation was present as compared to the corresponding RTV lacking the P236L mutation. In all cases the P236L mutation did not significantly alter nevirapine susceptibility.

EXAMPLE 5

Correlating Phenotypic Susceptibility and Genotypic Analysis: G190S

Phenotypic Analysis of HIV Patient 97-644

A resistance test vector was constructed as described in Example 1 from a patient sample designated 97-644. This patient had been treated with d4T (NRTI), indinavir (PRI) and efavirenz (NNRTI). for a period varying from to 17 months. Isolation of viral RNA and RT/PCR was used to generate a patient derived segment that comprised viral sequences coding for all of PR and amino acids 1-313 of RT. The patient derived segment was inserted into a indicator gene viral vector to generate a resistance test vector designated RTV-644. RTV-644 was then tested using the phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine and nevirapine), and PRIs (indinavir, nelfinavir, ritonavir, and saquinavir). An IC50 was determined for each drug tested. Susceptibility of the patient virus to each drug was examined and compared to the susceptibility of a reference virus. A pattern of susceptibility to the NNRTIs was observed for the patient sample RTV-644 in which the virus sample was observed to be resistant to nevirapine with little or no resistance to delavirdine. The sample was examined further for genotypic changes associated with the pattern of susceptibility.

Genotype of HIV Patient 97-644

RTV-644 DNA was analyzed by ABI chain terminator automated sequencing. The nucleotide sequence was compared to the consensus sequence of wild type clade B HIV-1. The nucleotide sequence was evaluated for sequences different from the control sequence. RT mutations were noted at positions K101E and G190S compared to the control sequence. The mutations at T200A and E203D are known polymorphisms in wild-type (drug-sensitive) variants of HIV. The mutation at K101E is associated with resistance to some but not all NNRTIs. The mutation G190A but not specifically G190S is associated with nevirapine and loviride resistance. The mutations G190S and G190A were characterized using site directed mutagenesis and in vitro phenotypic susceptibility testing to correlate changes at amino acid 190 with changes in phenotypic susceptibility.

Site Directed Mutagenesis

Resistance test vectors were constructed containing the G190S and G190A mutations. Mutations were introduced into the resistance test vector using the mega-primer PCR method for site-directed mutagenesis (Sakar and Sommar, Ibid.). Resistance test vectors containing the G190S or G190A mutations (G190S-RTV, or G190A-RTV) were tested using the phenotypic susceptibility assay and the results were compared to that of a genetically defined resistance test vector that was wild type at position G190. G190S-RTV and G190A-RTV exhibited changes in NNRTI phenotypic susceptibility. In the context of an otherwise wild type background these RTVs were markedly less susceptible to nevirapine and slightly more susceptible to delavirdine than a wild type reference RTTr.

EXAMPLE 6

Predicting Response to Non-Nucleoside Reverse Transcriptase Inhibitors by Characterization of Amino Acid Changes in HIV-1 Reverse Transcriptase Phenotypic and Genotypic Correlation of Mutations at Amino Acid 236 of HIV-1 Reverse Transcriptase In one embodiment of this invention, changes in the amino acid at position 236 of the reverse transcriptase protein of HIV-1 is evaluated using the following method comprising: (i) collecting a biological sample from an HIV-1 infected subject; (ii) evaluating whether the biological sample contains nucleic acid encoding HIV-1 reverse transcriptase having a mutation at codon 236. The presence of a mutation at codon 236 (P236L) is correlated with a reduction in delavirdine susceptibility and little or no change in nevirapine susceptibility.

The biological sample comprises whole blood, blood components including peripheral mononuclear cells (PBMC), serum, plasma (prepared using various anticoagulants such as EDTA, acid citrate-dextrose, heparin), tissue biopsies, cerebral spinal fluid (CSF), or other cell, tissue or body fluids. In another embodiment, the HIV-1 nucleic acid (genomic RNA) or reverse transcriptase protein can be isolated directly from the biological sample or after purification of virus particles from the biological sample. Evaluating whether the amino acid at position 236 of the HIV-1 reverse transcriptase is mutated, can be performed using various methods, such as direct characterization of the viral nucleic acid encoding reverse transcriptase or direct characterization of the reverse transcriptase protein itself. Defining the amino acid at position 236 of reverse transcriptase can be performed by direct characterization of the reverse transcriptase protein by conventional or novel amino acid sequencing methodologies, epitope recognition by antibodies or other specific binding proteins or compounds. Alternatively, the amino acid at position 236 of the HIV-1 reverse transcriptase protein can be defined by characterizing amplified copies of HIV-1 nucleic acid encoding the reverse transcriptase protein. Amplification of the HIV-1 nucleic acid can be performed using a variety of methodologies including reverse transcription-polymerase chain reaction (RT-PCR), NASBA, SDA, RCR, or 3SR as would be known to the ordinarily skilled artisan. Evaluating whether the nucleic acid encoding HIV reverse transcriptase has a mutation at codon 236 can be performed by direct nucleic acid sequencing using various primer extension-chain termination (Sanger, ABI/PE and Visible Genetics) or chain cleavage (Maxam and Gilbert) methodologies or more recently developed sequencing methods such as matrix assisted laser desorption-ionization time of flight (MALDI-TOF) or mass spectrometry (Sequenom, Gene Trace Systems). Alternatively, the nucleic acid sequence encoding amino acid position 236 can be evaluated using a variety of probe hybridization methodologies, such as genechip hybridization sequencing (Affymetrix), line probe assay (LiPA; Murex), and differential hybridization (Chiron).

In a preferred embodiment of this invention, evaluation of whether amino acid position 236 of HIV-1 reverse transcriptase was wild type or mutant was carried out using a phenotypic susceptibility assay using resistance test vector DNA prepared from the biological sample. In one embodiment, plasma sample was collected, viral RNA was purified and an RT-PCR methodology was used to amplify a patient derived segment encoding the HIV-1 protease and reverse transcriptase regions. The amplified patient derived segments were then incorporated, via DNA ligation and bacterial transformation, into an indicator gene viral vector thereby generating a resistance test vector.

Resistance test vector DNA was isolated from the bacterial culture and the phenotypic susceptibility assay was carried out as described in Example 1. The results of the phenotypic susceptibility assay with a patient sample having a P236L mutation. The nucleic acid (DNA) sequence of the patient derived HIV-1 protease and reverse transcriptase regions from patient sample 268 was determined using a fluorescence detection chain termination cycle sequencing methodology (ABI/PE). The method was used to determine a consensus nucleic acid sequence representing the combination of sequences of the mixture of HIV-1 variants existing in the subject sample (representing the quasispecies), and to determine the nucleic acid sequences of individual variants.

Phenotypic susceptibility profiles of patient samples and site directed mutants showed that delavirdine and nevirapine susceptibility correlated with the absence of RT mutations at positions 103, 181 or 236 or HIV-1 reverse transcriptase. Phenotypic susceptibility profiles of patient samples and site directed mutants snowed a significant reduction in delavirdine susceptibility (increased resistance) and little or no reduction in nevirapine susceptibility correlated with a mutation in the nucleic acid sequence encoding the amino acid leucine (L) at position 236 of HIV-1 reverse transcriptase and the absence of mutations at positions 103 and 181.

Phenotypic susceptibility profiles of patient samples and site directed mutants showed no additional reduction in delavirdine or nevirapine susceptibility (increased resistance) with the amine acid proline at position 236 when the RT mutations at positions 103, 181 or 103 and 181 were present (K103N, Y181C, or K103N+Y181C). However, phenotypic susceptibility profiles of patient samples and site directed mutants showed an additional reduction in delavirdine susceptibility (increased resistance) and little or no additional reduction in nevirapine susceptibility with the amino acid leucine (L) at position 236 in addition to the RT mutations associated with NNRTI resistance (K103N, Y181C, or K103N+Y181C).

Phenotypic and Genotypic Correlation of Mutations at Amino Acid 225 of HIV-1 Reverse Transcriptase Phenotypic susceptibility profiles of patient samples and site directed mutants showed no change in susceptibility to delavirdine or nevirapine when the amino acid proline (P) was present at position 225 or HIV-1 reverse transcriptase in the absence of RT mutations associated with NNRTI resistance (K103N, Y181C). However, phenotypic susceptibility profiles of patient samples and site directed mutants showed an increase in delavirdine susceptibility and little or no change nevirapine susceptibility when the amino acid histidine (H) was present at position 225 in the absence of RT mutations (K103N, Y181C) associated with NNRTI resistance.

Phenotypic susceptibility profiles of patient samples and site directed mutants showed no additional reduction in delavirdine susceptibility or nevirapine susceptibility when the amino acid proline (P) at position 225 was present in addition to the RT mutations associated with NNRTI resistance (K103N, Y181C, or K103N+Y181C). In contrast phenotypic susceptibility profiles of patient samples and site directed mutants showed an increase in delavirdine susceptibility and little or no change in nevirapine susceptibility when the amino acid histidine (H) was present at position 225 in the presence of RT mutations associated with NNRTI resistance (K103N, Y181C, or K103N+Y181C).

Phenotypic and Genotypic Correlation of Mutations at Amino Acid 190 of HIV-1 Reverse Transcriptase Phenotypic susceptibility profiles of patient samples and site directed mutants showed no change in susceptibility to delavirdine or nevirapine when the amino acid glycine (G) at position 190 was present in the absence of RT mutations associated with NNRTI resistance (K103N, Y181C). Phenotypic susceptibility profiles of site directed mutants showed an increase in delavirdine susceptibility and a decrease in nevirapine susceptibility when the amino acid alanine (A) was present at position 190 in the absence of RT mutations associated with NNRTI resistance. Phenotypic susceptibility profiles of patient samples and site directed mutants showed an increase in delavirdine susceptibility and a decrease in nevirapine susceptibility when the amino acid serine (S) was present at position 190 in the absence of RT mutations associated with NNRTI resistance.

EXAMPLE 8

Using Resistance Test Vectors and Site Directed Mutants to Correlate Genotypes and Phenotypes Associated with NNRTI Drug Susceptibility and Resistance in HIV: Y181I Preparation of Resistant Test Vectors and Phenotypic Analysis of Patient 98-964 HIV Samples A resistant test vector was constructed as described in Example 1 from a patient sample designated 98-964. This patient had been previously treated with ddI, d4T, AZT, 3TC, ddC, (NRTIs), saquinavir and nelfinavir (PRIs) and nevirapine (an NNRTI) and HU. Isolation of viral RNA and RT/PCR was used to generate a patient derived segment that comprised viral sequence coding for all of PR and aa 1-313 of RT. The PDS was inserted into an indicator gene viral vector to generate a resistance test vector designated RTV-964. RTV-964 was then tested in a phenotypic assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine and nevirapine), and PRIs (indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to NNRTIs was observed for patient RTV-964 in which there was a moderate decrease (10-fold) in delavirdine susceptibility and a significant decrease (750-fold) in nevirapine susceptibility.

Determination of Genotype of Patient HIV Samples

RTV-964 DNA was analyzed by ABI chain terminator automated sequencing. The nucleotide sequence was compared to the consensus sequence of a wild type clade B HIV-1 (HIV Sequence Database, Los Alamos, N. Mex.). The genotype was examined for sequences that are different from the control sequence. Mutations were noted at positions M41L, K43E, D67N, K70R, L74I, V75S, Y181I, R211T, T215Y, D218E, and K219Q compared to the control sequence. M41L, D67N, K70R, L74I, V75S, T215Y, and K21SQ are associated with NRTI resistance. A mutation at R211T is a known polymorphism in the sequence among different wildtype (drug-sensitive) variants of HIV. Y181I had previously been shown to be associated with high level resistance to nevirapine. We examined the mutation, Y181I, using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Anti-Retroviral Drugs in HIV The Y181I mutation was introduced into the resistance test vector using the mega-primer method for site-directed mutagenesis (Sakar and Sommar, Ibid). A resistance test vector containing the Y181I mutation (Y181I-RTV) was then tested using the phenotypic assay described earlier and the results were compared to those determined using a genetically defined resistance test vector that was wild type at position 181. We determined the pattern of phenotypic susceptibility to the NNRTIs, delavirdine, nevirapine and efavirenz, in the Y181I-RTV. On a wild type background (i.e. Y181I mutation alone) the Y181I-RTV displayed a moderate loss of susceptibility (20-fold) to delavirdine and a significant loss of susceptibility (740-fold) to nevirapine compared to a wild type control RTV. The Y181I-RTV showed wild-type susceptibility (1.4-fold) to efavirenz.

EXAMPLE 9

Using Resistance Test Vectors and Site Directed Mutants to Correlate Genotypes and Phenotypes Associated with NNRTI Drug Susceptibility and Resistance in HIV: Y188

Preparation of Resistant Test Vectors and Phenotypic Analysis of Patient 97-300 HIV Samples A resistance test vector was constructed as described in Example 1 from a patient sample designated 97-300. This patient had been previously treated with d4T and 3TC (NRTIs), indinavir (a PRI) and efavirenz (an NNRTI). Isolation of viral RNA and RT/PCR was used to generate a patient derived segment that comprised viral sequences coding for all of PR and aa 1-313 of RT. The PDS was inserted into an indicator gene viral vector to generate a resistance test vector designated RTV-300. RTV-300 was then tested in a phenotypic assay to determine accurately and quantitatively the level of susceptibility to a panel of anti-retroviral drugs. This panel of anti-retroviral drugs comprised members of the classed known as NRTIs (AZT, 3TC, d4T, ddI and ddC), NNRTIs (delavirdine, efavirenz and nevirapine), and PRIs (indinavir, nelfinavir, ritonavir, and saquinavir). An IC50 was determined for the resistance test vector pool for each drug tested. The pattern of susceptibility to all of the drug tested was examined and compared to known patterns of susceptibility. A pattern of susceptibility to the NNRTIs was observed for patient RTV-300 in which there was moderate decrease (25-fold) in delavirdine susceptibility and a substantial decrease (greater than 800-fold) in nevirapine susceptibility.

Determination of Genotype of Patient HIV Samples

RTV-300 DNA analyzed by ABI chain terminator automated sequencing. The nucleotide sequence was compared to the consensus sequence of a wild type clade B HIV-1 (HIV Sequence Database, Los Alamos, N. Mex.). The genotype was examined for sequence that are different from the control sequence. Mutations were noted at positions K32N, M184V and Y188L compared to the control sequence. The mutation at M184V is associated with 3TC resistance. Y188L had previously been shown to be associated with high level resistance to efavirenz. Other mutations at position Y188 (i.e. Y188C and Y188H) have been reported to have been selected for by treatment with several NNRTIs (E-ePseU, E-EPS, HEPT, Nevirapine, BHAP, U-8720E, TIBO R082913, Loviride). We examined the mutation, Y188L, using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Antiretroviral Drugs in HIV The Y188L mutation was introduced into the resistance test vector using the mega-primer method for site-directed mutagenesis (Sakar and Sommar, Ibid.). A resistance test vector containing the Y188L mutation (Y188L-RTV) was then tested using the phenotypic assay described earlier and the results were compared to those determined using a genetically defined resistance test vector that was wild type at position 188. We determined the pattern of phenotypic susceptibility to the NNRTIs, delavirdine, nevirapine and efavirenz, in the Y188L-RTV. On a wild type background (i.e. Y138L mutation alone) the Y188L-RTV displayed a slight loss of susceptibility (9-fold) to delavirdine and substantial loss of susceptibility (greater than 800-fold) to nevirapine and a significant loss of susceptibility (109-fold) to efavirenz compared to a wild type control RTV. The approximate 100-fold loss of susceptibility to efavirenz was not as high as had been previously reported.

Site Directed Mutagenesis is Used to Confirm the Role of Specific Mutations in Phenotypic Susceptibility to Antiretroviral Drugs in HIV The Y188C mutation was introduced into the resistance test vector using the mega-primer method for site-directed mutagenesis (Sakar and Sommar, Ibid.). A resistance test vector containing the Y188C mutation (Y188C-RTV) was then tested using the phenotypic assay described earlier and the results were compared to those determined using a genetically defined resistance test vector that was wild type at position 188. We determined the pattern of phenotypic susceptibility to the NNRTIs, delavirdine, nevirapine and efavirenz, in the Y188C-RTV. On a wild type background (i.e. Y188C mutation alone) the Y188C-RTV displayed a slight loss of susceptibility (3-fold) to delavirdine and a moderate loss of susceptibility (30-fold) to nevirapine and efavirenz (20-fold) compared to a wild type control RTV.

Site Directed Mutagenesis is Used to Confirm the Role of Specific Mutations in Phenotypic Susceptibility to Antiretroviral Drugs in HIV The Y188H mutation was introduced into the resistance test vector using the mega-primer method for site-directed mutagenesis (Sakar and Sommai, Ibid.). A resistance test vector containing the Y188H mutation (Y188H-RTV) was then tested using the phenotypic assay described earlier and the results were compared to those determined using a genetically defined resistance test vector that was wild type at position 188. We determined the pattern of phenotypic susceptibility to the NNRTIs, delavirdine and nevirapine, in the Y188H-RTV. On a wild type background (i.e. Y188H mutation alone) the Y188H-RTV displayed a moderate loss of susceptibility (3.5-fold) to nevirapine compared to a wild type control RTV. The phenotypic susceptibility of Y188H to efavirenz was not determined.

EXAMPLE 10

Using Resistance Test Vectors and Site Directed Mutants to Correlate Genotypes and Phenotypes Associated with NNRTI Drug Susceptibility and Resistance in HIV: E138 and Y188

Preparation of Resistant Test Vectors and Phenotypic Analysis of Patient 97-209 HIV Samples A resistance test vector was constructed as described in Example 1 from a patient sample designated 97-209. This patient had been previously treated with AZT, ddI, d4T and 3TC (NRTIs), indinavir (a PRIs) and adefovir. Isolation of viral RNA and RT/PCR was used to generate a patient derived segment that comprised viral sequences ceding for all of PR and aa 1-313 of RT. The PDS was inserted into an indicator gene viral vector to generate resistance test vector designated RTV-209. RTV-209 was then tested in a phenotypic assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine, efavirenz and nevirapine), and PRIs (indinavir, nelfinavir, ritonavir, and saquinavir). An IC50 was determined for the resistance test vector pool for each drug tested. The pattern of susceptibility to ail of the drugs tested was examined and compared to known patterns of susceptibility. A pattern of susceptibility to the NNRTIs was observed for patient RTV-209 in which there was a moderate decrease (75-fold) in delavirdine susceptibility and a substantial decrease (greater than 800-fold) in nevirapine susceptibility.

Determination of Genotype of Patient HIV Samples

RTV-209 DNA was analyzed by ABI chain terminator automated sequencing. The nucleotide sequence was compared to the consensus sequence of a wild type clade B HIV-1 (HIV Sequence Database, Los Alamos, N. Mex.). The genotype was examined for sequences that are different from the control sequence. Mutations were noted at positions A62V, S68G, V76I, F77L, F116Y, E138A, Q151M, M184V, Y188L and E291D compared to the control sequence. The mutations at A62V, V75I, F77L, F116Y, Q151M and M184V are associated with NRTI resistance. A mutation at E138K had previously been shown to be associated with resistance to several NNRTIs and a mutation at Y188L had previously been shown to be associated with a decrease in susceptibility to efavirenz. We examined the mutations Y188L and E136A using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Antiretroviral Drugs in HIV The E138A mutation alone and in combination with Y188L was introduced into resistance test vectors using the mega-primer method for site-directed mutagenesis (Sakar and Sommar, Ibid.). Resistance test vectors containing the E138A mutation (E138A-RTV) or the E138 mutation along with the Y188L mutation (E138A-Y188L-RTV) were then tested using the phenotypic assay described earlier and the results were compared to those determined using a genetically defined resistance test vector that was wild type at positions 188 and 138. We determined the pattern of phenotypic susceptibility to the NNRTIs, delavirdine, nevirapine and efavirenz, in the E138A-RTV, Y188L-RTV and E138-Y188L-RTV. On a wild type background (i.e. E138A mutation alone) the E138A-RTV displayed wild-type susceptibility to delavirdine (1.6-fold), nevirapine (1.3-fold) and efavirenz (1.4-fold). The Y188L-RTV displayed a slight loss of susceptibility (greater than 800-fold) to nevirapine and a significant loss of susceptibility (110-fold) to efavirenz. The E138A-Y188L-RTV displayed a moderate loss of susceptibility (75-fold) to delavirdine and efavirenz (88-fold) and a substantial loss of susceptibility to nevirapine (greater than 800-fold) compared to a wild type control RTV. The combination of mutations resulted in an increased effect on delavirdine susceptibility compared to the effect observed for each mutation alone.

EXAMPLE 11

Using Resistance Test Vectors and Site Directed Mutants to 2 Correlate Genotypes and Phenotypes Associated with NNRTI Drug Susceptibility and Resistance in HIV: A98

Preparation of Resistant Test Vectors and Phenotypic Analysis of Patient 98-675 HIV Samples A resistance test vector was constructed as described in Example 1 from a patient sample designated 98-675. This patient had been previously treated with ddI, AZT, and 3TC (NRTIs), and saquinavir and nelfinavir (PRIs). Isolation of viral RNA and RT/PCR was used to generate a patient derived segment that comprised viral sequences coding for all of PR and aa 1-313 of RT. The PDS was inserted into an indicator gene viral vector to generate a resistance test vector designated RTV-765. RTV-675 was then tested in a phenotypic assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine, efavirenz and nevirapine), and PRIs (indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-675 in which wild-type susceptibility (2.1-fold) was observed for delavirdine and a slight decrease (6-fold) in nevirapine susceptibility was observed.

Determination of Genotype of Patient HIV Samples

RTV-675 DNA was analyzed by ABI chain terminator automated sequencing. The nucleotide sequence was compared to the consensus sequence of a wild type clade B HIV-1 (HIV Sequence Database, Los Alamos, N. Mex.). The genotype was examined for sequences that are different from the control sequence. Mutations were noted at positions M41L, S48t, L74V, A98G, M184V and T215Y are associated with NRTI resistance. A mutation at A98G had previously been shown to be associated with resistance to nevirapine. We examined the mutation A98G using site directed mutagenesis and in vitro henotypic susceptibility testing to correlate the observed changes in genotype with phenotype.

Site Directed Mutagenesis is Used to Confirm the Role of Specific Mutations in Phenotypic Susceptibility to Antiretroviral Drugs in HIV The A98G mutation into the resistance test vector using the mega-primer method for site-directed mutagenesis (Sakar and Sommar, Ibid.). A resistance test vector containing the A98G mutation (A98G-RTV) was then tested using the phenotypic assay described earlier and the results were compared to those determined using a genetically defined resistance test vector that was wild type at position 98. We determined the pattern of phenotypic susceptibility to the NNRTIs, delavirdine, nevirapine and efavirenz, in the A98G-RTV. On a wild type background (i.e. A98G mutation alone) the A98G RTV displayed a slight loss of susceptibility to delavirdine (3-fold), nevirapine (8-fold) and efavirenz (3-fold) compared to a wild type control RTV.

EXAMPLE 12

Using Resistance Test Vectors and Site Directed Mutants to Correlate Genotypes and Phenotypes Associated with NNRTI Drug Susceptibility and Resistance in HIV: A98 and G190

Preparation of Resistant Test Vectors and Phenotypic Analysis of Patient B HIV Samples.

A resistant test vector was constructed as described in Example 1 from a patient sample designated B. The anti-retroviral treatment this patient received is unknown. Isolation of viral RNA and RT/PCR was used to generate a patient derived segment that comprised viral sequences coding for ail of PR and aa 1-313 of RT. The PDS was inserted into an indicator gene viral vector to generate a resistant test vector designated RTV-B. Individual clones of the RTV-B pool were selected and then tested in a phenotypic assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine and nevirapine), and PRIs (indinavir, nelfinavir, ritonavir, and saquinavir). An IC50 was determined for the resistance test vector clone for each drug tested. The pattern of susceptibility to all of the drugs tested was examined and compared to known patterns of susceptibility. A pattern of susceptibility to the NNRTIs was observed for patient RTV-3 clone 1 in which there was an increase in susceptibility (0.55-fold) to delavirdine, a substantial loss of susceptibility (640-fold) to nevirapine and significant loss of susceptibility (250-fold) to efavirenz.

Determination of Genotype of Patient HIV Samples

RTV-B clone 1 DNA was analyzed by ABI chain terminator automated sequencing. The nucleotide sequence was compared to the consensus sequence of a wild type clade B HIV-1 (HIV Sequence Database, Los Alamos, N. Mex.). The genotype was examined for sequences that are different from the control sequence. Mutations were noted at positions M41L, A98G, M184V, L210W, R211?, T215Y, E397 and G190S compared to the control sequence M41L, M184V, L210W and T215Y are associated with NRTI resistance. A mutation at A98G had previously been shown to be associated with resistance to nevirapine. A mutation at position G190A had previously been shown to be associated with changes in susceptibility to nevirapine. Other changes at position 190 (i.e. E, Q, and T) have also been reported. We examined the mutations A98G and G190S, using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Antiviral Drugs in HIV The A98 and G190S mutations were introduced alone or in combination into the resistance test vector using the mega-primer method for site-directed mutagenesis (Sakar and Sommar, Ibid.). Resistance test vectors containing the A98G mutation (A98G-RTV), the G190S mutation (G190S-RTV) and both mutations (A98G-G190S-RTV) were then tested using the phenotypic assay described earlier and the results were compared to those determined using a genetically defined resistance test vector that was wild type at position 98 and 190. We determined the pattern of phenotypic susceptibility to the NNRTIs, delavirdine, nevirapine and efavirenz, in the three vectors. On a wild type background (i.e. A98G mutation alone) the A98G-RTV displayed a slight loss of susceptibility to delavirdine (3-fold), nevirapine (8-fold) and efavirenz (3-fold) compared to a wild type control RTV. On a wild type background (i.e. G190S mutation alone) the G190S-RTV displayed increased susceptibility (0.5-fold) to delavirdine, a moderate loss of susceptibility (75-fold) to nevirapine and a slight loss of susceptibility (8-fold) to efavirenz compared to a wild type control RTV. The A98G-G190S-RTV displayed increased susceptibility (0.8-fold) to delavirdine, but a substantial loss of susceptibility to both nevirapine greater than 300-fold) and efavirenz (greater than 250-fold) compared to a wild type control RTV. Although only a slight loss of susceptibility to efavirenz was observed for the individual mutations, the combination of A98G and G190S resulted m a substantial loss of susceptibility to efavirenz. Likewise, this combination of mutation resulted in a greater loss of susceptibility to nevirapine than the sum of the two mutations alone.

EXAMPLE 13

Using Resistance Test Vectors and Site Directed Mutants Correlate Genotypes and Phenotypes Associated with NNRTI Drug Susceptibility and Resistance in HIV: Y181 and A98

Preparation of Resistant Test Vectors and Phenotypic Analysis of Patient 98-1057 Samples A resistance test vector was constructed as described in Example 1 from a patient sample designated 98-1057. This patient had been previously treated with ddI, d4T, AZT, and 3TC (NRTIs), saquinavir and indinavir (PRIs) and delavirdine (an NNRTI). Isolation of viral RNA and RT/PCR was used to generate a patient derived segment that comprised viral sequences coding for all of PR and aa 1-313 RT. The PDS was inserted into an indicator gene viral vector to generate resistance test vector designated RTV-1057. RTV-1057 was then tested in a phenotypic assay to determine accurately and quantitatively the level or susceptibility to a panel of anti-retroviral drugs. This ranel of anti-retroviral drugs comprised members of the classes known as NRTIs (AZT, 3TC, d4T, ddI, and ddC), NNRTIs (delavirdine, efavirenz and nevirapine) and PRIs (indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-1057 in which there was a moderate decrease in delavirdine (35-fold) susceptibility and a significant decrease (610-fold) in nevirapine susceptibility.

Determination of Genotype of Patient HIV Samples

RTV-1057 DNA was analyzed by ABI chain terminator automated sequencing. The nucleotide frequency was compared to the consensus sequence of a wild type clade B HIV-1 (HIV Sequence Database, Los Alamos, N. Mex.). The genotype was examined for sequences that are different from the control sequence. Mutations were noted at positions T39A, M41L, A62V, D67E, T69SST, A98G, I135T, Y181C, T200I and T215Y compared to the control sequence M41L, A62V, D67E, T69SST, and T215Y are associated with NRTI resistance. Mutations at positions I135T and T200I are known polymorphisms in the sequence among different wild-type (drug-sensitive) variants of HIV. Y181C and A98G have been previously shown to be associated with resistance to certain NNRTIs. We examined the mutations Y181C and A98G using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Anti-Retroviral Drugs in HIV The Y181C and A98G mutations were introduced alone and in combination into resistance test vectors using the mega-primer method for site-directed mutagenesis (Sakar and Sommar, Ibid.). Resistance test vectors containing the Y181C mutation (Y131C-RTV) and the A98G mutation (A98G-RTV) and both mutations (Y181C-A98G-RTV) were then tested using the phenotypic assay described earlier and the results were compared to those determined using a genetically defined resistance test vector that was wild type at position 181 and 98. We determined the pattern of phenotypic susceptibility to the NNRTIs, delavirdine, nevirapine and efavirenz, in the three vectors. On a wild type background (i.e. Y181C mutation alone) the Y181C-RTV displayed moderate loss of susceptibility (35-fold) to delavirdine, a significant loss of susceptibility (161-fold) to nevirapine and a slight loss of susceptibility (3-fold) to efavirenz compared to a wild type control RTV. The A98G-RTV displayed a slight loss of susceptibility to delavirdine (3-fold), nevirapine (8-fold) and efavirenz (3-fold) compared to a wild type control RTV. The Y181C-A98G-RTV displayed significant loss of susceptibility (240-fold) to delavirdine, a substantial loss of susceptibility (greater than 800-fold) to nevirapine and a slight loss of susceptibility (7-fold) to efavirenz compared to a wild type control RTV. These data indicated that the combination of the two mutations, Y181C and A98G, resulted in a greater loss of susceptibility to both delavirdine and nevirapine than the sum of effects observed for these two mutations individually.

EXAMPLE 14

Using Resistant Test Vectors and Site Directed Mutants to Correlate Genotypes and Phenotypes Associated with NNRTI Drug Susceptibility and Resistance in HIV: K101 and G190

Preparation of Resistant Test Vectors and Phenotypic Analysis of Patients 98-644 and 98-1060 HIV Samples A resistance test vector was constructed as described in Example 1 from a patient sample designated 98-644. This patient had been previously treated with d4T (an NNRTI), indinavir (a PRI) and efavirenz (an NNRTI). A second resistance test vector was constructed as described in Example 1 from a patient sample designated 98-1060. This patient had been previously treated with d4T (an NNRTI), indinavir (a PRI) and efavirnez (an NNRTI). Isolation of viral RNA and RT/PCR was used to generate a patient derived segment that comprised viral sequences coding for all of PR and aa 1-313 of RT. The PDS was inserted into an indicator gene viral vector to generate resistance test vectors designated RTV-644 and RTV-1060. RTV-644 and RTV-1060 were then tested in a phenotypic assay to determine accurately and quantitatively the level or susceptibility to a panel of anti-retroviral drugs. This panel of anti-retroviral drugs comprised members of the classes known as NNRTIs (AZT, 3TC, d4T, ddI, and ddC), NNRTIs (delavirdine and nevirapine), and PRIs (indinavir, nelfinavir, ritonavir, and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-644 in which there was a very slight (2.5-fold) decrease in delavirdine susceptibility and a significant (600-fold) decrease in nevirapine susceptibility. A pattern of susceptibility to the NNRTIs was observed for patient RTV-644 in which there was a very slight (2.5-fold) decrease in delavirdine susceptibility and a significant (600-fold) decrease in nevirapine susceptibility. A pattern of susceptibility to the NNRTIs was observed for patient RTV-1060 in which woldtype susceptibility (1.5-fold) to delavirdine was observed. A significant decrease in efavirenz susceptibility (900-fold) and a substantial decrease to nevirapine (greater than 800-fold) susceptibility was observed for RTV-1060.

Determination of Genotype of Patient HIV Samples

RTV-644 and RTV-1060 DNA were analyzed by ABI chain terminator automated sequencing. The nucleotide sequence was compared to the consensus of a wild type clade B HIV-1 (HIV Sequence Database, Los Alamos, N. Mex.). The genotype was examined for sequences that are different from the control sequence. Mutations were noted at positions K101E and G190S for RTV-644 compared to the control sequence and mutations were noted at positions K101E, G190S, T200A and T215Y for RTV-1060 compared to the control sequence. The sequence at position T215 was a mixture of wild-type and mutation. A mutation at position K101E had been previously shown to be associated with resistance to several NNRTIs including high level resistance to delavirdine. A mutation at position G190A had previously been shown to be associated with changes in susceptibility to nevirapine. Other changes at position 190 (i.e. E, C and T) have also been reported. We examined the mutations K101E and G190S, using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Antiretroviral Drugs in HIV The K101E and G190S mutations were introduced alone and in combination into resistance test vectors using the megaprimer method for site-directed mutagenesis (Sakar and Sommar, Ibid.). Resistance test vectors containing the K101E mutation (K101E-RTV), the G190S mutation (G190S-RTV) were then tested using the phenotypic assay described earlier and the results were compared to those determined using a genetically defined resistance test vector that was wild type at positions 101 and 190. We determined the pattern of phenotypic susceptibility to the NNRTIs, delavirdine, nevirapine and efavirenz, in all three vectors. On a wild type background (i.e. K101E mutation alone) the K101E-RTV displayed a slight loss of susceptibility (5-fold) to delavirdine and efavirenz (5-fold) and a moderate loss of susceptibility (12-fold) to nevirapine compared to a wild type control RTV. The K101E-G190S-RTV displayed increased susceptibility to delavirdine (0.5-fold), a moderate loss of susceptibility to nevirapine (75-fold) and a slight loss of susceptibility (7.6-fold) to efavirenz compared to a wild type control RTV. The K101E-G190S-RTV displayed wild-type susceptibility (1.4-fold) to delavirdine and a substantial loss of susceptibility; o both nevirapine (greater than 800-fold) and efavirenz (greater than 250-fold) compared to a wild type control RTV.

In this example, the combination of mutations, G190S and K101E, displayed a novel phenotypic pattern. The combination resulted in the reversal of the effect on delavirdine susceptibility observed for the G190S mutation alone and a greater than additive effect on the susceptibility for both nevirapine and efavirenz.

EXAMPLE 15

Using Resistance Test Vectors and Site Directed Mutants to Correlate Genotypes and Phenotypes Associated with NNRTI Drug Susceptibility and Resistance in HIV: V108I Preparation of Resistant Test Vectors and Phenotypic Analysis of Patient 98-652 HIV Samples A resistance test vector was constructed as described in Example 1 from a patient sample designated 98-652. This patient had no previous anti-retroviral treatment. Isolation of viral RNA and RT/PCR was used to generate a patient derived segment that comprised viral sequences coding for all of PR and aa 1-313 or RT. The PDS was inserted into an indicator gene viral vector to generate a resistance test vector designated RTV-652. RTV-652 was then tested in a phenotypic assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine and nevirapine), and PRIs (indinavir, nelfinavir, ritonavir and saquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-652 in which increase susceptibility (0.97-fold) to delavirdine was observed and a slight decrease (5-fold) in nevirapine susceptibility was observed.

Determination of Genotype of Patient HIV Samples

RTV-652 DNA was analyzed by ABI chain terminator automated sequencing. The nucleotide sequence was compared to the consensus sequence of a wild type clade B HIV-1 (HIV Sequence Database, Los Alamos, N. Mex.). The genotype was examined for sequences that are different from the control sequence. Mutations were noted at positions M41L, V108I, I135T, L210W, R21K and T215D compared to the control sequence. M41L, L210W and T215D are associated with NRTI resistance. Mutations at positions I135T and R211K are known polymorphisms in the sequence among different wild-type (drug-sensitive) variants of HIV. V108I is known to be associated with resistance to several NNRTIs. We examined the mutation V108I using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Antiretroviral Drugs in HIV The V108I mutation was introduced into the resistance test vector using the mega-primer method for site directed mutagenesis (Sakar and Sommar, Ibid.). A resistance test vector containing the V108I mutation (V108I-RTV) was then tested using the phenotypic assay described earlier and the results were compared to those determined using a genetically defined resistance test vector that was wild type at position 108. We determined the pattern of phenotypic susceptibility to the NNRTIs, delavirdine, nevirapine and efavirenz, in the V108I-RTV. On a wild type background (i.e. V108I mutation alone) the V108I-RTV displayed wild-type susceptibility (1.3-fold) to delavirdine and efavirenz (1.7-fold) and a slight loss of susceptibility (13-fold) to nevirapine compared to a type control RTV.

EXAMPLE 16

Using Resistance Test Vectors and Site Directed Mutants to Correlate Genotypes and Phenotypes Associated with NNRTI Drug Susceptibility and Resistance in HIV: K103 and K101 and G190

Preparation of Resistant Test Vectors and Phenotypic Analysis of Patient 98-955 HIV Samples A resistance test vector was constructed as described in Example 1 from a patient sample designated 98-955. This patient had been previously treated with nelfinavir (a PRI). Isolation of viral RNA and RT/PCR was used to generate a patient derived segment that comprised viral sequences coding for all of PR and aa 1-313 of RT. The PDS was inserted into an indicator gene viral vector to generate a resistance test vectors designated RTV-955. RTV-955 was then tested in a phenotypic assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine, efavirenz and nevirapine), and PRIs (indinavir, nelfinavir, ritonavir, and aquinavir). An IC50 was determined for the resistance test vector pool for each drug tested. The pattern of susceptibility to all of the drugs tested was examined and compared to known patterns of susceptibility. A pattern of susceptibility to the NNRTIs was observed for patient RTV-955 in which there was a slight decrease (4-fold) in delavirdine susceptibility and a significant decrease (530-fold) in nevirapine susceptibility.

Determination of Genotype of Patient HIV Samples

RTC-955 DNA was analyzed by ABI chain terminator automated sequencing. The nucleotide sequence was compared to the consensus sequence of wild type clade B HIV-1 (HIV Sequence Database, Los Alamos, N. Mex.). The genotype was examined for sequences that are different from the control sequence. Mutations were noted it positions K20R, V35I, A62V, D67N, T69D, 7751, F77L, K101E, X103N, Y115F, F116Y, Q151M, I167V, Y181C, M184V, G190A, I202V, R211K, F214L, T215V, and K219Q compared to the control sequence. Mutations at positions K101E, K103N, Y181C, G190A, and F214L were mixtures of wild-type and the mutation. A62V, D67N, T69D, V751, F77L, Y115F, F116Y, Q151M, M184V, T215V and K219Q are associated with NRTI resistance. Mutations at V35I, R211K and F214L are known polymorphism in the sequence among different wild-type (drug sensitive) variants of HIV. A mutation at position K101E had been previously shown to be associated with resistance to the NNRTIs. A mutation at Y181I had previously been shown to be associated with high level resistance to nevirapine. A mutation at K103N had previously been shown to be associated with resistance to the three NNRTIs, delavirdine and nevirapine and efavirenz. We examined the mutations K101E, J103N and G190A using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Anti-Retroviral Drugs in HIV The K101E, K103N and G190A mutations were introduced alone and in combination inco resistance test vectors using the mega-primer method for site-directed mutagenesis (Sakar and Sommar, Ibid.). Resistance test vectors containing the K101E mutation (K101E-RTV), the K103N mutation (K103N-RTV), the G190 mutation (G190A-RTV) and two mutations (K101E-G190A-RTV) and (K103N-G190A-RTV) were then tested using the phenotypic assay described earlier and the results were compared to those determined using a genetically defined resistance test vector that was wild type at positions 101, 103 and 190. We determined the pattern of phenotypic susceptibility to the NNRTIs, delavirdine, nevirapine, and efavirenz, in all 5 vectors. On a wild type background (i.e. K101E mutation alone) the K101E-RTV displayed a slight loss (5-fold) of susceptibility to delavirdine and efavirenz (5-fold) and a moderate loss of susceptibility (12-fold) to nevirapine (55-fold) and efavirenz (30-fold) compared to a wild type control RTV. On a wild type background (i.e. G190A mutation alone) the G190A-RTV displayed increased susceptibility (8-fold) efavirenz compared to a wild type control RTV. The K101E-G190A-RTV displayed wild-type susceptibility (2-fold) to delavirdine, substantial loss of susceptibility (greater than 800-fold) to nevirapine and a significant loss of susceptibility (120-fold) to efavirenz compared to a wild type control RTV. The K103N-G190-RTV displayed a moderate loss of susceptibility (40-fold) to delavirdine, substantial loss of susceptibility (greater than 800-fold) to nevirapine and a significant loss of susceptibility (215-fold) to efavirenz compared to a wild type control RTV. The introduction of a second mutation to a vector containing the G190A resulted in the reversal of the effect on delavirdine susceptibility observed for the G190A mutation alone. The G190-a mutation displayed an increased susceptibility to delavirdine. However, the addition of either K101E or K103N to the G190A mutation resulted in s slight loss of susceptibility to delavirdine. Furthermore, the combination of G190A and K101E resulted in a greater than additive effect on the loss of susceptibility to nevirapine and efavirenz. Lastly, these data indicated that the combination of the two mutations G190A and K103N resulted in a greater loss of susceptibility to both nevirapine and efavirenz than the sum of effects observed for these two mutations individually.

EXAMPLE 17

Using Test Vectors and Site Directed Mutants to Correlate Genotypes and Phenotypes Associated with NNRTI Drug Susceptibility and Resistance in HIV: V106 and V189 and V181 and F227

Preparation of Resistant Test Vectors and Phenotypic Analysis of Patient 98-1033 and 98-757 HIV Samples A resistance test vector was constructed as described in Example 1 from a patient sample designated 98-1033. This patient had been previously treated with AZT, d4T, 3TC and ddI (NRTI), saquinavir, indinavir and nelfinavir (PRIs and nevirapine (an NNRTI)). A second resistance test vector was constructed as described in Example 1 from a sample obtained from the same patient at a different time point and designated 98-757. This patient had received an additional 8 weeks of treatment with nevirapine (an NNRTI) d4T (an NRTI), and saquinavir and nelfinavir (PRIs). Isolation of viral RNA and RT/PCR was used to generate a patient derived segment that comprised viral sequences coding for all of PR and aa 1-313 of RT. The PDS was inserted into an indicator gene viral vector to generate resistance test vectors designated RTV-1033 and RTV-757. RTV-1033 and RTV-757 were then tested in a phenotypic assay to determine accurately and quantitatively the level of susceptibility to a panel of anti-retroviral drugs. This panel of anti-retroviral drugs comprised members of the classes known as NRTIs (AZT, 3TC, d4T, ddI and ddC), NNRTIs (delavirdine and nevirapine), and PRIs (indinavir, nelfinavir, ritonavir, and saquinavir). An IC50 was determined for the resistance test vector pool for each drug tested. The pattern of susceptibility to all if the drugs tested was examined and compared to known patterns of susceptibility. A pattern of susceptibility to the NNRTIs was observed for patient RTV-1033 in which there was a moderate decrease (30-fold) in delavirdine susceptibility and a substantial decrease (greater than 800-fold in nevirapine susceptibility and a significant decrease (200-fold) in efavirenz susceptibility. A pattern of susceptibility to the NNRTIs was observed for patient RTV-757 in which there was a slight decrease (10-fold) in delavirdine susceptibility and a substantial decrease (greater than 300-fold) in nevirapine susceptibility.

Determination of Genotype of Patient HIV Samples

RTV-1033 and RTV-757 DNA were analyzed by ABI chain terminator automated sequencing. The nucleotide sequence was compared to the consensus sequence of a wild type clade B HIV-1 (HIV Sequence Database, Los Alamos, N. Mex.). The genotype was examined for sequences that are different from the control sequence. Mutations were noted at positions V35I, D67N, T69D, K70R, V106A, V189L, T200A, I202T, R211K, T215F, D218E, K219Q, H221Y, F227L, L228H and R284 for RTV-1033 compared to the control sequence. Mutations were noted at positions V35I, D67N, T69D, K70R, V106A, V108I, L109V, Y108C, V189L, T200A, I202T, R211K, T215F, D218E, K219Q, H221Y, L228H, L283I and R284K for RTV-757 compared to the control sequence. The sequences at positions V106A, V108I and L109V were a mixture of wild-type and mutation. D67N, T69D, K70R, T215F and K219Q are associated with NRTI resistance. Mutations at 735I, T200A, R211K and R284K are known polymorphisms in the sequence among different wild-type drug-sensitive) variants of HIV. A mutation at V106A had previously been shown to be associated with increased resistance to nevirapine. A mutation at V189I had previously been shown to be associated with NNRTI resistance but a mutation to L. at this position had not been previously reported to be associated with NNRTI resistance. A mutation at V108I had previously been shown to be associated with increased resistance to both delavirdine and nevirapine. A mutation at Y181C had also previously been shown to be associated with increased resistance to both delavirdine and nevirapine. We examined the mutations V106A, V189L, V181C and F227L using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Anti-Retroviral Drugs in HIV The mutations V106A, V189L, V181C an F227L were introduced alone and in combination into resistance test vectors using the mega-primer method for site-directed mutagenesis (Sakar and Sommar, Ibid.). Resistance test vectors containing the VI 06A mutation (V106A-RTV), the V189L mutation (V189L-RTV), the V181C mutation (V181C-RTV) and F227L mutation (F227L-RTV) and two mutations (V106A-Y181C-RTV) and (V106A-V189L-RTV) and (V106A-F227-RTV) and (V181C-F227-RTV) and three mutations, (V106A-Y181C-F227L-RTV) were then tested using the phenotypic assay described earlier and the results were compared to those determined using a genetically defined resistance rest vector that was wild type at positions 106, 189, 181 and 227. We determined the pattern of phenotypic susceptibility to the NNRTIs, delavirdine, nevirapine and efavirenz, in all nine vectors. On a wild type background (i.e. V106A mutation alone) the V106A-RTV displayed a slight loss (5-fold) of susceptibility to delavirdine and a moderate loss of susceptibility (60-fold) to nevirapine and wild-type susceptibility (1.7-fold) to efavirenz compared to a wild type control RTV. On a wild type background (i.e. V189L mutation alone the V189-RTV displayed wild type susceptibility to delavirdine (1.8-fold), nevirapine (1.3-fold) and efavirenz (1.3-fold); compared to a wild type control RTV. On a wild type background (i.e. V181C mutation alone) the Y181C-RTV displayed a significant loss of susceptibility (100-f old) to delavirdine and a substantial loss of susceptibility (greater than 800-fold) to nevirapine and a slight loss of susceptibility (4-fold) to efavirenz compared to a wild type control RTV. On a wild type background (i.e. F227L mutation alone) the F227L-RTV displayed increased susceptibility (0.03-fold) to delavirdine and efavirenz (0.48-fold) and a slight loss of susceptibility (3-fold) to nevirapine compared to a wild type control RTV. The V106A-Y181C-RTV displayed a significant loss of susceptibility (100-fold) to delavirdine, a substantial loss of susceptibility (greater than 800-fold) to nevirapine and slight loss of susceptibility (4-fold) to efavirenz compared to a wild type control RTV. The V106A-V189L-RTV displayed a slight loss of susceptibility (3-fold) to delavirdine, a moderate loss of susceptibility (50-fold) to nevirapine and wild-type susceptibility (1-fold) to efavirenz compared to a wild type control RTV. The V106A-F227-RTV displayed a slight loss of susceptibility (3-fold) to delavirdine, a substantial loss of susceptibility (greater than 800-fold) to nevirapine and a slight loss of susceptibility (8-fold) to efavirenz compared to a wild type control RTV. The Y181C-F227L-RTV displayed increased susceptibility (0.89-fold) to delavirdine and efavirenz (0.99-fold) and a significant loss of susceptibility (285-fold) to nevirapine compared to a wild type control RTV. The V106A-Y181C-F227L-RTV displayed a moderate loss (50-fold) of susceptibility to delavirdine and a substantial loss of susceptibility (greater than 800-fold) to nevirapine and a slight loss of susceptibility (12-fold) to efavirenz compared to a wild type control RTV.

EXAMPLE 18

Using Resistance Test Vectors and Site Directed Mutants to Correlate Genotypes and Phenotypes Associated with NNRTI Drug Susceptibility and Resistance in HIV: Y188 and L100 and K103

Preparation of Resistance Test Vectors and Phenotypic Analysis of Patient 98-1058 HIV Samples A resistance test vector v.-as constructed as described in Example 1 from a patient sample designated 98-1058. This patient had been previously treated with ddI, d4T, AZT, 3TC, ddC and abacavir (NRTIs), indinavir and amprenavir (PRIs) and nevirapine (an NNRTI). Isolation of viral RNA and RT/PCR was used to generate a patient derived segment that comprised viral sequences coding for all of RP and aa 1-313 of RT. The PDS was inserted into an indicator gene viral vector to generate a resistance test vector designated RTV-1058. Individual clones of RTV-1058 were selected and were then tested in a phenotypic assay to determine accurately and quantitatively the level of susceptibility to a panel of anti-retroviral drugs. The panel of anti-retroviral drugs comprised members of the classes known as NRTIs (AZT, 3TC, d4T, kkI and ddC), NNRTIs (delavirdine and nevirapine), and PRIs (indinavir, nelfinavir, ritonavir, and saquinavir). An IC50 was determined for the resistance test vector pool for each drug tested. The pattern of susceptibility to all or the drugs tested was examined and compared to known patterns of susceptibility. A pattern of susceptibility to the NNRTIs was observed for clones 4, and from patient RTV-1058. Clone 4 displayed a significant loss of susceptibility (85-fold) for delavirdine and a substantial loss of susceptibility (greater than 800-fold) for nevirapine. Clone displayed a substantial loss of susceptibility (150-fold) to delavirdine and a significant loss of susceptibility (120-fold) to nevirapine. Clone displayed a substantial loss of susceptibility (greater than 250-fold) to delavirdine and (greater than 800-fold) to nevirapine.

Determination of Genotype of Patient HIV Samples

RTV-1058 DNA was analyzed by ABI chain terminator automated sequencing. The nucleotide sequence was compared to the consensus sequence of a wild type clade B HIV-1 (HIV sequence Database, Los Alamos, N. Mex.). The genotype was examined for sequences that are different from the control sequence. Mutations were noted as positions M41L, A62V, D67N, T69SST, L74V, L100I, K103N, V181I, I135T, T200S, L210W, R211K and T215Y compared to the control sequence. L74V and L100I were mixtures of wild-type and mutation. Clone 4 contained mutations at positions K103N. Clone contained mutations at positions L100I and K103N. Clone contained mutations at positions L100I, K103N and Y188L. M41L, A62V, D67N, T69SST, L74V, L210W and T215Y are associated with NRTI resistance. Mutations at positions I135T, T200S and R211T are known polymorphisms in the sequence among different wild-type (drug-sensitive) variants of HIV. A mutation at L100I had previously been shown to be associated with resistance to delavirdine and nevirapine. A mutation at K103N had previously been shown to be associated with resistance to delavirdine, nevirapine and efavirenz. We examined the mutations, Y188L, L100I and K103N, using site directed mutagenesis and in vitro phenotypic susceptibility testing to correlate the observed changes in genotype with phenotype.

Site Directed Mutagenesis is Used to Confirm the Role of Specific Mutations in Phenotypic Susceptibility to Anti-Retroviral Drugs in HIV The mutations Y188L, L100I and K103N were introduced alone and in combination into resistance test vectors using the mega-primer method for site-directed mutagenesis (Sakar and Sommar, Ibid.). Resistance test vectors containing the Y188L mutation (K103N-RTV), the two mutations (K103N-Y188L-RTV) and (L100I-K103N-RTV), and the three mutations (L100I-K103N-Y188L-RTV) were then tested using the phenotypic assay described earlier and tie results were compared to those determined using a genetically defined resistance test vector that was wild type at positions 188, 100, and 103. We determined the pattern of phenotypic susceptibility to the NNRTIs, delavirdine, nevirapine and efavirenz, in all 6 vectors. On a wild type background (i.e. Y188L mutation alone) the Y188L-RTV displayed a slight loss of susceptibility (9-fold) to delavirdine, a susceptibility (10-fold) to efavirenz compared to a wild type control RTV. On a wild type background (i.e. L100I mutation alone) displayed a moderate loss of susceptibility (10-fold) and a slight loss of susceptibility (3-fold) to nevirapine compared to a wild type control RTV. On a wild type background (i.e. K103M mutation alone) the K103N-RTV displayed moderate loss of to delavirdine susceptibility (50-fold), nevirapine (55-fold) and efavirenz (30-fold) compared to a wild type control RTV. The K103N-Y188L-RTV displayed substantial loss of susceptibility to delavirdine (greater than 250-fold), nevirapine (greater than 800-fold) and efavirenz (greater that 250-fold) compared to a wild control RTV. The L100I-K100I-RTV displayed substantial loss of susceptibility (greater that 250-fold) to delavirdine and efavirenz (greater that 250-fold) and a moderate loss of susceptibility (70-fold) to nevirapine compared to a wild type control RTV. The L100I-K103N-Y188L-RTV displayed substantial loss of susceptibility to delavirdine (greater than 250-fold), nevirapine (greater than 250-fold) compared to a wild type control RTV. Novel combinations resulted in unpredicted resistance patterns that were different from those patterns observed for each mutation alone.

What is claimed is:

1. A method of assessing the effectiveness of a non-nucleoside reverse transcriptase inhibitor (NNRTI) on a human immunodeficiency virus type 1 (HIV-1)-infected patient, comprising detecting in a plasma sample collected from the HIV-1-infected patient the presence of an HIV-1 reverse transcriptase (RT) nucleic acid that encodes one of the following combination of mutations: G190A/S and K101E, or G190A/S and A98G, wherein said combination of mutations is associated with increased susceptibility to delavirdine and decreased susceptibility to nevirapine and efavirenz.

2. The method of claim 1, wherein the mutation at codon 190 encodes alanine (A).

3. The method of claim 1, further comprising evaluating whether the nucleic acid encoding reverse transcriptase has an additional mutation K103N, wherein the presence of the additional mutation in combination with the mutations G190A/S and K101E, or G190A/S and A98G, is correlated with decreased susceptibility to delavirdine, nevirapine, and efavirenz.

4. The method of claim 1, wherein the mutation at codon 190 encodes serine (S).

* * * * *

UNITED STATES PATENT AND TRADEMARK OFFICE
CERTIFICATE OF CORRECTION

PATENT NO.       : 7,579,143 B2
APPLICATION NO.  : 10/758683
DATED            : August 25, 2009
INVENTOR(S)      : Jeannette Whitcomb It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1249 days.

Signed and Sealed this

Fourteenth Day of September, 2010

David J. Kappos
*Director of the United States Patent and Trademark Office*